(12) United States Patent
Vallier et al.

(10) Patent No.: US 11,697,823 B2
(45) Date of Patent: Jul. 11, 2023

(54) CONTROLLABLE TRANSCRIPTION

(71) Applicant: Cambridge Enterprise Limited (GB/GB), Cambridgeshire (GB)

(72) Inventors: Ludovic Vallier, Cambridgeshire (GB); Mark Kotter, Cambridgeshire (GB); Matthias Pawlowski, Cambridgeshire (GB); Alessandro Bertero, Cambridgeshire (GB); Daniel Ortmann, Cambridgeshire (GB)

(73) Assignee: Cambridge Enterprise Limited, Cambridge (GB)

( * ) Notice: Subject to any disclaimer, the term of this patent is extended or adjusted under 35 U.S.C. 154(b) by 644 days.

(21) Appl. No.: 16/463,829

(22) PCT Filed: Nov. 24, 2017

(86) PCT No.: PCT/GB2017/053531
§ 371 (c)(1),
(2) Date: May 23, 2019

(87) PCT Pub. No.: WO2018/096343
PCT Pub. Date: May 31, 2018

(65) Prior Publication Data
US 2019/0338309 A1 Nov. 7, 2019

(30) Foreign Application Priority Data
Nov. 24, 2016 (GB) ..................... 1619876

(51) Int. Cl.
| | | |
|---|---|---|
| C12N 15/63 | (2006.01) | |
| C12N 15/79 | (2006.01) | |
| C07H 21/04 | (2006.01) | |
| C12N 15/86 | (2006.01) | |
| A61K 35/545 | (2015.01) | |
| C12N 5/0735 | (2010.01) | |
| C12N 5/074 | (2010.01) | |
| C12N 5/079 | (2010.01) | |
| C12N 5/077 | (2010.01) | |
| C12N 9/22 | (2006.01) | |
| C12N 15/11 | (2006.01) | |
| G01N 33/50 | (2006.01) | |

(52) U.S. Cl.
CPC ............ *C12N 15/86* (2013.01); *A61K 35/545* (2013.01); *C12N 5/0606* (2013.01); *C12N 5/0607* (2013.01); *C12N 5/0622* (2013.01); *C12N 5/0658* (2013.01); *C12N 9/22* (2013.01); *C12N 15/11* (2013.01); *G01N 33/5005* (2013.01); *C12N 2310/20* (2017.05); *C12N 2501/999* (2013.01); *C12N 2506/02* (2013.01); *C12N 2506/03* (2013.01); *C12N 2750/14143* (2013.01); *C12N 2800/80* (2013.01); *C12N 2830/003* (2013.01); *G01N 2800/00* (2013.01)

(58) Field of Classification Search
CPC ........ C12N 15/63; C12N 15/79; C12N 15/85; C12N 15/86; C12N 2830/003; C12N 2310/20; C07H 21/04
See application file for complete search history.

(56) References Cited

U.S. PATENT DOCUMENTS

| | | |
|---|---|---|
| 2013/0212722 A1 | 8/2013 | West |
| 2018/0320186 A1 | 11/2018 | Kanemaki et al. |
| 2019/0010490 A1 | 1/2019 | Cowan et al. |
| 2019/0076551 A1 | 3/2019 | Bogorad et al. |
| 2019/0112353 A1 | 4/2019 | Yang et al. |

FOREIGN PATENT DOCUMENTS

| | | |
|---|---|---|
| KR | 101535070 B1 | 7/2015 |
| WO | 1997/38117 A1 | 10/1997 |
| WO | 1998/10084 A1 | 3/1998 |
| WO | 2007/014275 A2 | 2/2006 |
| WO | 2006/131543 A1 | 12/2006 |
| WO | 2007/014275 A2 | 2/2007 |
| WO | 2008/088863 A2 | 7/2008 |
| WO | 2010/109187 A1 | 9/2010 |
| WO | WO2010/109187 † | 9/2010 |
| WO | WO 2010/117464 A1 | 10/2010 |
| WO | 2016/163958 A1 | 10/2016 |
| WO | WO 2016/183041 A2 | 11/2016 |
| WO | 2016/210313 | 12/2016 |
| WO | 2017/109757 A1 | 6/2017 |
| WO | WO 2018/096343 A1 | 5/2018 |
| WO | 2018/204262 | 11/2018 |

OTHER PUBLICATIONS

Kotterman et al., 2014, Nature Reviews, vol. 15, p. 445-451.*
Shim et al., 2017, Current Gene Therapy, vol. 17, No. 5, p. 1-18.*
Lenzi et al., 2014, NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16.*
EP 17807909.1-1118—Office Action, dated Sep. 21, 2020, 8 pages.
Ramachandra et al. "Efficient recombinase-mediated cassette exchange at the AAVS1 locus in human embryonic stem cells using baculoviral vectors." Nucleic acids research 39, No. 16 (2011): e107-e107, 13 pages.

(Continued)

*Primary Examiner* — Shin Lin Chen
(74) *Attorney, Agent, or Firm* — Goodwin Procter LLP

(57) ABSTRACT

The present invention relates to a stable method for introducing at least one inducible cassette into a cell, and permitting controllable transcription from within that inducible cassette. The method may be used for any cell type, from any eukaryotic organism, but has a particular application in the introduction of inducible cassettes into pluripotent stem cells, such as animal or human pluripotent stem cells (hPSCs). The inducible cassette is controllably inserted in such a way to ensure that the genetic material it contains is not silenced or subject to negative influences from the insertion site, and transcription of the genetic material is controlled.

23 Claims, 34 Drawing Sheets

Specification includes a Sequence Listing.

(56) References Cited

OTHER PUBLICATIONS

Bäckman et al., "Generalized tetracycline induced Cre recombinase expression through the ROSA26 locus of recombinant mice." Journal of neuroscience methods 176, No. 1 (2009): 16-23.
Urlinger et al., "Exploring the Sequence Space for Tetracycline-Dependent Transcriptional Activators: Novel Mutations Yield Expanded Range and Sensitivity," PNAS, Jul. 5, 2000, vol. 97, No. 14, pp. 7963-7968.
Cerbini et al., "Transcription Activator-Like Effector Nuclease (TALEN)-Mediated CLYBL Targeting Enables Enhanced Transgene Expression and One-Step Generation of Dual Reporter Human Induced Pluripotent Stem Cell (iPSC) and Neural Stem Cell (NSC) Lines," PLOS ONE, Jan. 15, 2015, 18 pages.
Bertero et al., "Optimized inducible shRNA and CRISPR/Cas9 platforms for in vitro studies of human development using hPSCs", Development, vol. 143, No. 23, pp. 4405-4418 (2016).
Dekelver et al., "Functional genomics, proteomics, and regulatory DNA analysis in isogenic settings using zinc finger nuclease-driven transgenesis into a safe harbor locus in the human genome", Genome Research, vol. 20, No. 8, pp. 1133-1142 (2010).
International Search Report from International Application No. PCT/GB2017/053531, 9 pages, dated Mar. 26, 2018, application now published as International Publication No. WO2018/096343 on May 31, 2018.
Papapetrou and Schambach, "Gene Insertion Into Genomic Safe Harbors for Human Gene Therapy", Molecular Therapy, vol. 24, No. 4, pp. 678-684 (2016).
Pawlowski et al., "Inducible and Deterministic Forward Programming of Human Pluripotent Stem Cells into Neurons, Skeletal Myocytes, and Oligodendrocytes", Stem Cell Reports, vol. 8, No. 4, pp. 803-812 (2017).
Petersen et al., "UW-Madison Human Stem Cell Gene Editing Service a Campus Resource for Applying CRISPR/Cas9in Human Pluripotent Stem Cells", University of Wisonsin. Retreived from the Internet: https://waisman.wiscweb.wisc.edu/wp-content/uploads/sites/69/2017/08/GeneEditingServiceSept2016.pdf (2016).
Qian et al., "A simple and efficient system for regulating gene expression in human pluripotent stem cells and derivatives", Stem Cells, vol. 32, No. 5, pp. 1230-1238 (2014).
Sadelain et al., "Safe harbours for the integration of new DNA in the human genome", Nature Rev. Cancer, vol. 12, No. 1, pp. 51-58 (2011).
Pei et al., "A platform for rapid generation of single and multiplexed reporters in human iPSC lines." Scientific reports 5, No. 1 (2015): 1-10.
Anonymous: "Introduction to Tet expression systems", eNews, Apr. 1, 2015 (Apr. 1, 2015), pp. 1-2, XP055713341, The Jackson Laboratory, Retrieved from the Internet: URL:https://www.jax.org/news-and-insights/2015/april/introduction-to-tetÂ-expression-systems#, 3 pages.
Iacovino et al., "Inducible cassette exchange: a rapid and efficient system enabling conditional gene expression in embryonic stem and primary cells." Stem cells 29, No. 10 (2011): 1580-1588.
Anonymous: "Introduction to Tet expression systems", The Jackson Laboratory, Retrieved from the Internet: URL:https://https://www.jax.org/news-and-insights/2015/april/introduction-to-tet-expression-systems, accessed Sep. 5, 2020, 2 pages.
Forsberg et al.,"Efficient reprogramming of adult neural stem cells to monocytes by ectopic expression of a single gene", Proceedings of the National Academy of Sciences (PNAS), Jul. 30, 2010, vol. 107, No. 33, pp. 14658-14660.
Kazuyuki et al. "Induced-Pluripotent-Stem-Cell-Derived Primitive Macrophages Provide a Platform for Modeling Tissue-Resident Macrophage Differentiation and Function", Immunity. Jul. 18, 2017, vol. 47, No. 1, pp. 189-190.
Akhtar et al., "A Transposon-Mediated System for Flexible Control of Transgene Expression in Stem and Progenitor-Derived Lineages", Stem Cell Reports, Mar. 1, 2015, vol. 4, No. 3, (Mar. 1, 2015), pp. 323-331.

Xie et al., "Stepwise Reprogramming of B Cells into Macrophages", Cell, Mar. 28, 2004, vol. 117, No. 5, pp. 670-674.
Feng et al.,"PU.1 and C/EBPa/b convert fibroblasts into macrophage-like cells", Proceedings of the National Academy of Sciences (PNAS)., Apr. 22, 2008, vol. 105, No. 16, pp. 6057-6062.
Speicher, et al., "Generating microglia from human pluripotent stem cells: novel in vitro models for the study of neurodegeneration", Molecular Neurodegeneration, vol. 14, No. 1, Dec. 1, 2019, pp. 1-16.
International Search Report and Written Opinion for International Application No. PCT/EP2020/064649, dated Sep. 18, 2020. (9 pages).
Abud, et al.: iPSC-Derived Human Microglia-like Cells to Study Neurological Diseases. Neuron, 2017, 94:278-293.e9.
Butovsky 0, Weiner HL: Microglial signatures and their role in health and disease. Nat Rev Neurosci., 2018, 19.
Cantos, et al. "Identification of 'safe harbor' loci in indica rice genome by harnessing the property of zinc-finger nucleases to induce DNA damage and repair." Frontier in Plant Science, 2014, 5: 302, pp. 1-8.
Cerbini, et al. "Transcription Activator Like Effector Nuclease (TALEN)-Mediated CLYBL Targeting Enables Enhanced Transgene Expression and One-Step Generation of Dual Reporter Human Induced Pluripotent Stem Cell (iPSC) and Neural Stem Cell (NSC) Lines." Plos One, 2015.
Chung, et al. "Human Embryonic Stem Cell Lines Generated without Embryo Destruction." 2008, Cell Stem Cell, 2(2) pp. 113-117.
Cohen and Melton. "Turning straw into gold: directing cell fate for regenerative medicine." Nat Rev Genet 2011, 12:243-52.
Douvaras, et al.: Directed Differentiation of Human Pluripotent Stem Cells to Microglia. Stem cell reports, 2017, 8:1516-1524.
Gaj, et al. "ZFN, TALEN, and CRISPR/Cas-based methods for genome engineering." Trends Biotechnol., 2013, 31(7):397-405.
Ginhoux, et al.: Fate mapping analysis reveals that adult microglia derive from primitive macrophages. Science, (80) 2010, 330:841-5.
Gomez Perdiguero, et al.: "Tissue-resident macrophages originate from yolk-sac derived erythro-myeloid progenitors." Nature. 2015, 518:547-51.
Haenseler, et al. "A Highly Efficient Human Pluripotent Stem Cell Microglia Model Displays a Neuronal-Co-culture-Specific Expression Profile and inflammatory Response." Stem cell reports. 2017, 8:1727-1742.
Hagan, et al. Comparative Anatomy and Histology, 2012, pp. 339-394.
Keren-Shaul, et al. "A unique Microglia Type Associated with Restricting Development of Alzheimer's Disease." Cell, 2017, 169:1276-1290.e17.
Kettenmann, et al. "Physiology of microglia." Physiol Rev., 2011, 91:461-553.
Krasemann, et al. "The TREM2-APOE Pathway Drives the Transcriptional Phenotype of Dysfunctional Microglia in Neurodegenerative Diseases." Immunity, 2017, 17:566581.e9.
Ladewig, et al. "Leveling Waddington: the emergence of direct programming and the loss of cell fate hierarchies." Nat Rev Mol Cell Biol, 2013, 14:225-36.
McGrath, et al. "Circulation is established in a stepwise pattern in the mammalian embryo." Blood, 2003, 101:1669-76.
Muffat, et al. "Efficient derivation of microglia-like cells from human pluripotent stem cells." Nat Med, 2016, 22:1355-1367.
Pandya, et al.: Differentiation of human and murine induced pluripotent stem cells to microglia-like cells. Nat Neurosci, 2017, 20:753-759.
Pellenz et al. "New human chromosomal sites with 'safe harbor' potential for targeted transgene insertion." Human Gene Therapy, 2019, 1-47.
Hui, et al "FGF Family: From Drug Development to Clinical Application." Int. J. Mol. Sci., 2018, 19(7), 1875.
Ransohoff. "How neuroinflammation contributes to neurodegeneration." Science, 2016, 353:777-83.
Reu, et al. "The Lifespan and Turnover of Microglia in the Human Brain." Cell Rep, 2017, 20:77V784.

(56) References Cited

OTHER PUBLICATIONS

Schafer and Stevens. "Microglia Function in Central Nervous System Development and Plasticity." Cold Sping Harb Perspect Biol, 2015, 7:a020545.
Takahashi, et al. "Induction of pluripotent stem cells from adult human fibroblasts by defined factors." Cell, 2007, 131:861-72.
Thomson, et al. "Embryonic stem cell lines derived from human blastocysts." Science. 1998, 282:1145-7.
Vlahos et al. "A Specific Inhibitor of Phosphatidylinositol 3-Kinase,2-(4-Morpholinyl)-8-phenyl-4H-I-benzopyran-4-one (LY294002)." The Journal of Biological Chemistry, 1994, 269(7), pp. 5241-5248.
Zhang, et al. "Rapid single-step induction of functional neurons from human pluripotent stem cells." Neuron, 2013, 78:785-98.
Beard, C., et al., "Efficient method to generate single-copy transgenic mice by site-specific integration in embryonic stem cells", Genesis. 2006;44(1):23-28.
Ordovas, L., et al., "Rapid and Efficient Generation of Recombinant Human Pluripotent Stem Cells by Recombinase-mediated Cassette Exchange in the AAVS1 Locus", J Vis Exp. 2016;(117):54718.
Ordovas, L., et al., "Efficient Recombinase-Mediated Cassette Exchange in hPSCs to Study the Hepatocyte Lineage Reveals AAVS1 Locus-Mediated Transgene Inhibition", Stem Cell Reports 2015;5(5):918-931.
Carey, B., et al., "Single-gene transgenic mouse strains for reprogramming adult somatic cells", Nat Methods. 2010;7(1):56-59.
Premsrirut, P.K., et al., "Rapid and Scalable System for Studying Gene Function in Mice Using Conditional RNA Interference", Cell. 2011;145(1):145-158.
Li, S., et al., "Overview of the reporter genes and reporter mouse models", Animal Model Exp Med. 2018;1 (1):29-35.
Hochedlinger, K., et al., "Ectopic expression of Oct-4 blocks progenitorcell differentiation and causes dysplasia in epithelial tissues", Cell 2005;121 (3):465-477.
Sim, X., et al., "A Doxycycline-Inducible System for Genetic Correction of iPSC Disease Models", Methods Mal Biol. 2014;1353:13-23.
Clontech Tet-OffR and Tet-OnR Gene Expression Systems User Manual, Clontech Laboratories, Inc., Mountain View, CA 94043 (USA), published Oct. 2012.
Gossen, M., et al., "Transcriptional activation by tetracyclines in mammalian cells", Science. 1995;268 (5218):1766-1769.
Mukherjee, S., et al., "Gene therapy for PIDs: progress, pitfalls and prospects", Gene. 2013;525(2):174-181.
Merkert, S., et al., "Site-Specific Genome Engineering in Human Pluripotent Stem Cells", Int J Mal Sci. 2016;17(7):1000.
Kennedy, K.A., et al., "Retinoic acid enhances skeletal muscle progenitor formation and bypasses inhibition by bone morphogenetic protein 4 but not dominant negative b-catenin", BMC Biol. 2009;7:67.
Chen, J., et al., "Retinoic Acid Receptor Signaling in the Differentiation of Pluripotent Stem Cells into Skeletal Muscle Lineage", Pluripotent Stem Cells—From the Bench to the Clinic, IntechOpen, London. doi:10.5772/62819; Jul. 20, 2016.
Honore, S.M., et al., "Sox10 is required for the early development of the prospective neural crest in Xenopus embryos", Dev Biol. 2003;260(1):79-96.
Li, P., et al., "Accelerated generation of oligodendrocyte progenitor cells from human induced pluripotent stem cells by forced expression of Sox10 and Olig2", Sci China Life Sci. 2016;59(11):1131-1138.
Lombardo, A., et al., "Site-specific integration and tailoring of cassette design for sustainable gene transfer", Nat Methods. 2011;8(10):861-869.
Aubrey, B.J., et al., "An inducible lentiviral guide RNA platform enables the identification of tumor-essential genes and tumor-promoting mutations in vivo", Cell Rep 2015;10(8):1422-1432.
Nowak, C.M., et al., "Guide RNA engineering for versatile Cas9 functionality", Nucleic Acids Res. 2016,44(20):9555-9564.
Pei, Y. et al., A platform for rapid generation of single and multiplexed reporters in human iPSC lines. Sci Rep 5, 9205 (2015).†
Iacovino et al. Inducible cassette exchange: a rapid and efficient system enabling conditional gene expression in embryonic stem and primary cells. Stem Cells. Oct. 29, 2011(10):1580-1588.†
Sadelain, et al., Safe Harbours for the integration of new DNA in the human genome. Nat Rev Cancer 12, 51-58 (2012).†
Introduction to Tet Expression Systems. eNews Apr. 1, 2015; Jackson Lab.†

\* cited by examiner
† cited by third party

CAP = Constitutively active promoter
GM = Genetic modulator (e.g. rtTA)
S1-n = Constitutively expressed genetic sequence 1-n
iS1-n = inducibly expressed genetic sequence

Principle Invention

Extension to polycistronic vector contructs

Extension to multiple GSH

SEQUENCE LISTING

<160> NUMBER OF SEQ ID NOS: 88

<210> SEQ ID NO 1
<211> LENGTH: 19
<212> TYPE: DNA
<213> ORGANISM: Artificial Sequence
<220> FEATURE:
<223> OTHER INFORMATION: TetO2 19 nucleotide sequence

<400> SEQUENCE: 1
tccctatcag tgatagaga                                          19

<210> SEQ ID NO 2
<211> LENGTH: 1797
<212> TYPE: DNA
<213> ORGANISM: Homo sapiens

<400> SEQUENCE: 2
gctcgaaacc ggacggagcc attgctctcg cagagggagg agcgcttccg gctagcctct      60
tgtcgccgat tggccgtttc tcctcccgcc gtgtgtgaaa acacaaatgg cgtattctgg     120
ttggagtaaa gctcctgtca gttacgccgt cgggagtacg cagccgctta gcgactctcg     180
cgttgccccc tgggtggggc gggtaggtag gtggggtgta gagatgctgg gtgtgcgggc     240
gcggccggcc tcctgcggcg ggaggggagg gtcagtgaaa tcggctctgg cgcgggcgtc     300
ctcccaccct cccttccctt cggggagtc ggtttacccg ccgcctgctt gtcttcgaca      360
cctgattggc tgtcgaagct gtgggaccgg gcccttgcta ctggctcgag tctcacatga     420
gcgaaaccac tgcgcgggc gcggggtgg cgggaggcg ggcgttggta cggtcctccc        480
cgaggccgag cgccgcagtg tctggccccg cgcccctgcg caacgtggca ggaagcgcgc     540
gctggaggcg gggcgggct gccggccgag acttctggat ggcggcggcc gcggctccgc      600
cccgggttcc caccgcctga agggcgagac aagcccgacc tgctacaggc actcgtgggg     660 gtggggagg agcgggggtc ggtccggctg gtttgtgggt gggaggcgct tgttctccaa      720
aaaccggcgc gagctgcaat cctgagggag ctgcggtgga ggaggtggag agaaggccgc     780
acccttctgg gcaggggag gggagtgccg caataccttt atgggagttc tctgctgcct     840
cccgtcttgt aaggaccgcc ctgggcctgg aagaagccct ccctcctttc ctcctcgcgt     900
gatctcgtca tcgcctccat gtcgagtcgc ttctcgatta tgggcgggat tcttttgcct     960
aggcttaagg ggctaacttg gtccctgggc gttgccctgc aggggagtga gcagctgtaa    1020
gatttgaggg gcgactccga ttagtttatc ttcccacgga ctagagttgg tgtcgaggtt    1080
attgtaataa gggtggggta gggaaatgga gcttagtcat tcacctgggg ctgatttat    1140 gcaacgagac tgcggattat cactactat cattttgga gcattttct agagacagac       1200

```
ataaagcatg atcacctgag ttttatacca tttgagaccc ttgctgcacc accaaagtgt    1260
agcatcaggt taaatcttaa tagaaaaatt ttagcttttg cttgagaaac cagtgcttcc    1320
ctccctcacc ctctctcccc aggctctcta cccctttgca tccctaccag gcatcttagc    1380
aactctcact catacttgat cccatttttcc atttgttgta cttgctcctc tagtattcag    1440
acatagcact agctttctcc ctctcttgat cttgggtagc ctggtgtctc gcgaaaccag    1500
acagattggt tccaccacaa attaaggctt gagctggggc ttgactctta cccagcagtg    1560 ctttttattcc tccctagttc acgttcttaa atgtttatct tgattttcat tttatccttt    1620
ttccttagct gggattctgt ccctgaccgt cttcacagtc caggtgatct tgactactgc    1680
tttacagaga attggatctg aggttaggca acatctccct ttttcttcct ctaaatacct    1740
ctcatttctg ttcttaccag ttagtaactg atctcagatg cctgtgtgat agcttcc       1797
```

<210> SEQ ID NO 3
<211> LENGTH: 651
<212> TYPE: DNA
<213> ORGANISM: Artificial Sequence
<220> FEATURE:
<223> OTHER INFORMATION: STDtetR-nls

<400> SEQUENCE: 3

```
atgccaaaaa agaagaggaa ggtatctaga ttagataaaa gtaaagtgat taacagcgca     60
ttagagctgc ttaatgaggt cggaatcgaa ggtttaacaa cccgtaaact cgcccagaag    120
ctaggtgtag agcagcctac attgtattgg catgtaaaaa ataagcgggc tttgctcgac    180
gccttagcca ttgagatgtt agataggcac atactcact tttgcccttt agaaggggaa     240
agctggcaag atttttttacg taataacgct aaaagttta gatgtgcttt actaagtcat    300
cgcgatggag caaagtaca tttaggtaca cggcctacag aaaaacagta tgaaactctc    360
gaaaatcaat tagccttttt atgccaacaa ggttttttcac tagagaatgc attatatgca    420
ctcagcgctg tggggcattt tactttaggt tgcgtattgg aagatcaaga gcatcaagtc    480
gctaaagaag aaagggaaac acctactact gatagtatgc cgccattatt acgacaagct    540
atcgaattat ttgatcacca aggtgcagag ccagccttct tattcggcct tgaattgatc    600
atatgcggat tagaaaaaca acttaaatgt gaaagtgggt ctccgcggta a              651
```

<210> SEQ ID NO 4
<211> LENGTH: 216
<212> TYPE: PRT
<213> ORGANISM: Artificial Sequence
<220> FEATURE:
<223> OTHER INFORMATION: STDtetR-nls

<400> SEQUENCE: 4

```
Met Pro Lys Lys Lys Arg Lys Val Ser Arg Leu Asp Lys Ser Lys Val
1               5                   10                  15

Ile Asn Ser Ala Leu Glu Leu Leu Asn Glu Val Gly Ile Glu Gly Leu
            20                  25                  30

Thr Thr Arg Lys Leu Ala Gln Lys Leu Gly Val Glu Gln Pro Thr Leu
        35                  40                  45

Tyr Trp His Val Lys Asn Lys Arg Ala Leu Leu Asp Ala Leu Ala Ile
    50                  55                  60

Glu Met Leu Asp Arg His His Thr His Phe Cys Pro Leu Glu Gly Glu
65                  70                  75                  80

Ser Trp Gln Asp Phe Leu Arg Asn Asn Ala Lys Ser Phe Arg Cys Ala
            85                  90                  95
```

```
Leu Leu Ser His Arg Asp Gly Ala Lys Val His Leu Gly Thr Arg Pro
            100                 105                 110

Thr Glu Lys Gln Tyr Glu Thr Leu Glu Asn Gln Leu Ala Phe Leu Cys
        115                 120                 125

Gln Gln Gly Phe Ser Leu Glu Asn Ala Leu Tyr Ala Leu Ser Ala Val
    130                 135                 140

Gly His Phe Thr Leu Gly Cys Val Leu Glu Asp Gln Glu His Gln Val
145                 150                 155                 160

Ala Lys Glu Glu Arg Glu Thr Pro Thr Thr Asp Ser Met Pro Pro Leu
                165                 170                 175

Leu Arg Gln Ala Ile Glu Leu Phe Asp His Gln Gly Ala Glu Pro Ala
            180                 185                 190

Phe Leu Phe Gly Leu Glu Leu Ile Ile Cys Gly Leu Glu Lys Gln Leu
        195                 200                 205

Lys Cys Glu Ser Gly Ser Pro Arg
    210                 215
```

<210> SEQ ID NO 5
<211> LENGTH: 651
<212> TYPE: DNA
<213> ORGANISM: Artificial Sequence
<220> FEATURE:
<223> OTHER INFORMATION: OPTtetR

<400> SEQUENCE: 5

```
atgcccaaga aaaagcggaa ggtgtcccgg ctggacaaga gcaaagtgat caacagcgcc      60
ctggaactgc tgaacgaagt gggcatcgag ggcctgacca cccggaagct ggcccagaaa     120
ctgggcgtgg aacagcccac cctgtactgg cacgtgaaga caagcgggc cctgctggac      180
gccctggcca tcgagatgct ggaccggcac cacacacact tttgcccct ggaaggcgaa      240
agctggcagg acttcctgcg gaacaacgcc aagagcttca gatgcgccct gctgagccac     300
cgggacggcg ccaaagtgca cctgggcacc agacccaccg agaagcagta cgagacactg     360
gaaaaccagc tggccttcct gtgccagcag ggcttcagcc tggaaaacgc cctgtacgcc     420
ctgagcgccg tgggccactt taccctgggc tgcgtgctgg aagatcagga acaccaggtc     480
gccaaagagg aaagagagac acccaccacc gacagcatgc cccccctgct gagacaggcc     540
atcgagctgt tcgatcatca aggcgccgag cccgccttcc tgttcggcct ggaactgatc     600
atctgcggcc tcgagaagca gctgaagtgc gagagcggct cccccagatg a            651
```

<210> SEQ ID NO 6
<211> LENGTH: 216
<212> TYPE: PRT
<213> ORGANISM: Artificial Sequence
<220> FEATURE:
<223> OTHER INFORMATION: OPTtetR

<400> SEQUENCE: 6

```
Met Pro Lys Lys Lys Arg Lys Val Ser Arg Leu Asp Lys Ser Lys Val
1               5                   10                  15

Ile Asn Ser Ala Leu Glu Leu Leu Asn Glu Val Gly Ile Glu Gly Leu
            20                  25                  30

Thr Thr Arg Lys Leu Ala Gln Lys Leu Gly Val Glu Gln Pro Thr Leu
        35                  40                  45

Tyr Trp His Val Lys Asn Lys Arg Ala Leu Leu Asp Ala Leu Ala Ile
    50                  55                  60
```

```
Glu Met Leu Asp Arg His His Thr His Phe Cys Pro Leu Glu Gly Glu
 65                  70                  75                  80

Ser Trp Gln Asp Phe Leu Arg Asn Asn Ala Lys Ser Phe Arg Cys Ala
                 85                  90                  95

Leu Leu Ser His Arg Asp Gly Ala Lys Val His Leu Gly Thr Arg Pro
            100                 105                 110

Thr Glu Lys Gln Tyr Glu Thr Leu Glu Asn Gln Leu Ala Phe Leu Cys
        115                 120                 125

Gln Gln Gly Phe Ser Leu Glu Asn Ala Leu Tyr Ala Leu Ser Ala Val
130                 135                 140

Gly His Phe Thr Leu Gly Cys Val Leu Glu Asp Gln Glu His Gln Val
145                 150                 155                 160

Ala Lys Glu Glu Arg Glu Thr Pro Thr Thr Asp Ser Met Pro Pro Leu
                165                 170                 175

Leu Arg Gln Ala Ile Glu Leu Phe Asp His Gln Gly Ala Glu Pro Ala
            180                 185                 190

Phe Leu Phe Gly Leu Glu Leu Ile Ile Cys Gly Leu Glu Lys Gln Leu
        195                 200                 205

Lys Cys Glu Ser Gly Ser Pro Arg
    210                 215
```

<210> SEQ ID NO 7
<211> LENGTH: 20
<212> TYPE: DNA
<213> ORGANISM: Artificial Sequence
<220> FEATURE:
<223> OTHER INFORMATION: hROSA26 Locus PCR

<400> SEQUENCE: 7
gagaagaggc tgtgcttcgg                                        20

<210> SEQ ID NO 8
<211> LENGTH: 22
<212> TYPE: DNA
<213> ORGANISM: Artificial Sequence
<220> FEATURE:
<223> OTHER INFORMATION: hROSA26 Locus PCR

<400> SEQUENCE: 8
acagtacaag ccagtaatgg ag                                     22

<210> SEQ ID NO 9
<211> LENGTH: 20
<212> TYPE: DNA
<213> ORGANISM: Artificial Sequence
<220> FEATURE:
<223> OTHER INFORMATION: hROSA26 5'-INT PCR

<400> SEQUENCE: 9
gagaagaggc tgtgcttcgg                                        20

<210> SEQ ID NO 10
<211> LENGTH: 21
<212> TYPE: DNA
<213> ORGANISM: Artificial Sequence
<220> FEATURE:
<223> OTHER INFORMATION: hROSA26 5'-INT PCR

<400> SEQUENCE: 10
aagaccgcga agagtttgtc c                                      21

```
<210> SEQ ID NO 11
<211> LENGTH: 21
<212> TYPE: DNA
<213> ORGANISM: Artificial Sequence
<220> FEATURE:
<223> OTHER INFORMATION: hROSA26 3'-INT PCR

<400> SEQUENCE: 11
gaaactcgct caaaagctgg g                                              21

<210> SEQ ID NO 12
<211> LENGTH: 22
<212> TYPE: DNA
<213> ORGANISM: Artificial Sequence
<220> FEATURE:
<223> OTHER INFORMATION: hROSA26 3'-INT PCR

<400> SEQUENCE: 12
acagtacaag ccagtaatgg ag                                             22

<210> SEQ ID NO 13
<211> LENGTH: 21
<212> TYPE: DNA
<213> ORGANISM: Artificial Sequence
<220> FEATURE:
<223> OTHER INFORMATION: hROSA26 3'-BB PCR

<400> SEQUENCE: 13
gaaactcgct caaaagctgg g                                              21

<210> SEQ ID NO 14
<211> LENGTH: 20
<212> TYPE: DNA
<213> ORGANISM: Artificial Sequence
<220> FEATURE:
<223> OTHER INFORMATION: hROSA26 3'-BB PCR

<400> SEQUENCE: 14
tgaccatgat tacgccaagc                                                20

<210> SEQ ID NO 15
<211> LENGTH: 25
<212> TYPE: DNA
<213> ORGANISM: Artificial Sequence
<220> FEATURE:
<223> OTHER INFORMATION: AAVS1 Locus PCR

<400> SEQUENCE: 15
ctgtttcccc ttcccaggca ggtcc                                          25

<210> SEQ ID NO 16
<211> LENGTH: 25
<212> TYPE: DNA
<213> ORGANISM: Artificial Sequence
<220> FEATURE:
<223> OTHER INFORMATION: AAVS1 Locus PCR

<400> SEQUENCE: 16
tgcaggggaa cggggctcag tctga                                          25

<210> SEQ ID NO 17
<211> LENGTH: 25
<212> TYPE: DNA
<213> ORGANISM: Artificial Sequence
<220> FEATURE:
<223> OTHER INFORMATION: AAVS1 5'-INT PCR
```

<400> SEQUENCE: 17
ctgtttcccc ttcccaggca ggtcc                                              25

<210> SEQ ID NO 18
<211> LENGTH: 25
<212> TYPE: DNA
<213> ORGANISM: Artificial Sequence
<220> FEATURE:
<223> OTHER INFORMATION: AAVS1 5'-INT PCR

<400> SEQUENCE: 18
tcgtcgcggg tggcgaggcg caccg                                              25

<210> SEQ ID NO 19
<211> LENGTH: 25
<212> TYPE: DNA
<213> ORGANISM: Artificial Sequence
<220> FEATURE:
<223> OTHER INFORMATION: AAVS1 3'-INT PCR

<400> SEQUENCE: 19
tgcaggggaa cggggctcag tctga                                              25

<210> SEQ ID NO 20
<211> LENGTH: 20
<212> TYPE: DNA
<213> ORGANISM: Artificial Sequence
<220> FEATURE:
<223> OTHER INFORMATION: AAVS1 3'-BB PCR

<400> SEQUENCE: 20
atgcttccgg ctcgtatgtt                                                    20

<210> SEQ ID NO 21
<211> LENGTH: 22
<212> TYPE: DNA
<213> ORGANISM: Artificial Sequence
<220> FEATURE:
<223> OTHER INFORMATION: CNP Fw

<400> SEQUENCE: 21
tcctcatcat gaacagaggc tt                                                 22

<210> SEQ ID NO 22
<211> LENGTH: 20
<212> TYPE: DNA
<213> ORGANISM: Artificial Sequence
<220> FEATURE:
<223> OTHER INFORMATION: CNP Rev

<400> SEQUENCE: 22
aaactgcagc tcaggcttgt                                                    20

<210> SEQ ID NO 23
<211> LENGTH: 20
<212> TYPE: DNA
<213> ORGANISM: Artificial Sequence
<220> FEATURE:
<223> OTHER INFORMATION: DES Fw

<400> SEQUENCE: 23
ccaacaagaa caacgacgcc                                                    20

<210> SEQ ID NO 24
<211> LENGTH: 21

```
<212> TYPE: DNA
<213> ORGANISM: Artificial Sequence
<220> FEATURE:
<223> OTHER INFORMATION: DES Rev

<400> SEQUENCE: 24
atcagggaat cgttagtgcc c                                              21

<210> SEQ ID NO 25
<211> LENGTH: 22
<212> TYPE: DNA
<213> ORGANISM: Artificial Sequence
<220> FEATURE:
<223> OTHER INFORMATION: DMD Fw

<400> SEQUENCE: 25
tggtgggaag aagtagagga ct                                             22

<210> SEQ ID NO 26
<211> LENGTH: 20
<212> TYPE: DNA
<213> ORGANISM: Artificial Sequence
<220> FEATURE:
<223> OTHER INFORMATION: DMD Rev

<400> SEQUENCE: 26
tgctgcttcc caaacttaga                                                20

<210> SEQ ID NO 27
<211> LENGTH: 20
<212> TYPE: DNA
<213> ORGANISM: Artificial Sequence
<220> FEATURE:
<223> OTHER INFORMATION: EGFP Fw

<400> SEQUENCE: 27
cccgacaacc actacctgag                                                20

<210> SEQ ID NO 28
<211> LENGTH: 20
<212> TYPE: DNA
<213> ORGANISM: Artificial Sequence
<220> FEATURE:
<223> OTHER INFORMATION: EGFP Rev

<400> SEQUENCE: 28
gtccatgccg agagtgatcc                                                20

<210> SEQ ID NO 29
<211> LENGTH: 20
<212> TYPE: DNA
<213> ORGANISM: Artificial Sequence
<220> FEATURE:
<223> OTHER INFORMATION: FOXG1 Fw

<400> SEQUENCE: 29
tgccaagttt tacgacggga                                                20

<210> SEQ ID NO 30
<211> LENGTH: 20
<212> TYPE: DNA
<213> ORGANISM: Artificial Sequence
<220> FEATURE:
<223> OTHER INFORMATION: FOXG1 Rev

<400> SEQUENCE: 30
```
gggttggaag aagacccctg                                              20

<210> SEQ ID NO 31
<211> LENGTH: 20
<212> TYPE: DNA
<213> ORGANISM: Artificial Sequence
<220> FEATURE:
<223> OTHER INFORMATION: GRIA4 Fw

<400> SEQUENCE: 31
ggccagggaa ttgacatgga                                              20

<210> SEQ ID NO 32
<211> LENGTH: 23
<212> TYPE: DNA
<213> ORGANISM: Artificial Sequence
<220> FEATURE:
<223> OTHER INFORMATION: GRIA4 Rev

<400> SEQUENCE: 32 aaccaaccctt tctaggtcct gtg                                         23

<210> SEQ ID NO 33
<211> LENGTH: 20
<212> TYPE: DNA
<213> ORGANISM: Artificial Sequence
<220> FEATURE:
<223> OTHER INFORMATION: HMBS (PBGD) Fw

<400> SEQUENCE: 33
attaccccgg gagactgaac                                              20

<210> SEQ ID NO 34
<211> LENGTH: 20
<212> TYPE: DNA
<213> ORGANISM: Artificial Sequence
<220> FEATURE:
<223> OTHER INFORMATION: HMBS (PBGD) Rev

<400> SEQUENCE: 34
ggctgttgct tggacttctc                                              20

<210> SEQ ID NO 35
<211> LENGTH: 20
<212> TYPE: DNA
<213> ORGANISM: Artificial Sequence
<220> FEATURE:
<223> OTHER INFORMATION: MAG Fw

<400> SEQUENCE: 35
cagaagacgt ccccaactca                                              20

<210> SEQ ID NO 36
<211> LENGTH: 22
<212> TYPE: DNA
<213> ORGANISM: Artificial Sequence
<220> FEATURE:
<223> OTHER INFORMATION: MAG Rev

<400> SEQUENCE: 36
cctcgggagg ctgaaatcat aa                                           22

<210> SEQ ID NO 37
<211> LENGTH: 21
<212> TYPE: DNA
<213> ORGANISM: Artificial Sequence

```
<220> FEATURE:
<223> OTHER INFORMATION: MAP2 Fw

<400> SEQUENCE: 37
agactgcagc tctgccttta g                                        21

<210> SEQ ID NO 38
<211> LENGTH: 23
<212> TYPE: DNA
<213> ORGANISM: Artificial Sequence
<220> FEATURE:
<223> OTHER INFORMATION: MAP2 Rev

<400> SEQUENCE: 38
aggctgtaag taaatcttcc tcc                                      23

<210> SEQ ID NO 39
<211> LENGTH: 24
<212> TYPE: DNA
<213> ORGANISM: Artificial Sequence
<220> FEATURE:
<223> OTHER INFORMATION: MBP Fw

<400> SEQUENCE: 39
tggtgatgga gatgtcaagc aggt                                     24

<210> SEQ ID NO 40
<211> LENGTH: 24
<212> TYPE: DNA
<213> ORGANISM: Artificial Sequence
<220> FEATURE:
<223> OTHER INFORMATION: MBP Rev

<400> SEQUENCE: 40
gctgtggttt ggaaacgagg ttgt                                     24

<210> SEQ ID NO 41
<211> LENGTH: 23
<212> TYPE: DNA
<213> ORGANISM: Artificial Sequence
<220> FEATURE:
<223> OTHER INFORMATION: MOG Fw

<400> SEQUENCE: 41
agagatagag aatctccacc gga                                      23

<210> SEQ ID NO 42
<211> LENGTH: 21
<212> TYPE: DNA
<213> ORGANISM: Artificial Sequence
<220> FEATURE:
<223> OTHER INFORMATION: MOG Rev

<400> SEQUENCE: 42
tgatcaaggc aaccaagggt c                                        21

<210> SEQ ID NO 43
<211> LENGTH: 22
<212> TYPE: DNA
<213> ORGANISM: Artificial Sequence
<220> FEATURE:
<223> OTHER INFORMATION: MYH1 Fw

<400> SEQUENCE: 43
cacactagtt tcacagctct cg                                       22
```

<210> SEQ ID NO 44
<211> LENGTH: 20
<212> TYPE: DNA
<213> ORGANISM: Artificial Sequence
<220> FEATURE:
<223> OTHER INFORMATION: MYH1 Rev

<400> SEQUENCE: 44
cagggcactc ttggccttta					20

<210> SEQ ID NO 45
<211> LENGTH: 21
<212> TYPE: DNA
<213> ORGANISM: Artificial Sequence
<220> FEATURE:
<223> OTHER INFORMATION: MYH2 Fw

<400> SEQUENCE: 45
ggaagctctg gtgtctcagt t					21

<210> SEQ ID NO 46
<211> LENGTH: 21
<212> TYPE: DNA
<213> ORGANISM: Artificial Sequence
<220> FEATURE:
<223> OTHER INFORMATION: MYH2 Rev

<400> SEQUENCE: 46
cagggcgttc ttggcttttta t				21

<210> SEQ ID NO 47
<211> LENGTH: 20
<212> TYPE: DNA
<213> ORGANISM: Artificial Sequence
<220> FEATURE:
<223> OTHER INFORMATION: MYH3 Fw

<400> SEQUENCE: 47
gctgcatacc cagaacacca					20

<210> SEQ ID NO 48
<211> LENGTH: 20
<212> TYPE: DNA
<213> ORGANISM: Artificial Sequence
<220> FEATURE:
<223> OTHER INFORMATION: MYH3 Rev

<400> SEQUENCE: 48
ccctgctggc atcttctacc					20

<210> SEQ ID NO 49
<211> LENGTH: 20
<212> TYPE: DNA
<213> ORGANISM: Artificial Sequence
<220> FEATURE:
<223> OTHER INFORMATION: MYH4 Fw

<400> SEQUENCE: 49
tcgcatttgt cagccaaggg					20

<210> SEQ ID NO 50
<211> LENGTH: 21
<212> TYPE: DNA
<213> ORGANISM: Artificial Sequence
<220> FEATURE:
<223> OTHER INFORMATION: MYH4 Rev

```
<400> SEQUENCE: 50
tgaaacccag gatgtccaca g                                              21

<210> SEQ ID NO 51
<211> LENGTH: 20
<212> TYPE: DNA
<213> ORGANISM: Artificial Sequence
<220> FEATURE:
<223> OTHER INFORMATION: MYH7 Fw

<400> SEQUENCE: 51
gagactgtcg tgggcttgta                                                20

<210> SEQ ID NO 52
<211> LENGTH: 21
<212> TYPE: DNA
<213> ORGANISM: Artificial Sequence
<220> FEATURE:
<223> OTHER INFORMATION: MYH7 Rev

<400> SEQUENCE: 52
gcccttctca ataggcgcat c                                              21

<210> SEQ ID NO 53
<211> LENGTH: 20
<212> TYPE: DNA
<213> ORGANISM: Artificial Sequence
<220> FEATURE:
<223> OTHER INFORMATION: MYH8 Fw

<400> SEQUENCE: 53
tgaagcagat agcagcgcga                                                20

<210> SEQ ID NO 54
<211> LENGTH: 20
<212> TYPE: DNA
<213> ORGANISM: Artificial Sequence
<220> FEATURE:
<223> OTHER INFORMATION: MYH8 Rev

<400> SEQUENCE: 54
cgtacgaagt gagggtgtgt                                                20

<210> SEQ ID NO 55
<211> LENGTH: 20
<212> TYPE: DNA
<213> ORGANISM: Artificial Sequence
<220> FEATURE:
<223> OTHER INFORMATION: MYOD1 (endo) Fw

<400> SEQUENCE: 55
gccgctttcc ttaaccacaa                                                20

<210> SEQ ID NO 56
<211> LENGTH: 20
<212> TYPE: DNA
<213> ORGANISM: Artificial Sequence
<220> FEATURE:
<223> OTHER INFORMATION: MYOD1 (endo) Rev

<400> SEQUENCE: 56
ctgaatgccc acccactgtc                                                20

<210> SEQ ID NO 57
```

```
<211> LENGTH: 20
<212> TYPE: DNA
<213> ORGANISM: Artificial Sequence
<220> FEATURE:
<223> OTHER INFORMATION: MYOD1 Fw

<400> SEQUENCE: 57
cgacggcatg atggactaca                                                   20

<210> SEQ ID NO 58
<211> LENGTH: 20
<212> TYPE: DNA
<213> ORGANISM: Artificial Sequence
<220> FEATURE:
<223> OTHER INFORMATION: MYOD1 Rev

<400> SEQUENCE: 58
tagtaggcgc cttcgtagca                                                   20

<210> SEQ ID NO 59
<211> LENGTH: 22
<212> TYPE: DNA
<213> ORGANISM: Artificial Sequence
<220> FEATURE:
<223> OTHER INFORMATION: NANOG Fw

<400> SEQUENCE: 59
agcagatgca agaactctcc aa                                                22

<210> SEQ ID NO 60
<211> LENGTH: 20
<212> TYPE: DNA
<213> ORGANISM: Artificial Sequence
<220> FEATURE:
<223> OTHER INFORMATION: NANOG Rev

<400> SEQUENCE: 60
tgaggccttc tgcgtcacac                                                   20

<210> SEQ ID NO 61
<211> LENGTH: 21
<212> TYPE: DNA
<213> ORGANISM: Artificial Sequence
<220> FEATURE:
<223> OTHER INFORMATION: NEUROG2 (NGN2) Fw

<400> SEQUENCE: 61
tgttcgtcaa atccgagacc t                                                 21

<210> SEQ ID NO 62
<211> LENGTH: 20
<212> TYPE: DNA
<213> ORGANISM: Artificial Sequence
<220> FEATURE:
<223> OTHER INFORMATION: NEUROG2 (NGN2) Rev

<400> SEQUENCE: 62
cgatccgagc agcactaaca                                                   20

<210> SEQ ID NO 63
<211> LENGTH: 20
<212> TYPE: DNA
<213> ORGANISM: Artificial Sequence
<220> FEATURE:
<223> OTHER INFORMATION: PAX6 Fw

<400> SEQUENCE: 63
```

```
cgagatttca gagccccata                                            20

<210> SEQ ID NO 64
<211> LENGTH: 20
<212> TYPE: DNA
<213> ORGANISM: Artificial Sequence
<220> FEATURE:
<223> OTHER INFORMATION: PAX6 Rev

<400> SEQUENCE: 64
aagacaccac cgagctgatt                                            20

<210> SEQ ID NO 65
<211> LENGTH: 22
<212> TYPE: DNA
<213> ORGANISM: Artificial Sequence
<220> FEATURE:
<223> OTHER INFORMATION: PLP Fw

<400> SEQUENCE: 65
aacagctgag ttccaaatga cc                                         22

<210> SEQ ID NO 66
<211> LENGTH: 20
<212> TYPE: DNA
<213> ORGANISM: Artificial Sequence
<220> FEATURE:
<223> OTHER INFORMATION: PLP Rev

<400> SEQUENCE: 66
acggcaaagt tgtaagtggc                                            20

<210> SEQ ID NO 67
<211> LENGTH: 20
<212> TYPE: DNA
<213> ORGANISM: Artificial Sequence
<220> FEATURE:
<223> OTHER INFORMATION: POU3F2 (BRN2) Fw

<400> SEQUENCE: 67
acccgcttta tcgaaggcaa                                            20

<210> SEQ ID NO 68
<211> LENGTH: 20
<212> TYPE: DNA
<213> ORGANISM: Artificial Sequence
<220> FEATURE:
<223> OTHER INFORMATION: POU3F2 (BRN2) Rev

<400> SEQUENCE: 68
cctccataac ctcccccaga                                            20

<210> SEQ ID NO 69
<211> LENGTH: 20
<212> TYPE: DNA
<213> ORGANISM: Artificial Sequence
<220> FEATURE:
<223> OTHER INFORMATION: POU5F1 (OCT4) Fw

<400> SEQUENCE: 69
gtggaggaag ctgacaacaa                                            20

<210> SEQ ID NO 70
<211> LENGTH: 20
<212> TYPE: DNA
```

```
<213> ORGANISM: Artificial Sequence
<220> FEATURE:
<223> OTHER INFORMATION: POU5F1 (OCT4) Rev

<400> SEQUENCE: 70
attctccagg ttgcctctca                                                   20

<210> SEQ ID NO 71
<211> LENGTH: 20
<212> TYPE: DNA
<213> ORGANISM: Artificial Sequence
<220> FEATURE:
<223> OTHER INFORMATION: RYR1 Fw

<400> SEQUENCE: 71
caatcgccag aacggagaga                                                   20

<210> SEQ ID NO 72
<211> LENGTH: 20
<212> TYPE: DNA
<213> ORGANISM: Artificial Sequence
<220> FEATURE:
<223> OTHER INFORMATION: RYR1 Rev

<400> SEQUENCE: 72
gtcgtgttcc ctgtctgtgt                                                   20

<210> SEQ ID NO 73
<211> LENGTH: 20
<212> TYPE: DNA
<213> ORGANISM: Artificial Sequence
<220> FEATURE:
<223> OTHER INFORMATION: SLC17A6 (VGLUT2) Fw

<400> SEQUENCE: 73
gtagactggc aaccacctcc                                                   20

<210> SEQ ID NO 74
<211> LENGTH: 22
<212> TYPE: DNA
<213> ORGANISM: Artificial Sequence
<220> FEATURE:
<223> OTHER INFORMATION: SLC17A6 (VGLUT2) Rev

<400> SEQUENCE: 74
ccattccaaa gcttccgtag ac                                                22

<210> SEQ ID NO 75
<211> LENGTH: 22
<212> TYPE: DNA
<213> ORGANISM: Artificial Sequence
<220> FEATURE:
<223> OTHER INFORMATION: SYP Fw

<400> SEQUENCE: 75
acctcgggac tcaacacctc gg                                                22

<210> SEQ ID NO 76
<211> LENGTH: 22
<212> TYPE: DNA
<213> ORGANISM: Artificial Sequence
<220> FEATURE:
<223> OTHER INFORMATION: SYP Rev

<400> SEQUENCE: 76
gaaccacagg ttgccgaccc ag                                                22
```

```
<210> SEQ ID NO 77
<211> LENGTH: 20
<212> TYPE: DNA
<213> ORGANISM: Artificial Sequence
<220> FEATURE:
<223> OTHER INFORMATION: SYN1 Fw

<400> SEQUENCE: 77
ccctgggtgt ttgcccagat                                               20

<210> SEQ ID NO 78
<211> LENGTH: 20
<212> TYPE: DNA
<213> ORGANISM: Artificial Sequence
<220> FEATURE:
<223> OTHER INFORMATION: SYN1 Rev

<400> SEQUENCE: 78
accacggggt acgttgtact                                               20

<210> SEQ ID NO 79
<211> LENGTH: 21
<212> TYPE: DNA
<213> ORGANISM: Artificial Sequence
<220> FEATURE:
<223> OTHER INFORMATION: TUBB3 Fw

<400> SEQUENCE: 79
caaccagatc ggggccaagt t                                             21

<210> SEQ ID NO 80
<211> LENGTH: 19
<212> TYPE: DNA
<213> ORGANISM: Artificial Sequence
<220> FEATURE:
<223> OTHER INFORMATION: TUBB3 Rev

<400> SEQUENCE: 80
ccgagtcgcc cacgtagtt                                                19

<210> SEQ ID NO 81
<211> LENGTH: 52
<212> TYPE: DNA
<213> ORGANISM: Artificial Sequence
<220> FEATURE:
<223> OTHER INFORMATION: AAVS1 targeting vector Fw

<400> SEQUENCE: 81
gtgatagaga tccctggtgc aggtggactg actcacctgc acctgtttta ga           52

<210> SEQ ID NO 82
<211> LENGTH: 52
<212> TYPE: DNA
<213> ORGANISM: Artificial Sequence
<220> FEATURE:
<223> OTHER INFORMATION: AAVSI targeting vector Rev

<400> SEQUENCE: 82
actaaaacag gtgcaggtga gtcagtccac ctgcaccagg gatctctatc ac           52

<210> SEQ ID NO 83
<211> LENGTH: 24
<212> TYPE: DNA
<213> ORGANISM: Artificial Sequence
<220> FEATURE:
```

```
<223> OTHER INFORMATION: 20 bp tracer Fw
<220> FEATURE:
<221> NAME/KEY: modified_base
<222> LOCATION: (5)..(24)
<223> OTHER INFORMATION: a, g, c, t, unknown or other

<400> SEQUENCE: 83
tcccnnnnnn nnnnnnnnnn nnnn                                           24

<210> SEQ ID NO 84
<211> LENGTH: 24
<212> TYPE: DNA
<213> ORGANISM: Artificial Sequence
<220> FEATURE:
<223> OTHER INFORMATION: 20bp tracer Rev
<220> FEATURE:
<221> NAME/KEY: modified_base
<222> LOCATION: (5)..(24)
<223> OTHER INFORMATION: a, g, c, t, unknown or other

<400> SEQUENCE: 84
aaacnnnnnn nnnnnnnnnn nnnn                                           24

<210> SEQ ID NO 85
<211> LENGTH: 268
<212> TYPE: DNA
<213> ORGANISM: Artificial Sequence
<220> FEATURE:
<223> OTHER INFORMATION: H1 POLIII Promoter H1-TO

<400> SEQUENCE: 85
cgaacgctga cgtcatcaac ccgctccaag gaatcgcggg cccagtgtca ctaggcggga    60
acacccagcg cgcgtgcgcc ctggcaggaa gatggctgtg agggacaggg gagtggcgcc   120
ctgcaatatt tgcatgtcgc tatgtgttct gggaaatcac cataaacgtg aaatgtcttt   180
ggatttggga atcttataag ttccctatca gtgatagaga tccctggtgc aggtggactg   240
actcacctgc acctgtttta gagctaga                                      268

<210> SEQ ID NO 86
<211> LENGTH: 268
<212> TYPE: DNA
<213> ORGANISM: Artificial Sequence
<220> FEATURE:
<223> OTHER INFORMATION: H1 POLIII Promoter H1-2TO

<400> SEQUENCE: 86
cgaacgctga cgtcatcaac ccgctccaag gaatcgcggg cccagtgtca ctaggcggga    60
acacccagcg cgcgtgcgcc ctggcaggaa gatggctgtg agggacaggg gagtggcgcc   120
ctgcaatatt tgcatgtcgc tatgtgttct gggaaatcac cataaacgtg aaatccctat   180
cagtgataga gacttataag ttccctatca gtgatagaga tccctggtgc aggtggactg   240
actcacctgc acctgtttta gagctaga                                      268

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 87
gtcgagtcgc ttctcgatta tgg                                            23
```

```
<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 88
ggcgatgacg agatcacgcg agg                                           23
```

CONTROLLABLE TRANSCRIPTION

CROSS-REFERENCE TO RELATED APPLICATIONS

This application is a U.S. National Phase Application under 35 U.S.C. § 371 of International Application No. PCT/GB2017/053531, with an International Filing Date of Nov. 24, 2017, which claims priority to GB Patent Application No. 1619876.4 filed on Nov. 24, 2016, each of which are hereby incorporated by reference in its entirety.

REFERENCE TO A SEQUENCE LISTING

This application contains a Sequence Listing in computer readable form. The computer readable form is incorporated herein by reference. Said ASCII copy, created on Aug. 12, 2022, is named BBIO-001WOUS_SL.txt and is 24,234 bytes in size.

The present invention relates to a stable method for introducing at least one inducible cassette into a cell, and permitting controllable transcription from within that inducible cassette. The method may be used for any cell type, from any eukaryotic organism, but has a particular application in the introduction of inducible cassettes into pluripotent stem cells, such as animal or human pluripotent stem cells (hPSCs). The inducible cassette is controllably inserted in such a way to ensure that the genetic material it contains is not silenced or subject to negative influences from the insertion site, and transcription of the genetic material is controlled.

BACKGROUND TO THE INVENTION

Stem cell research holds great promise for research of human development, regenerative medicine, disease modelling, drug discovery, and cell transplantation. Moreover, stem cell-derived cells enable studying physiological and pathological responses of human cell populations that are not easily accessible. This often entails the study of genes (and other forms of regulatory mechanisms encoded in non-protein-coding RNAs—ncRNAs). Unfortunately, controllable transcription or expression of genetic information in human cells has been proven to be particularly difficult.

Moreover, for several key aspects of regenerative medicine, disease modelling, drug discovery and cell transplantation, manipulation and manufacture of mature human cell types from easily accessible sources is required. Controlling the expression of transgenes in human cells is the basis of biological research. However, this has proven to be difficult in human cells. Moreover, there is a real need for the in vitro derivation of many highly desirable human cell types in a quantity and quality suitable for drug discovery and regenerative medicine purposes. Because directed differentiation of stem cells into desired cell types is often challenging, other approaches have emerged, including direct reprogramming of cells into the desired cell types. In particular, forward programming, as a method of directly converting pluripotent stem cells, including hPSCs, to mature cell types has been recognised as a powerful strategy for the derivation of human cells. This reprogramming involves the forced expression of key lineage transcription factors (or non-coding RNAs, including lncRNA and microRNA) in order to convert the stem cell into a particular mature cell type. Also in this context, controllable expression of genetic information in human cells has been challenging. Currently available forward programming protocols are largely based on lentiviral transduction of cells, which results in variegated expression or complete silencing of randomly inserted inducible cassettes. This results in additional purification steps in order to isolate a sub-population expressing the required transcription factors. Thus, further refinements of these methods are clearly required.

Apart from inducible expression of transgenes, it is very desirable to be able to control knockdown and knockout of genes or other coding sequences in cells, to allow loss of function studies to be carried out. Loss of function studies in stem cells and mature cell types provide a unique opportunity to study the mechanisms that regulate human development, disease and physiology. However, current techniques do not permit the easy and efficient manipulation of gene expression. The current techniques to introduce material such as inducible short hairpin RNAs (shRNA) into stem cells to trigger gene knockdown suffer from many of the drawbacks seen with the forward reprogramming discussed above, such as transgene silencing and positional effects limiting activity. Thus, there is a need for inducible gene knockout and knockdown in stem cells that allows for loss of function studies in stem cells.

Any refinements to the above methods must ensure that stable transcription of the genetic material contained within the inducible cassette, such as a transgene, is achieved which is resistant to silencing and other negative integration site-related influences. Silencing may be caused by multiple epigenetic mechanisms, including DNA methylation or histone modifications. With prior art methods based on lentiviral transduction, the cells obtained are a heterogeneous population with the transgene expressed fully, partially or silenced. Clearly, this is not desirable for many applications. Viral vectors demonstrate a tendency to integrate their genetic material into transcriptionally active areas of the genome, thus increasing the potential for oncogenic events due to insertional mutagenesis.

For many applications, it is desirable to control the transcription of inserted genetic material in a cell, such that an inducible cassette may be turned on as required and transcribed at particular levels, including high levels. This cannot be achieved if the insertion of the inducible cassette is random in the genome.

The inventors have thus developed a method for enabling the stable introduction of an inducible cassette into the genome of a cell, whilst being able to control the transcription of that inducible cassette. This has benefits in any cell type in which it is desired to introduce an inducible cassette and control transcription of the inserted genetic material, in particular in pluripotent stem cells. The inducible cassette may include any genetic material capable of transcription, for example a transgene or a non-coding RNA (ncRNA). The material included within the inducible cassette will be determined by what effects are required from the stem cell, including expression of a transgene or gene knockdown or knockout.

SUMMARY OF THE INVENTION

The inventors have found that it is possible to insert an inducible cassette and control transcription of the genetic material within that inducible cassette by using a dual genomic safe harbour targeted system herein described. Such a method is highly desirable, since there is reduced risk of epigenetic silencing of the inserted genetic material, and it is possible to obtain a homogenous population of cells transcribing the inducible cassette.

The present invention thus relates to a method for controlling the transcription of a genetic sequence in a cell, comprising the following steps:

a) targeted insertion of a gene encoding a transcriptional regulator protein into a first genetic safe harbour site; and b) targeted insertion of an inducible cassette into a second genetic safe harbour site, wherein said inducible cassette comprises said genetic sequence operably linked to an inducible promoter and said promoter is regulated by the transcriptional regulator protein;

wherein said first and second genetic safe harbour sites are different.

Inducible cassette integration specifically into genomic safe harbour sites (GSHs) is preferred over random insertion into the genome. GSHs have been defined previously as "intragenic or extragenic regions of the human genome that are able to accommodate the predictable expression of newly integrated DNA without adverse effects on the host cell or organism. A useful safe harbour must permit sufficient transcription of the inserted genetic sequence to yield desired levels of the protein (via further translation) or non-coding RNA. A GSH also must not predispose cells to malignant transformation nor alter cellular functions" (Sadelain et al., 2012, Nature Reviews Cancer, 12(1), 51-8. doi:10.1038/nrc3179).

The first genetic safe harbour site is utilised to introduce a gene encoding at least a transcriptional regulator protein. A transcriptional regulator protein (or transcription factor) increases gene transcription of a gene. Most transcriptional regulators are DNA-binding proteins that bind to enhancers or promoter-proximal elements operably linked to the gene.

In some aspects, the transcriptional regulator protein is constitutively expressed, and is permanently expressed in a cell. The transcriptional regulator protein may thus be operably linked to a constitutive promoter. Constitutive promoters direct gene expression uniformly in most tissues and cells at all stages of growth and development. Constitutive promoters confer high levels of gene expression when used in the methods of the present invention.

Further genetic material including genes may be inserted into the first GSH with the transcriptional regulator protein. Such genes may include one or more markers such as green fluorescent protein (GFP) which can be used to show, for example, that the transcriptional regulator protein has been successfully inserted. Other options include genes that allow gene editing, for example Cas9 and derivatives or CasL and derivatives, and reporter sequences that can be used to assay endogenous or exogenous expression of specific genes in the cell.

The second GSH is utilised to introduce an inducible cassette in which the desired genetic sequence is operably linked to an inducible promoter. Such a promoter enables transcription only when correctly induced by the transcriptional regulator protein. The transcriptional regulator protein may be controlled by a substance which is exogenously supplied to the cell. Thus, the presence of the exogenous substance may permit or block expression from the inducible promoter. An example of such controllable expression is the Tet-ON system which is described further herein.

Further inducible cassette(s) may be inserted into further GSHs, said GSHs are distinct from the first and second GSH mentioned above.

One or more genetic sequences may be controllably transcribed from within the second and/or further GSH. Indeed, the inducible cassette may contain 1, 2, 3, 4, 5, 6, 7, 8, 9 or 10 genetic sequences which it is desired to insert into the GSH and the transcription of which be controllably induced.

The genetic sequence or sequences which it is desired to insert into the GSH or GSHs are present within the inducible cassette, operably linked to an inducible promoter. These genetic sequences can be any suitable sequence, which are capable of being transcribed into RNA once the activity of the promoter has been induced. Suitable genetic sequences include but are not limited to transgenes (protein coding genes, in which the RNA produced is messenger RNA (mRNA) is translated into a polypeptide), non-coding RNA (ncRNA—including but not limited to shRNA, antisense RNA (asRNA), guide RNA (gRNA), microRNA (miRNA), small interfering RNA (siRNA), trans-acting RNA (ta-siRNA), antagomirs, aptamers, miRNA sponges, and any other functional RNA).

The inducible cassettes may include additional genetic material to be inserted into the second or further GSH. Such additional genetic material may include one or markers such as green fluorescent protein (GFP) to indicate that the transcription is occurring. Alternatively, or additionally, genes such as antibiotic or drug resistance genes may allow for selection of successfully inserted inducible cassettes. Moreover, the inducible expression of a particular gene to study its function or of sequences that will interfere with its function may be desirable. Equally, expression of genes to enhance or obstruct biological functions of the cell or influencing cells in other part of the organism may be desirable, including the expression of growth factors, peptide hormones, including insulin etc.

Technically, the insertions into the first and/or second GSH may occur on one chromosome, or on both chromosomes. The GSH exists at the same genetic loci on both chromosomes of diploid organisms. Insertion within both chromosomes is advantageous since it may enable an increase in the level of transcription from the inserted genetic material within the inducible cassette, thus achieving particularly high levels of transcription.

The insertions into the GSHs may be controlled Specific insertion of genetic material into the particular GSH based upon customised site-specific generation of DNA double-strand breaks (DSB) at the GSH may be achieved. The genetic material may then be introduced using any suitable mechanism, such as homologous recombination. Any method of making a specific DSB in the genome may be used, but preferred systems include CRISPR/Cas9 and modified versions thereof, ZFNs and the TALEN system.

Furthermore, the insertion of the transcriptional regulator and/or inducible cassette can be designed to be reversible and the inserted genetic material may be removed and/or replaced with and alternative transcriptional regulator/inducible cassette as appropriate. Methods of replacing the transcriptional regulator and/or inducible cassette form part of the invention. Such replacement may be useful where a culture of cells has been modified successfully with one transcriptional regulator and/or one inducible cassette, and it is desirable to replace the transcriptional regulator and/or inducible cassette. This takes advantage of the already successful insertion and may allow for larger insertions to be made. In order to perform this aspect of the invention, the insertions may include cleavable sequences to allow for the removal of all or part of the insertion from the GSH, such as a portion of the insertion. Preferred methods of removal or replacement include recombinational approaches.

Further, the invention relates to the vectors suitable for insertion of the transcriptional regulator and/or inducible cassette into the GSH.

In one aspect, the present invention provides a method for controlling the expression of a transgene in a cell, comprising the following steps:
 a) targeted insertion of a gene encoding a transcriptional regulator protein into a first genetic safe harbour site; and
 b) targeted insertion of a transgene operably linked to an inducible promoter into a second genetic safe harbour site, wherein said inducible promoter is regulated by the transcriptional regulator protein;
 wherein said first and second genetic safe harbour sites are different.

In this aspect of the invention, the inducible cassette described previously comprises a transgene operably linked to an inducible promoter. In this aspect of the invention, the desired genetic sequence included within the inducible cassette is a transgene, preferably a protein-encoding gene. Thus, the transcription and translation (expression) of the transgene may be controlled within the cell. The advantage of the present method is that it permits overexpression of the transgene, if required.

Further, in this aspect of the invention, a further identical or different transgene may be inserted into a further GSH, which is different to the first and second GSH. Such a transgene is operably linked to an inducible promoter as described above.

In one aspect, the present invention provides a method for controlling the transcription of a non-coding RNA in a cell, comprising the following steps:
 a) targeted insertion of a gene encoding a transcriptional regulator protein into a first genetic safe harbour site; and
 b) targeted insertion of an inducible cassette into a second genetic safe harbour site, wherein said inducible cassette comprises DNA encoding a non-coding RNA sequence operably linked to an inducible promoter and said promoter is regulated by the transcriptional regulator protein;
 wherein said first and second genetic safe harbour sites are different.

Further, in this aspect of the invention, a further identical or different inducible cassette may be inserted into a further GSH, which is different to the first and second GSH. Such an inducible cassette may comprise DNA encoding a non-coding RNA sequence or any other genetic sequence operably linked to an inducible promoter and said promoter is regulated by the transcriptional regulator protein.

More particularly, this method allows for the knockdown of an endogenous gene in the cell. Thus, the present invention provides a method for reducing the transcription and/or translation of an endogenous gene in a cell, comprising the following steps:
 a) targeted insertion of a gene encoding a transcriptional regulator protein into a first genetic safe harbour site; and
 b) targeted insertion of an inducible cassette into a second genetic safe harbour site, wherein said inducible cassette comprises DNA encoding a non-coding RNA sequence operably linked to an inducible promoter and said promoter is regulated by the transcriptional regulator protein and wherein said non-coding RNA sequence suppresses the transcription or translation of an endogenous gene;
 wherein said first and second genetic safe harbour sites are different.

Further, in this aspect of the invention, a further identical or different inducible cassette may be inserted into a further GSH, which is different to the first and second GSH. Such an inducible cassette may comprise DNA encoding a non-coding RNA sequence or any other genetic sequence operably linked to an inducible promoter and said promoter is regulated by the transcriptional regulator protein.

In any aspect or embodiment, the endogenous gene may encode a protein or a non-coding RNA.

In the above two aspects of the invention, the inducible cassette(s) comprises a DNA encoding a non-coding RNA, i.e. an RNA which is functional but is not translated into protein. This non-coding RNA may be any suitable RNA, such as those discussed previously, but is preferably short hairpin RNA (shRNA). In the latter aspect of the invention, the non-coding RNA may effect gene knockdown in any suitable way, by blocking gene transcription or translation or preventing expression in general. Ultimately, the expression of said gene is reduced or blocked, but the gene itself remains intact.

Alternatively, the non-coding RNA comprised within the sequence of the inducible cassette may include RNAs which can be used to knockout an endogenous gene in a cell, notably to replace or disrupt the gene itself. Suitable non-coding RNAs that could be used for this aspect of the invention include elements of the CRISPR/Cas9 platform, more particularly the guide RNAs (gRNA) that are directed to target the endogenous gene.

Thus, in one aspect, the present invention provides a method for knocking out of an endogenous gene in a cell, comprising the following steps:
 a) targeted insertion of a gene encoding a transcriptional regulator protein and a gene encoding Cas9 or a derivative thereof into a first genetic safe harbour site; and
 b) targeted insertion of an inducible cassette into a second genetic safe harbour site, wherein said inducible cassette comprises a guide RNA operably linked to an inducible promoter and said promoter is regulated by the transcriptional regulator protein and wherein said gRNA sequence targets the endogenous gene;
 wherein said first and second genetic safe harbour sites are different.

Further, in this aspect of the invention, a further identical or different inducible cassette may be inserted into a further GSH, which is different to the first and second GSH. Such an inducible cassette may comprise any genetic sequence operably linked to an inducible promoter and said promoter is regulated by the transcriptional regulator protein.

Thus, in the above aspect of the invention, the transcription of the gRNA is controllably induced.

In a further aspect, the present invention provides a method for reducing the transcription and/or translation of an endogenous gene in a cell, comprising the following steps:
 a) targeted insertion of a gene encoding a transcriptional regulator protein into a first allele of a genetic safe harbour site; and
 b) targeted insertion of an inducible cassette into a second allele of the same genetic safe harbour site, wherein said inducible cassette comprises DNA encoding a non-coding RNA sequence operably linked to an inducible promoter and said promoter is regulated by the transcriptional regulator protein and wherein said non-coding RNA sequence suppresses the transcription or translation of an endogenous gene.

Further, the present invention provides a method for knocking out of an endogenous gene in a cell, comprising the following steps:
- a) targeted insertion of a gene encoding a transcriptional regulator protein and a gene encoding Cas9 or a derivative thereof into a first allele of a genetic safe harbour site; and
- b) targeted insertion of an inducible cassette into a second allele of the same genetic safe harbour site, wherein said inducible cassette comprises a guide RNA operably linked to an inducible promoter and said promoter is regulated by the transcriptional regulator protein and wherein said gRNA sequence targets the endogenous gene.

Such single-step knock-outs or knock downs are new and may form part of the invention.

In one aspect, the present invention provides a method for the forward programming of pluripotent stem cells, comprising the steps of:
- a) targeted insertion of a gene encoding a transcriptional regulator protein into a first genetic safe harbour site; and
- b) targeted insertion of an inducible cassette into a second genetic safe harbour site, wherein said inducible cassette comprises a genetic sequence encoding a key lineage transcription factor operably linked to an inducible promoter, said inducible promoter is regulated by the transcriptional regulator protein; and wherein said first and second genetic safe harbour sites are different.

Further or additional inducible cassette(s) may be inserted into further GSHs distinct from the first and second GSH.

The forward programming of pluripotent stem cells into particular mature cell types is highly desirable and can be achieved using the dual-targeting platform of the present invention. Particular methods for certain cell types are described below.

In one aspect, the present invention provides a method for the production of myocytes from pluripotent stem cells, comprising the steps of:
- a) targeted insertion of a gene encoding a transcriptional regulator protein into a first genetic safe harbour site; and
- b) targeted insertion of the MYOD1 gene operably linked to an inducible promoter into a second genetic safe harbour site, wherein said inducible promoter is regulated by the transcriptional regulator protein; wherein said first and second genetic safe harbour sites are different, and culturing said cells in the presence of retinoic acid.

The MYOD1 gene is the gene encoding the Myogenic Differentiation 1 protein. Preferably, the retinoic acid (RA) is all-trans RA.

In another aspect, the present invention provides a method for the production of myocytes from pluripotent stem cells expressing MYOD1, comprising culturing said cells in the presence of retinoic acid.

Preferably, the RA is all-trans RA. Preferably, the cells are overexpressing MYOD1.

In a further aspect, the present invention provides a method for the production of oligodendrocytes from pluripotent stem cells, comprising the steps of:
- a) targeted insertion of a gene encoding a transcriptional regulator protein into a first genetic safe harbour site; and
- b) targeted insertion of any combination of the SOX 10, OLIG2, NKX2.2, AND NKX6.2 genes operably linked to an inducible promoter into a second genetic safe harbour site, wherein said inducible promoter is regulated by the transcriptional regulator protein; wherein said first and second genetic safe harbour sites are different, The SOX-10, OLIG2, NKX2.2, NKX6.2 genes encode the transcription factor SOX-10, OLIG2, NKX2.2, AND NKX6.2, respectively.

DESCRIPTION OF FIGURES

FIG. 1(a) Design of the gene targeting vectors for the hROSA26 and AAVS1 loci. HAR: homology arm, SA: splice acceptor, T2A: T2A ribosomal skipping signal; Neo: neomycin resistance gene; Puro: puromycin resistance gene. pA: polyadenylation signal; CAG: constitutively active CAG promoter; rtTA: third generation rtTA; TRE: inducible Tet-Responsive Element; EGFP: enhanced green fluorescent protein. FIG. 1(b) shows EGFP induction and rescue kinetics (1(c)) in EGFP expressing hESCs detected by flow cytometry (median fluorescence intensity, MFI). Results are from two biological replicates per time point and are expressed as mean±SEM. All values were normalized to the maximum fluorescence intensity after 5 days of doxycycline (referred to as day 0 in the figure). FIG. 1(d) shows Doxycycline dose-response for EGFP overexpression in EGFP expressing hESCs following induction with doxycycline for 5 days. Results are from two biological replicates per condition, and are expressed as mean±SEM. All values were normalized to the maximum fluorescence intensity measured in the experiment. EGFP expression levels in GSH-targeted constitutive CAG-EGFP hPSCs and in dual GSH-targeted inducible TRE-EGFP hPSCs following induction with doxycycline. Wild-type hPSCs and non-induced TRE-EGFP cells were included as negative controls.

FIG. 2(a) is a schematic of this conversion, in which cells transformed according to the invention with NGN2 are induced to differentiate into neuronal cells following Dox treatment. FIG. 2(b) demonstrates the forward programming time course of i-Neuron generation from hESCs documented by quantitative RT-PCR-analysis, which demonstrates the temporal expression pattern of pan-neuronal (MAP2, SYP), forebrain (BRN2, FOXG1) and glutamatergic neuronal marker genes (VGLUT2, GRIA4). Cells were analyzed at the indicated days of doxycycline treatment. Values are shown relative to the endogenous housekeeping gene PBGD and normalized to pluripotency conditions. Results are from three biological replicates per time point and are expressed as mean±SEM. FIG. 2(c) depicts the quantification of βIII-tubulin (TUBB3) positive neuronal cells by immunostaining in i-Neurons derived from hESCs after one week of induction. Undifferentiated cells were used as negative control (Control), and numbers are reported for i-Neuron generation in newly isolated NGN2 expressing hESCs and after 25 passages (+P25). FIG. 2(d) are cell photographs depicting the forward programming time course of i-Neuron generation from hESCs via serial phase contrast images which illustrate morphological changes.

FIG. 3a shows a schematic of the rapid single step conversion of hPSCs into skeletal myocytes by inducible overexpression of MYOD1 and treatment with retinoic acid. FIG. 3b shows quantitative RT-PCR-analysis of the temporal expression pattern of myocyte marker genes during i-Myocyte generation from hESCs. All values are shown relative to the hPSCs. Results are from three biological replicates per time point and are expressed as mean±SEM. FIGS. 3 (c) and (d) show quantification of MHC positive cells by flow cytometry ten days after induction demonstrating that OPTi-MYOD1 hPSCs retain their myogenic potency even after extended culture periods and passaging (p) following the targeted integration of the MYOD1 system. Undifferentiated cells were used as negative control (Control), and figures are reported for i-Myocytes generation in newly isolated OPTi-MYOD1 hESCs, or in the same cells following 50 passages (+P50).

FIG. 4 (a) depicts the experimental workflow for the sequential targeting of the hROSA26 and AAVS1 loci in hPSCs. Key: Cas9n: D10A nickase mutant Cas9 endonuclease from *S. pyogenes*; ZFN: zinc-finger nuclease; Neo: neomycin; Puro: puromycin; rtTA: third generation reverse-tetracycline Trans-Activator. This depicts an inducible EGFP expression system (i-EGFP) FIG. 4(b) depicts a schematic of the hROSA26 targeting strategy. FIG. 4(c) depicts the AAVS1 targeting strategy. The key for FIGS. 4(b) and (c): R26-prom: ROSA26 locus promoter (THUMPD3-AS1 gene); AAV-prom: AAVS1 locus promoter (PPP1R12C gene); ZFN: zinc-finger nucleases; 5'-HAR/3'-HAR: upstream/downstream homology arm. SA: splice acceptor; T2A: T2A peptide; pA: polyadenylation signal; CAG: CMV early enhancer, chicken β-actin and rabbit β-globin hybrid promoter; TRE: Tet-responsive element; EGFP: enhanced green fluorescent protein. FIG. 4(d) depicts the schematic of the genotyping strategy used to identify correctly targeted hROSA26 and AAVS1 targeted hPSC lines; GSH-prom: GSH promoter (hROSA26 and AAVS1, respectively); WT: wild-type; Inducible cassette: entire exogenous sequence integrated following targeting. Locus PCR: PCR spanning the targeted locus with both primers binding exclusively to genomic DNA outside the genomic sequence corresponding to the homology arms. Note that due to its high GC-content the CAG promoter cannot be amplified by routine PCR. Therefore, correct insertion of the CAG-containing expression cassette results in loss of a PCR amplicon. The presence of the wild-type band indicates the presence of non-targeted alleles; loss of the wild-type band indicates homozygous targeting. 5'-INT/3'-INT: PCRs: PCRs spanning the 5'- and 3'-insertion site, respectively. Correctly sized PCR amplicons indicate correct integration. 3'BB PCR: PCR spanning the homology arm/targeting vector backbone junction. The presence of a PCR product indicates non-specific off-target integration of the donor plasmid. FIG. 4(e) is a gel photograph which shows the genotyping results for selected hROSA26-CAG-rtTA targeted heterozygous (HET) and homozygous (HOM) H9 hESCs. FIG. 4(f) is a gel photograph that shows the genotyping results for selected AAVS1-TRE-EGFP targeted heterozygous (HET) and homozygous (HOM) H9 hESCs. 1 kb+: 1 kb plus DNA ladder; WT: wild-type hESCs; PL: targeting plasmid; H$_2$O: water control.

FIG. 5(a) shows a dual GSH-targeted inducible EGFP H9 hESCs were pooled into four experimental groups depending whether one or both alleles of the hROSA26 and AAVS1 loci, respectively, were successfully targeted. FIG. 5(b) shows detection of the rtTA protein by Western blot in successfully targeted hetero- and homozygous H9 hROSA26-CAG-rtTA hESCs. Human ESCs carrying a second generation rtTA in a random genomic position were included as control sample. α-tubulin: loading control. FIG. 5(c) depicts flow cytometry analysis for the representative examples of the various dual GSH-targeted inducible EGFP hESCs described in FIG. 5(a). FIG. 5(d) shows median fluorescent intensity (MFI) of EGFP expression in the various dual GSH-targeted inducible EGFP hESCs described in FIG. 5(a). Cells were analysed by flow cytometry in control conditions (no doxycycline, CTR) or following 5 days of doxycycline treatment (DOX). Each data point represents an individual clonal line. CAG-EGFP hESCs and wild-type (WT) hESCs were included for comparison. Statistical analysis of doxycycline-treated groups (n=4-5, as indicated) demonstrated that EGFP expression levels were highest in double-homozygous clones (One-way ANOVA with post-hoc Dunnet's test; $F_{(2, 10)}=25.34$, p=0.0001; ** p<0.0001;  p=0.0026). This condition was selected for further experiments. FIG. 5(e) shows the percentage of EGFP$^+$ cells in the various dual GSH-targeted i-EGFP hESCs described in FIG. 5(a).

FIG. 6(a) depicts flow cytometry analysis of EGFP levels in successfully targeted live hPSCs and after their differentiation into the three germ layers treatment following treatment with doxycycline for five days. The acquisition settings were set to include the high levels of induced EGFP expression (DOX,). The non-induced control populations (CTR) are located directly next to the left y-axis. FIGS. 6(b) and 6(c) show a summary of the flow cytometry plots in 6(a), including the median fluorescent intensity (MFI) and the percentage of EGFP$^+$ cells. FIG. 6(d) shows a bar chart of quantitative RT-PCR results of EGFP mRNA expression levels of homozygous pluripotent stem cells and following differentiation into the three germ layers. WT: wild type;

FIG. 9(a) shows forward programming time course of OPTi-MYOD1 hPSCs into induced myocytes. Morphological changes were documented with automated phase contrast images that were acquired every 30 min with a Nikon Biostation IM time lapse system. Scale bars: 200 μm. FIG. 9(b) depicts qPCR results demonstrating rapid downregulation of the pluripotency factors NANOG and OCT4 upon treatment with doxycycline of OPTi-NGN2 hESCs (left graph). All five major human skeletal myocyte specific myocyte heavy chain isoforms (encoded by the MYH gene family) are strongly upregulated during myocyte forward programming (right graph). These include the two isoforms that are expressed during embryonic and postnatal muscle development (embryonic isoform MYH3; neonatal isoform MYH8) and three isoforms that are usually expressed in adult human skeletal muscle [MYH7 in slow-twitching (type I) fibers; MYH2 in fast-twitching fatigue-resistant (type IIa) fibers, and MYH1 in fast-fatigable (type 11x) fibers]. In contrast, MYH4 which represents the constituting MHC-isoform in fast-twitching, fast-fatigable myocyte fibres in cats is not expressed in significant amounts in humans (<1%) and is also not induced throughout the forward programming time course. FIG. 9(c) depicts induced skeletal myocytes express a broad range of typical marker proteins, including F-Actin (visualized through AlexaFluor488-conjugated Phalloidin toxin), Neural Cell Adhesion molecule (NCAM), Desmin (DES), Myosin Heavy Chain (MYH), Titin (TTN), α-Actinin (ACTN2) and Troponin T (TNNT), but not the myoblast progenitor markers PAX3 and PAX7. All samples were counterstained with myogenin (MYOG). Scale bars: 50 µm. DAPI: nuclear staining.

FIG. 12(a) depicts a schematic of the experimental approach for rapid conversion of OPTi-OLIG2-SOX10 hPSCs into oligodendrocyte lineage cells (i-OPCS and i-OLs). FIG. 12(b) shows the quantification of BrdU-positive cells following 3 serial passages every 4 days and concomitant BrdU-pulses each lasting 4 days (P=passage number). FIG. 12(c) shows quantitative RT-PCR-analysis of the temporal expression pattern of genes encoding for the myelin associated proteins (CNP, MAG, MBP, MOG, and PLP) during i-Oligodendrocyte generation from hPSCs. OPTi-OLIG2-SOX10 hPSCs were induced in oligodendrocyte media supplemented with PDGFaa and FGF2. After one week of induction mitogens were withdrawn to enable terminal differentiation. All values are shown relative to the endogenous housekeeping gene PBGD and normalized to pluripotency conditions. Results are from 2-3 biological replicates per time point and are expressed as mean±SEM. FIG. 12(d) depicts the quantification of CNP and PLP positive cells by immunostainings in i-oligodendrocytes derived from OPTi-OLIG2-SOX10 hPSCs after 20 days of induction. Undifferentiated cells were used as negative control, and figures are reported for i-Oligodendrocytes in newly isolated OPTi-NGN2 hPSCs and after 50 passages (+P50).

FIG. 14a shows the experimental approach—H1—H1 promoter, TO—tet operon, tetR—tetracycline repressor. FIG. 14b is a schematic of the transgenic alleles generated to obtain hESCs expressing an EFGP reporter transgene that could be silenced using an inducible EGFP shRNA. FIG. 14c shows EGFP expression in the absence or presence of tetracycline for 5 days in hESCs targeted with the indicated combinations of inducible EGFP shRNA and tetR (STD=wild type standard, OPT=codon optimized). Double-targeted hESCs that did not carry the EGFP shRNA were used as negative controls. n.s.=p>0.05 (non-significant), =p>0.01, *=p>0.001 VS same tetR line no tet and no shRNA. FIG. 14d is a representative western blot for tetR in ROSA26-targeted hESCs expressing STD or OPT tetR. HET=heterozygous targeting, HOM=homozygous targeting. hESCs with STD tetR random integration are shown as a positive reference, while WT h9 hESCs are negative controls. TUB4A4A is a loading control. Various protein amounts were loaded to facilitate quantitative comparison. FIG. 14 (E): EGFP knockdown and rescue kinetics in EGFP OPTiKD hESCs measured by flow cytometry (MFI) and qPCR (mRNA). Results are from 2 independent cultures per time point. FIG. 14(F): Tetracycline dose-response curve for EGFP knockdown in EGFP OPTiKD hESCs. The half-maximal inhibitory concentration (IC50) is reported. Results are from 2 independent cultures per dose, and the mean is shown.

FIG. 15a shows the experimental approach behind the generation of GSH EGFP reporter hPSCs to test GSH expression during differentiation. Neurons, oligodendrocytes, and astrocytes were obtained in bulk cultures containing a mixture of these cell lineages, while all other cell types were individually generated. FIG. 15b is a schematic of the ROSA26 and AAVS1 EGFP reporter transgenic alleles. R26-prom: ROSA26 locus promoter; AAV-prom: AAVS1 locus promoter; 5'-HAR/3'-HAR: upstream/downstream homology arm; SA: splice acceptor; T2A: self-cleaving T2A peptide; Neo: neomycin resistance; Puro: puromycin resistance; pA: polyadenylation signal; CAG: CAG promoter; EGFP: enhanced green fluorescent protein. FIG. 15 (C): EGFP expression in absence or presence of tetracycline for 5 days in hESCs targeted with the indicated combinations of inducible EGFP shRNA and tetR (wild-type standard tetR, STDtetR, or codon-optimized tetR, OPTtetR). Double-targeted hESCs that did not carry the EGFP shRNA were used as negative controls. Results are from 2-3 individual lines per condition (table 1). n.s.=p>0.05 (non-significant), =p<0.01,*=p<0.001 VS same tetR line no tet and no shRNA (ANOVA with post-hoc Holm-Sidak comparisons).

FIG. 16(A): Schematic of the ROSA26 targeting approach and of the genotyping strategies used to identify correctly targeted lines. Cas9n: D10A nickase mutant Cas9 endonuclease from S. pyogenes. R26-prom: ROSA26 locus promoter (THUMPD3-AS1 gene); 5'-HAR/3'-HAR: upstream/downstream homology arm; Transgene: region integrated following gene targeting; Locus PCR:

PCR product of wild-type ROSA26 locus (indicating a non-targeted allele); Locus PCR/Loss-of-allele: PCR product of targeted allele/PCR that fails if the transgene contains the GC-rich CAG promoter (indicative of expected transgene targeting); 5' INT/3' INT PCR: PCR product of transgene 5'-end/3'-end integration region (indicative of expected transgene targeting); 5' BB/3' BB PCR: PCR product of vector backbone 5'-end/3'-end (indicative of non-specific off-target plasmid integration). Note that similar targeting and genotyping strategies were applied for the AAVS1 locus targeting. FIG. 16(B): Schematic of the ROSA26 transgenic alleles generated to test the best strategy for constitutive EGFP (enhanced green fluorescent protein) expression. ENDO-EGFP: EGFP driven by the endogenous ROSA26 promoter (R26-prom; targeting vector pR26-Puro_ENDO-EGFP); EF1α-EGFP: EGFP driven by the elongation factor 1α promoter (targeting vector pR26-Neo_EF1α-EGFP); CAG-EGFP: EGFP driven by the CAG promoter (targeting vector pR26-Neo_CAG-EGFP); SA: splice acceptor; Puro: puromycin resistance (puromycin N-acetyltransferase); Neo: neomycin resistance (neomycin phosphotransferase II); pA: polyadenylation signal. FIG. 16(C): Flow cytometry quantification of the percentage of EGFP positive cells (EGFP+; the gate is shown), and of the EGFP median fluorescence intensity (MFI) in representative ROSA26-EGFP reporter hESC clonal lines, or wild-type H9 hESCs. FIG. 16(D): Percentage of EGFP positive cells in ROSA26-EGFP reporter hESCs. Results are for 3 clones with heterozygous ROSA26 targeting per condition.

FIG. 18a shows the experimental approach for the generation of inducible knockout (iKO) hPSCs. FIG. 18b depicts a schematic of the cloning procedure to generate AAVS1 targeting vectors with an inducible gRNA cassette (SEQ ID No 81: AAVS1 FWD; SEQ ID No 82: AAVS1 REV; SEQ ID No 83: tracer FWD; SEQ ID No 84: FIG. 18B tracer REV).

FIG. 18c shows the transgenic alleles generated to obtain hESCs expressing an EGFPd2 reporter transgene that could be knocked out by CRISPR/Cas9 using an inducible EGFP gRNA (EGFP sOPTiKO hESCs). Bsd: blasticidin resistance; EGFPd2: destabilized EGFP. FIG. 18 (d): Flow cytometry quantification of EGFPd2 inducible knockout kinetics in sOPTiKO cells from FIG. 19c (gRNA 2—TO) and b (gRNA 3-2TO). The percentage of EGFP positive cells was monitored daily following addition of tetracycline. Results are from 2 independent cultures.

FIG. 19(e): Nucleotide sequences of inducible H1 Pol III promoters for the sOPTiKO system containing one or two tet operons (SEQ ID NO: 85 corresponding to H1-TO and SEQ ID NO: 86 corresponding to H1-2TO, respectively). Key sequence features are highlighted. The restriction enzyme cut sites used for gRNA cloning are shown (FIG. 18B). DSE: distal sequence element; PSE: proximal sequence element; TETO2: tet operon; +1: start position of RNA transcription.

DETAILED DESCRIPTION

The inventors have developed a method that is useful for inducible transcription of genetic sequences comprised within inducible cassettes in eukaryotic cells, and specifically pluripotent stem cells and their progeny.

It is particularly applicable to the forward programming of pluripotent stem cells, via overexpression of inducible cassettes within said stem cell that promote development of a particular mature cell type. Further, it is also applicable to the knockdown or knockout of endogenous functions within the cell in order to study loss of function or alter cellular functions or behaviour in these cells. Knockdown or knockout may apply to protein-encoding genes or to DNA sequences encoding non-coding RNA. Either may be targeted by the methods of the present invention by knockout or knockdown.

Figure 5:
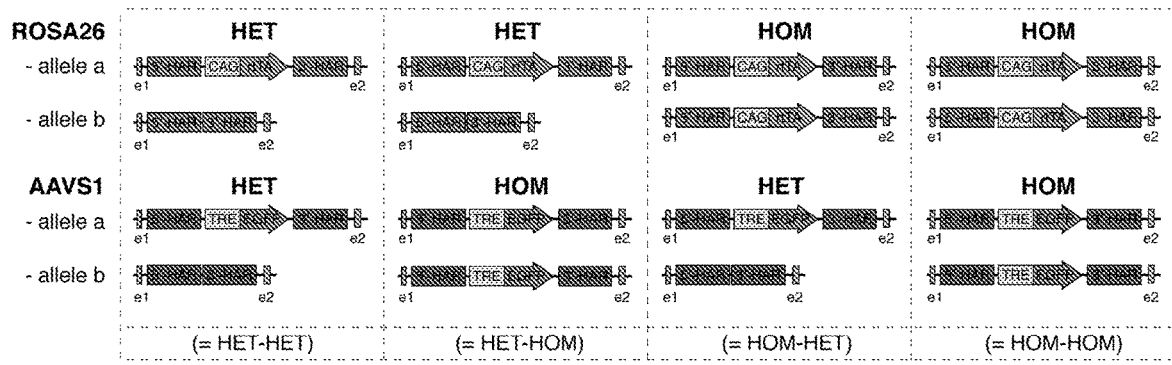
FIG. 5 (a-e): Development of an optimized inducible overexpression platform (OPTi-OX) based on hPSC dual GSH targeting.
Figure 5:
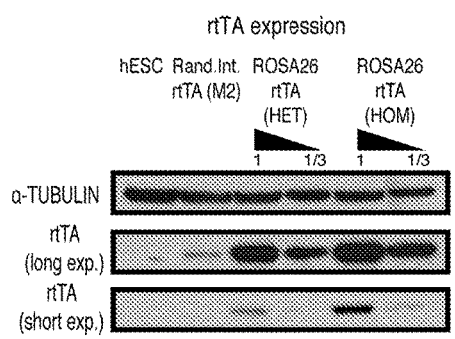
Figure 5:
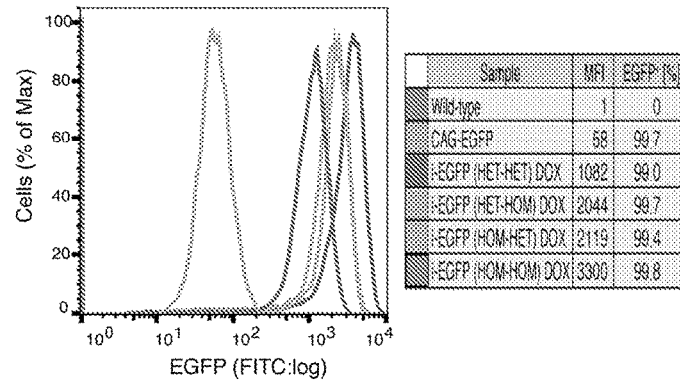
Figure 5:
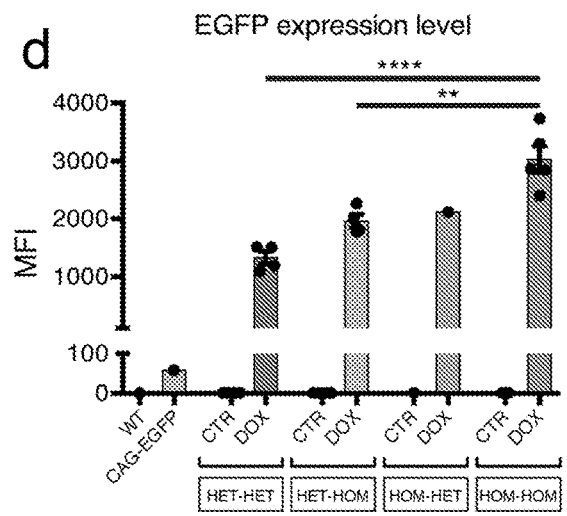
Figure 5:
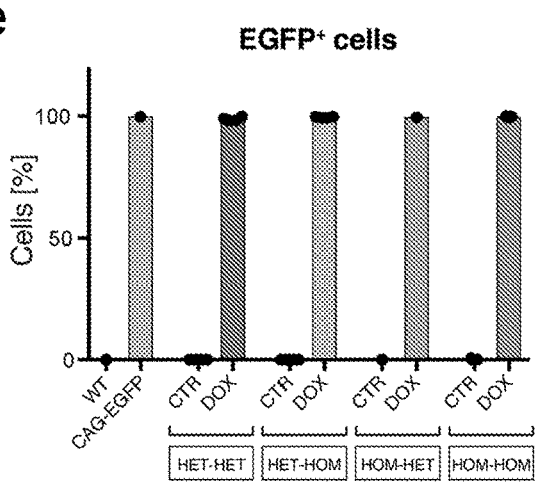

This method is based upon the at least dual targeting of safe harbour sites in the genome of the stem cell, with the system for induced transcription split over two or more GSH. However, this method is not limited to stem cells, and can be used to modify the genome of any cell type, for example in research or in gene therapy. In the methods of the invention one GSH is modified to contain a transcriptional regulator that is required to induce transcription of the genetic sequence contained within the inducible cassette inserted into a different GSH elsewhere in the genome. The transcriptional regulator is preferably constitutively expressed. It is preferred that an exogenous substance/agent has to be supplied in order to control the activity of the transcriptional regulator protein and thus control expression of the inducible cassette. Since at least two separate GSH are used in the method of the invention, there are a total of four possible insertion loci, since each GSH exists on both chromosomes of a diploid organism. This increases the amount of transcription possible from the cell if all four loci are modified using the method of the invention. An example of various outcomes of the targeted insertion is shown in FIG. 5a. Further, the method of the invention uses at least two different GSH sites. It will be understood that further GSH sites could be used to introduce further transcriptional regulators, inducible cassettes or any other genetic material including, but not limited to selectable markers, antibiotic or drug resistance genes, genes relating to the CRISPR/Cas9 system or genes of unknown function.

Thus, the present invention relates to a method for controlling the expression of an inserted genetic sequence in a cell, comprising the following steps:
a) targeted insertion of a genetic sequence encoding a transcriptional regulator protein into a first genetic safe harbour site; and
b) targeted insertion of an inducible cassette into a second genetic safe harbour site, wherein said inducible cassette comprises said genetic sequence operably linked to an inducible promoter, and said promoter is regulated by the transcriptional regulator protein;
wherein said first and second genetic safe harbour sites are different.

Further, in this aspect of the invention, a further identical or different inducible cassette may be inserted into a further GSH, which is different to the first and second GSH. Such an inducible cassette is as described herein.

Insertions specifically within genetic safe harbour sites is preferred over random genome integration, since this is expected to be a safer modification of the genome, and is less likely to lead to unwanted side effects such as silencing natural gene expression or causing mutations that lead to cancerous cell types.

A genetic safe harbour (GSH) site is a locus within the genome wherein a gene or other genetic material may be inserted without any deleterious effects on the cell or on the inserted genetic material. Most beneficial is a GSH site in which expression of the inserted gene sequence is not perturbed by any read-through expression from neighbouring genes and expression of the inducible cassette minimizes interference with the endogenous transcription programme. More formal criteria have been proposed that assist in the determination of whether a particular locus is a GSH site in future (Papapetrou et al, 2011, Nature Biotechnology, 29(1), 73-8. doi:10.1038/nbt.1717.) These criteria include a site that is (i) 50 kb or more from the 5' end of any gene, (ii) 300 kb or more from any gene related to cancer, (iii) 300 kb or more from any microRNA (miRNA), (iv) located outside a transcription unit and (v) located outside ultraconserved regions (UCR). It may not be necessary to satisfy all of these proposed criteria, since GSH already identified do not fulfil all of the criteria. It is thought that a suitable GSH will satisfy at least 2, 3, 4 or all of these criteria.

Further sites may be identified by looking for sites where viruses naturally integrate without disrupting natural gene expression.

Any suitable GSH site may be used in the method of the invention, on the basis that the site allows insertion of genetic material without deleterious effects to the cell and permits transcription of the inserted genetic material. Those skilled in the art may use this simplified criteria to identify a suitable GSH, and/or the more formal criteria set out above.

For the human genome, several GSH sites have been identified, and these include the AAVS1 locus, the hROSA26 locus and the CLYBL gene. The CCR5 gene and HPRTgene have also been mooted as possible GSHs, and further investigation may identify one or more of these as GSHs in the human genome.

The adeno-associated virus integration site 1 locus (AAVS1) is located within the protein phosphatase 1, regulatory subunit 12C (PPP1R12C) gene on human chromosome 19, which is expressed uniformly and ubiquitously in human tissues. This site serves as a specific integration locus for AAV serotype 2, and thus was identified as a possible GSH. AAVS1 has been shown to be a favourable environment for transcription, since it comprises an open chromatin structure and native chromosomal insulators that enable resistance of the inducible cassettes against silencing. There are no known adverse effects on the cell resulting from disruption of the PPP1R12C gene. Moreover, an inducible cassette inserted into this site remains transcriptionally active in many diverse cell types. AAVS1 is thus considered to be a GSH and has been widely utilized for targeted trangenesis in the human genome.

The hROSA26 site has been identified on the basis of sequence analogy with a GSH from mice (ROSA26— reverse oriented splice acceptor site #26). Although the orthologue site has been identified in humans, this site is not commonly used for inducible cassette insertion. The present inventors have developed a targeting system specifically for the hROSA26 site and thus were able to insert genetic material into this locus. The hROSA26 locus is on chromosome 3 (3p25.3), and can be found within the Ensembl database (GenBank:CR624523). The exact genomic co-ordinates of the integration site are 3:9396280-9396303: Ensembl. The integration site lies within the open reading frame (ORF) of the THUMPD3 long non-coding RNA (reverse strand). Since the hROSA26 site has an endogenous promoter, the inserted genetic material may take advantage of that endogenous promoter, or alternatively may be inserted operably linked to a promoter.

Intron 2 of the Citrate Lyase Beta-like (CLYBL) gene, on the long arm of Chromosome 13, was identified as a suitable GSH since it is one of the identified integration hot-spots of the phage derived phiC31 integrase.

Studies have demonstrated that randomly inserted inducible cassettes into this locus are stable and expressed. It has been shown that insertion of inducible cassettes at this GSH do not perturb local gene expression (Cerbibi et al, 2015, PLOS One, D01:10.1371). CLYBL thus provides a GSH which may be suitable for use in the present invention.

CCR5, which is located on chromosome 3 (position 3p21.31) is a gene which codes for HIV-1 major co-receptor. Interest in the use of this site as a GSH arises from the null mutation in this gene that appears to have no adverse effects, but predisposes to HIV-1 infection resistance. Zinc-finger nucleases that target the third exon have been developed, thus allowing for insertion of genetic material at this locus. Given that the natural function of CCR5 has yet to be elucidated, the site remains a putative GSH which may have utility for the present invention.

The hypoxanthine-guanine phosphoribosyltransferase (HPRT) gene encodes a transferase enzyme that plays a central role in the generation of purine nucleotides through the purine salvage pathway. Thus, further work is required to ensure insertions at this site do not disrupt normal cellular function. However, it has been mooted as a GSH site. Insertions at this site may be more applicable for mature cell types, such as modification for gene therapy.

GSH in other organisms have been identified and include ROSA26, HRPT and Hipp11 (H11) loci in mice. Mammalian genomes may include GSH sites based upon pseudo attP sites. For such sites, hiC31 integrase, the *Streptomyces* phage-derived recombinase, has been developed as a non-viral insertion tool, because it has the ability to integrate a inducible cassette-containing plasmid carrying an attB site into pseudo attP sites.

GSH are also present in the genomes of plants, and modification of plant cells can form part of the present invention. GSH have been identified in the genomes of rice (Cantos et al, Front. Plant Sci., 26 Jun. 2014, Volume 5, Article 302, http://dx.doi.org/10.3389/fpls.2014.00302).

In the methods of the invention, insertions occur at different GSH, thus at least two GSH are required for the method of the invention. The first GSH is modified by insertion of a transcriptional regulator protein. The second GSH is modified by the insertion of an inducible cassette which comprises a genetic sequence operably linked to an inducible promoter. Other genetic material may also be inserted with either or both of these elements. The genetic sequence operably linked to an inducible promoter within the inducible cassette is preferably a DNA sequence. The genetic sequence(s) of the inducible cassette preferably encode an RNA molecule, and are thus capable of being transcribed. The transcription is controlled using the inducible promoter. The RNA molecule may be of any sequence, but is preferably a mRNA encoding a protein, a shRNA or a gRNA.

The first GSH can be any suitable GSH site. Optionally, it is a GSH with an endogenous promoter that is constitutively expressed; which will result in the inserted transcriptional regulator protein being constitutively expressed. A suitable GSH is the hROSA26 site for human cells. Alternatively, the inserted transcriptional regulator protein is operably linked to a promoter, preferably a constitutive promoter. A constitutive promoter can be used in conjunction with an insertion in the hROSA26 site.

A transcriptional regulator protein is a protein that bind to DNA, preferably sequence-specifically to a DNA site located in or near a promoter, and either facilitating the binding of the transcription machinery to the promoter, and thus transcription of the DNA sequence (a transcriptional activator) or blocks this process (a transcriptional repressor). Such entities are also known as transcription factors.

The DNA sequence that a transcriptional regulator protein binds to is called a transcription factor-binding site or response element, and these are found in or near the promoter of the regulated DNA sequence.

Transcriptional activator proteins bind to a response element and promote gene expression. Such proteins are preferred in the methods of the present invention for controlling inducible cassette expression.

Transcriptional repressor proteins bind to a response element and prevent gene expression.

Transcriptional regulator proteins may be activated or deactivated by a number of mechanisms including binding of a substance, interaction with other transcription factors (e.g., homo- or hetero-dimerization) or coregulatory proteins, phosphorylation, and/or methylation. The transcriptional regulator may be controlled by activation or deactivation.

If the transcriptional regulator protein is a transcriptional activator protein, it is preferred that the transcriptional activator protein requires activation. This activation may be through any suitable means, but it is preferred that the transcriptional regulator protein is activated through the addition to the cell of an exogenous substance. The supply of an exogenous substance to the cell can be controlled, and thus the activation of the transcriptional regulator protein can be controlled. Alternatively, an exogenous substance can be supplied in order to deactivate a transcriptional regulator protein, and then supply withdrawn in order to activate the transcriptional regulator protein.

If the transcriptional regulator protein is a transcriptional repressor protein, it is preferred that the transcriptional repressor protein requires deactivation. Thus, a substance is supplied to prevent the transcriptional repressor protein repressing transcription, and thus transcription is permitted.

Any suitable transcriptional regulator protein may be used, preferably one that is activatable or deactivatable. It is preferred that an exogenous substance may be supplied to control the transcriptional regulator protein. Such transcriptional regulator proteins are also called inducible transcriptional regulator proteins.

Tetracycline-Controlled Transcriptional Activation is a method of inducible gene expression where transcription is reversibly turned on or off in the presence of the antibiotic tetracycline or one of its derivatives (e.g. doxycycline which is more stable). In this system, the transcriptional activator protein is tetracycline-responsive transcriptional activator protein (rtTa) or a derivative thereof. The rtTA protein is able to bind to DNA at specific TetO operator sequences. Several repeats of such TetO sequences are placed upstream of a minimal promoter (such as the CMV promoter), which together form a tetracycline response element (TRE). There are two forms of this system, depending on whether the addition of tetracycline or a derivative activates (Tet-On) or deactivates (Tet-Off) the rtTA protein.

In a Tet-Off system, tetracycline or a derivative thereof binds rtTA and deactivates the rtTA, rendering it incapable of binding to TRE sequences, thereby preventing transcription of TRE-controlled genes. This system was first described in Bujard, et al (1992). Proc. Natl. Acad. Sci. U.S.A. 89 (12): 5547-51.

Figure 11:
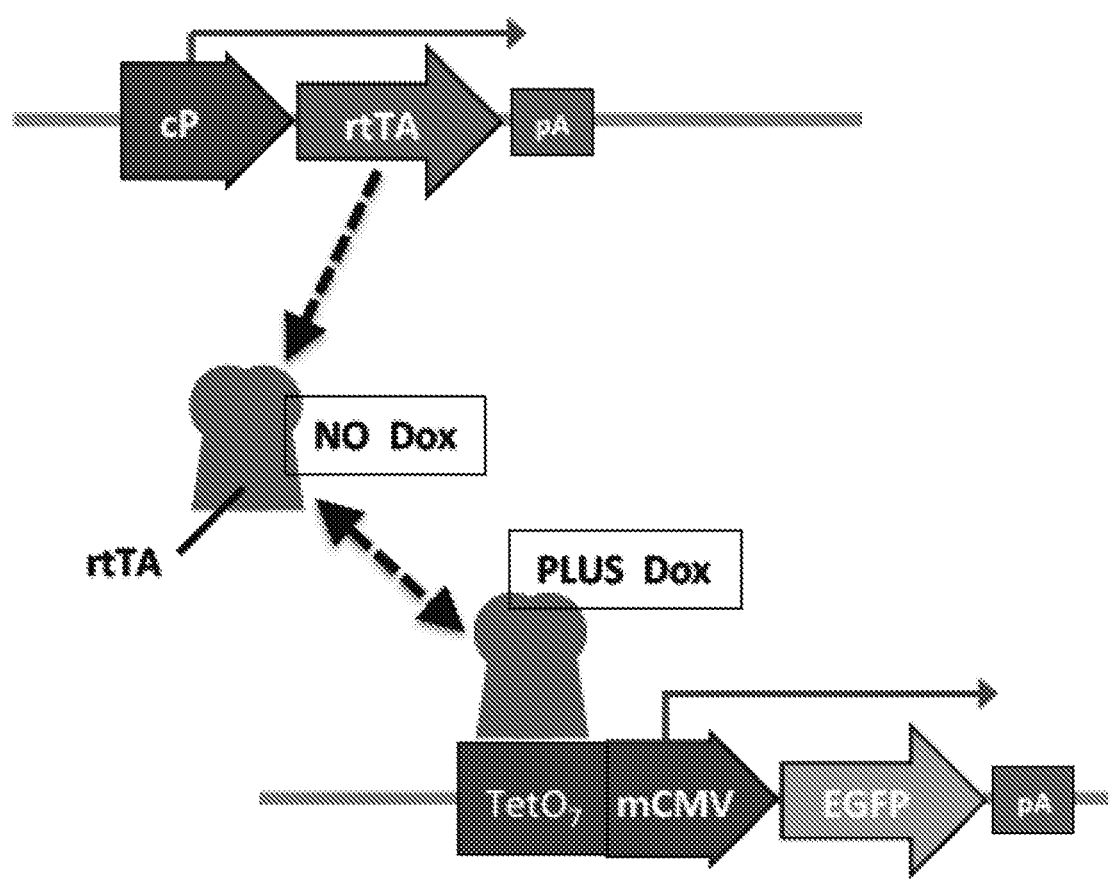
FIG. 11: A depiction of the Tet-ON system. The Tet-ON consists of two components: At the top the activator cassette is depicted, in which a constitutive promoter (cP) drives expression of rtTA (reverse-tetracycline Trans-Activator). RtTA is a fusion protein that consists of a mutant form of the prokaryotic Tet Repressor (TetR) and the transcriptional trans-activator domain VP16 (derived from herpes simplex virus). At the bottom the responder domain is depicted. It consists of an inducible promoter (TRE, Tet Responsive Element) and the gene of interest. The TRE is an artificial promoter responsive to rtTA. It consists of 7 serial tet operons (tet07) and a strong minimal CMV promoter (mCMV), which itself is not active and only recruits the transcriptional machinery upon binding of rtTA to the seven tet operons. Doxycycline, a tetracycline derivative, is required for binding of the mutant TetR to the TRE, leading to expression of the inducible cassette, in this case EGFP. (pA: polyadenylation signal).

The Tet-On system is composed of two components; (1) the constitutively expressed tetracycline-responsive transcriptional activator protein (rtTa) and the rtTa sensitive inducible promoter (Tet Responsive Element, TRE). This may be bound by tetracycline or its more stable derivatives, including doxycycline (dox), resulting in activation of rtTa, allowing it to bind to TRE sequences and inducing expression of TRE-controlled genes. The use of this may be preferred in the method of the invention. This system is depicted in FIG. 11.

Thus, the transcriptional regulator protein may thus be tetracycline-responsive transcriptional activator protein (rtTa) protein, which can be activated or deactivated by the antibiotic tetracycline or one of its derivatives, which are supplied exogenously. If the transcriptional regulator protein is rtTA, then the inducible promoter inserted into the second GSH site includes the tetracycline response element (TRE). The exogenously supplied substance is the antibiotic tetracycline or one of its derivatives.

Variants and modified rtTa proteins may be used in the methods of the invention, these include Tet-On Advanced transactivator (also known as rtTA2S-M2) and Tet-On 3G (also known as rtTA-V16, derived from rtTA2S-52.

The tetracycline response element (TRE) generally consists of 7 repeats of the 19 bp bacterial TetO sequence separated by spacer sequences, together with a minimal promoter. Variants and modifications of the TRE sequence are possible, since the minimal promoter can be any suitable promoter. Preferably the minimal promoter shows no or minimal expression levels in the absence of rtTa binding. The inducible promoter inserted into the second GSH may thus comprise a TRE.

A modified system based upon tetracycline control is the T-REx™ System (Thermofisher Scientific), in which the transcriptional regulator protein is a transcriptional repressor protein, TetR. The components of this system include (i) an inducible promoter comprising a strong human cytomegalovirus immediate-early (CMV) promoter and two tetracycline operator 2 (TetO2) sites, and a Tet repressor (TetR). The TetO2 sequences consist of 2 copies of the 19 nucleotide sequence, 5"-TCCCTATCAGTGATAGAGA-3" (SEQ ID NO: 1) separated by a 2 base pair spacer. In the absence of tetracycline, the Tet repressor forms a homodimer that binds with extremely high affinity to each TetO2 sequence in the inducible promoter, and prevent transcription from the promoter. Once added, tetracycline binds with high affinity to each Tet repressor homodimer rendering it unable to bind to the Tet operator. The Tet repressor: tetracycline complex then dissociates from the Tet operator and allows induction of expression. In this instance, the transcriptional regulator protein is TetR and the inducible promoter comprises two TetO2 sites. The exogenously supplied substance is tetracycline or a derivative thereof.

The invention further relates to a codon-optimised tetR (OPTtetR). This may be used in any method described herein, or for any additional use where inducible promotion is desirable. This entity was generated using multiparameter-optimisation of the bacterial tetR cDNA sequence. OPTtetR allows a ten-fold increase in the tetR expression when compared to the standard sequence (STDtetR). Homozygous OPTtetR expression of tetR was sufficient to prevent shRNA leakiness whilst preserving knockdown induction in the Examples. The sequence for OPTtetR is included here, with the standard sequence shown as a comparison. Sequences with at least 75%, 80%, 85% or 90% homology for this sequence are hereby claimed, more particularly 91, 92, 93, 94, 95, 96, 97 or 99% homology. Residues shown to be changed between STDtetR and OPTtetR have been indicated in the sequences, and it is preferred that these residues are not changed in any derivative of OPTtetR since these are thought to be important for the improved properties. Any derivative would optionally retain these modifications at the indicated positions.

Other inducible expression systems are known and can be used in the method of the invention. These include the Complete Control Inducible system from Agilent Technologies. This is based upon the insect hormone ecdysone or its analogue ponasterone A (ponA) which can activate transcription in mammalian cells which are transfected with both the gene for the *Drosophila melongaster* ecdysone receptor (EcR) and an inducible promoter comprising a binding site for the ecdysone receptor. The EcR is a member of the retinoid-X-receptor (RXR) family of nuclear receptors. In humans, EcR forms a heterodimer with RXR that binds to the ecdysone-responsive element (EcRE). In the absence of PonA, transcription is repressed by the heterodimer.

Thus, the transcriptional regulator protein can be a repressor protein, such as an ecdysone receptor or a derivative thereof. Examples of the latter include the VgEcR synthetic receptor from Agilent technologies which is a fusion of EcR, the DNA binding domain of the glutocorticoid receptor and the transcriptional activation domain of Herpes Simplex Virus VP16. The inducible promoter comprises the EcRE sequence or modified versions thereof together with a minimal promoter. Modified versions include the E/GRE recognition sequence of Agilent Technologies, in which mutations to the sequence have been made. The E/GRE recognition sequence comprises inverted half-site recognition elements for the retinoid-X-receptor (RXR) and GR binding domains. In all permutations, the exogenously supplied substance is ponasterone A, which removes the repressive effect of EcR or derivatives thereof on the inducible promoter, and allows transcription to take place.

Alternatively, inducible systems may be based on the synthetic steroid mifepristone as the exogenously supplied substance. In this scenario, a hybrid transcriptional regulator protein is inserted, which is based upon a DNA binding domain from the yeast GAL4 protein, a truncated ligand binding domain (LBD) from the human progesterone receptor and an activation domain (AD) from the human NF-κB. This hybrid transcriptional regulator protein is available from Thermofisher Scientific (Gene Switch™). Mifepristone activates the hybrid protein, and permits transcription from the inducible promoter which comprises GAL4 upstream activating sequences (UAS) and the adenovirus E1b TATA box. This system is described in Wang, Y. et al (1994) Proc. Natl. Acad. Sci. USA 91, 8180-8184.

The transcriptional regulator protein can thus be any suitable regulator protein, either an activator or repressor protein. Suitable transcriptional activator proteins are tetracycline-responsive transcriptional activator protein (rtTa) or the Gene Switch hybrid transcriptional regulator protein. Suitable repressor proteins include the Tet-Off version of rtTA, TetR or EcR. The transcriptional regulator proteins may be modified or derivatised as required.

The inducible promoter can comprise elements which are suitable for binding or interacting with the transcriptional regulator protein. The interaction of the transcriptional regulator protein with the inducible promoter is preferably controlled by the exogenously supplied substance.

The exogenously supplied substance can be any suitable substance that binds to or interacts with the transcriptional regulator protein. Suitable substances include tetracycline, ponasterone A and mifepristone.

Thus, the insertion of the gene encoding a transcriptional regulator protein into the first GSH provides the control mechanism for the expression of the inducible cassette which is operably linked to the inducible promoter and inserted into a second, different, GSH site.

The transcriptional regulator protein gene may be provided for insertion with other genetic material. Such material includes genes for markers or reporter molecules, such as genes that induce visually identifiable characteristics including fluorescent and luminescent proteins. Examples include the gene that encodes jellyfish green fluorescent protein (GFP), which causes cells that express it to glow green under blue/UV light, luciferase, which catalyses a reaction with luciferin to produce light, and the red fluorescent protein from the gene dsRed. Such markers or reporter genes are useful, since the presence of the reporter protein confirms protein expression from the first GSH, indicating successful insertion. Selectable markers may further include resistance genes to antibiotics or other drugs. Markers or reporter gene sequences can also be introduced that enable studying the expression of endogenous (or exogenous genes). This includes Cas proteins, including CasL, Cas9 proteins that enable excision of genes of interest, as well as Cas-Fusion proteins that mediate changes in the expression of other genes, e.g. by acting as transcriptional enhancers or repressors. Moreover, non-inducible expression of molecular tools may be desirable, including optogenetic tools, nuclear receptor fusion proteins, such as tamoxifen-inducible systems ERT, and designer receptors exclusively activated by designer drugs. Furthermore, sequences that code signalling factors that alter the function of the same cell or of neighbouring or even distant cells in an organism, including hormones autocrine or paracrine factors may be co-expressed from the same GSH as the transcriptional regulator protein.

Additionally, the further genetic material may include sequences coding for non-coding RNA, as discussed herein. Examples of such genetic material includes genes for miRNA, which may function as a genetic switch.

It is preferred that the gene encoding the transcriptional regulator protein is operably linked to a constitutive promoter. Alternatively, the first GSH can be selected such that it already has a constitutive promoter than can also drive expression of the transcriptional regulator protein gene and any associated genetic material. Constitutive promoters ensure sustained and high level gene expression. Commonly used constitutive promoters, including the human β-actin promoter (ACTB), cytomegalovirus (CMV), elongation factor-1α, (EF1α), phosphoglycerate kinase (PGK) and ubiquitinC (UbC). The CAG promoter is a strong synthetic promoter frequently used to drive high levels of gene expression and was constructed from the following sequences: (C) the cytomegalovirus (CMV) early enhancer element, (A) the promoter, the first exon and the first intron of chicken beta-actin gene, and (G) the splice acceptor of the rabbit beta-globin gene.

Further, the transcriptional regulator, plus any further genetic material may be provided together with cleavable sequences. Such sequences are sequences that are recognised by an entity capable of specifically cutting DNA, and include restriction sites, which are the target sequences for restriction enzymes or sequences for recognition by other DNA cleaving entities, such as nucleases, recombinases, ribozymes or artificial constructs. At least one cleavable sequence may be included, but preferably two or more are present. These cleavable sequences may be at any suitable point in the insertion, such that a selected portion of the insertion, or all of the insertion, can be selectively removed from the GSH. The method can thus extend to removal and/or replacement of the insertion or a portion thereof from the GSH. The cleavable sites may thus flank the part/all of the insertion that it may be desired to remove. The transcriptional regulator and/or the further genetic material may be removed using this method.

A portion of the insertion may be any part up to 99% of the insertion—i.e. 1-99%, 90%, 80%, 70%, 60%, 50%, 40%, 30%, 20%, 10% or less than 10%.

It may be preferred that the portion of the insertion flanked by the cleavable sites includes the constitutive promoter. Alternatively, the constitutive promoter is not included in the portion flanked by the cleavable sequences.

A preferred cleavable sequence is the loxP site for Cre recombinase as it allows direct replacement of the removed insertion. Alternatively or additionally, the cleavable sequence is the rox site for Dre recombinase.

It is preferred that the insertion at the first GSH occurs at both loci in the genome, thus each allele is modified by insertion. This permits greater expression from the gene encoding the transcriptional regulator and any associated genetic material.

The second GSH can be any suitable GSH site. It may be preferred that the second GSH site is not associated with an endogenous promoter, such that the expression of the inserted inducible cassette is solely under control of the transcriptional regulator protein.

An inducible cassette includes a desired genetic sequence, preferably a DNA sequence, that is to be transferred into a cell. The introduction of an inducible cassette into the genome has the potential to change the phenotype of that cell, either by addition of a genetic sequence that permits gene expression or knockdown/knockout of endogenous expression. The methods of the invention provide for controllable transcription of the genetic sequence(s) within the inducible cassette in the cell.

The desired genetic sequence for insertion is preferably a DNA sequence that encodes an RNA molecule. The RNA molecule may be of any sequence, but is preferably coding or non-coding RNA. Coding or messenger RNA codes for polypeptide sequences, and transcription of such RNA leads to expression of a protein within the cell. Non-coding RNA may be functional and may include without limitation: MicroRNA, Small interfering RNA, Piwi-interacting RNA, Antisense RNA, Small nuclear RNA, Small nucleolar RNA, Small Cajal Body RNA, Y RNA, Enhancer RNAs, Guide RNA, Ribozymes, Small hairpin RNA, Small temporal RNA, Trans-acting RNA, small interfering RNA and Subgenomic messenger RNA. Non-coding RNA may also be known as functional RNA.

Several types of RNA are regulatory in nature, and, for example, can downregulate gene expression by being complementary to a part of an mRNA or a gene's DNA. MicroRNAs (miRNA; 21-22 nucleotides) are found in eukaryotes and act through RNA interference (RNAi), where an effector complex of miRNA and enzymes can cleave complementary mRNA, block the mRNA from being translated, or accelerate its degradation. Another type of RNA, small interfering RNAs (siRNA; 20-25 nucleotides) act through RNA interference in a fashion similar to miRNAs. Some miRNAs and siRNAs can cause genes they target to be methylated, thereby decreasing or increasing transcription of those genes. Animals have Piwi-interacting RNAs (piRNA; 29-30 nucleotides) that are active in germline cells and are thought to be a defence against transposons. Many prokaryotes have CRISPR RNAs, a regulatory system similar to RNA interference, and such a system include guide RNA (gRNA). Antisense RNAs are widespread; most downregulate a gene, but a few are activators of transcription. Antisense RNA can act by binding to an mRNA, forming double-stranded RNA that is enzymatically degraded. There are many long noncoding RNAs that regulate genes in eukaryotes, one such RNA is Xist, which coats one X chromosome in female mammals and inactivates it. Thus, there are a multitude of functional RNAs that can be employed in the methods of the present invention.

Thus, the inducible cassette may include a genetic sequence that is a protein-coding gene. This gene may be not naturally present in the cell, or may naturally occur in the cell, but controllable expression of that gene is required. Alternatively, the inducible cassette may be a mutated, modified or correct version of a gene present in the cell, particularly for gene therapy purposes or the derivation of disease models. The inducible cassette may thus include a transgene from a different organism of the same species (i.e. a diseased/mutated version of a gene from a human, or a wild-type gene from a human) or be from a different species.

In any aspect or embodiment, the genetic sequence comprised within the inducible cassette may be a synthetic sequence.

The inducible cassette may include any suitable genetic sequence that it is desired to insert into the genome of the cell. Therefore, the genetic sequence may be a gene that codes for a protein product or a sequence that is transcribed into ribonucleic acid (RNA) which has a function (such as small nuclear RNA (snRNA), antisense RNA, micro RNA (miRNA), small interfering RNA (siRNA), transfer RNA (tRNA) and other non-coding RNAs (ncRNA), including CRISPR-RNA (crRNA) and guide RNA (gRNA).

The inducible cassette may thus include be any genetic sequence, the transcription of which it is desired to control within the cell. The genetic sequence chosen will be dependent upon the cell type and the use to which the cell will be put after modification, as discussed further below.

For example, for gene therapy methods, it may be desirable to provide the wild-type gene sequence as a component of the inducible cassette. In this scenario, the genetic sequence may be any human or animal protein-coding gene. Examples of protein-encoding genes include the human β-globin gene, human lipoprotein lipase (LPL) gene, Rab escort protein 1 in humans encoded by the CHM gene and many more. Alternatively, the inducible cassette may express Growth factors, including BDNF, GDF, NGF, IGF, FGF and/or enzymes that can cleave pro-peptides to form active forms. Gene therapy may also be achieved by expression of an inducible cassette including a genetic sequence encoding an antisense RNA, a miRNA, a siRNA or any type of RNA that interferes with the expression of another gene within the cell.

Alternatively, should the cell be a stem cell, the inducible cassette may include a genetic sequence encoding a key lineage specific master regulator, abbreviated here are master regulator. Master regulators may be one or more of: transcription factors, transcriptional regulators, cytokine receptors or signalling molecules and the like. A master regulator is an expressed gene that influences the lineage of the cell expressing it. It may be that a network of master regulators is required for the lineage of a cell to be determined. As used herein, a master regulator gene that is expressed at the inception of a developmental lineage or cell type, participates in the specification of that lineage by regulating multiple downstream genes either directly or through a cascade of gene expression changes. If the master regulator is expressed it has the ability to re-specify the fate of cells destined to form other lineages. Examples of master regulators include the myogenic transcription factor MyoD and the hematopoietic transcription factor SCL. Particularly, master regulators include, but are not limited to:

Neural lineages: Oligodendrocytes: SOX10, OLIG2, NKX2.2, NKX6.2; Astrocytes: NFIA, NFIB, and SOX9; Neurons: Ascl1, neurogenin, and NeuroD, Pax6, Neurog2, Ascl1, Dlx2, and NeuroD1; Haematopoetic Cells, including Erythrocytes and Megakaryocytes: GATA1, FLI1 and TAL1

Mesenchymal lineages: Skeletal muscle: MYOD; Cardiomyocytes: Gata4, Mef2c, Baf60c and Tbx5; Bone: L-Myc (RXOL) Runx2, Osterix, Oct4; Cartilage: c-Myc Klf4, SOX9; and Brown adipocytes: C/EBP-β and c-Myc Endoderm Pancreatic cell types: PDX1 and GATA6.

Stem Cells: Epiblast SC: Oct4, Sox2, Klf4 and c-Myc

Alternatively, or additionally, the genetic sequence or further genetic material may be genes whose function requires investigation, such that controllable expression can look at the effect of expression on the cell; the gene may include growth factors and/or cytokines in order for the cells to be used in cell transplantation; and/or the gene may be components of a reporter assay.

Further, the genetic sequence may encode non-coding RNA whose function is to knockdown the expression of an endogenous gene or DNA sequence encoding non-coding RNA in the cell. Alternatively, the genetic sequence may encode guide RNA for the CRISPR-Cas9 system to effect endogenous gene knockout.

The methods of the invention thus extend to methods of knocking down endogenous gene expression within a cell. The methods are as described previously, and the inducible cassette comprises a genetic sequence encoding a non-coding RNA operably linked to an inducible promoter, wherein the non-coding RNA suppresses the expression of said endogenous gene. The non-coding RNA may suppress gene expression by any suitable means including RNA interference and antisense RNA. Thus, the genetic sequence may encode a shRNA which can interfere with the messenger RNA for the endogenous gene.

The reduction in endogenous gene expression may be partial or full—i.e. expression may be 50, 55, 65, 70, 75, 80, 85, 90, 91, 92, 93, 94, 95, 96, 97, 98, 99 or 100% reduced compared to the cell prior to induction of the transcription of the non-coding RNA.

The methods of the invention also extend to methods of knocking out endogenous genes within a cell, by virtue of the CRISPR-Cas9 system, although any other suitable systems for gene knockout may be used. In this scenario, it is preferred that the Cas9 genes are constitutively expressed, and thus are included in the first GSH with the gene for the transcriptional regulator. Genetic sequences encoding the gRNAs may be included in the inducible cassette, which is inserted into the second GSH. gRNA is a short synthetic RNA composed of a scaffold sequence necessary for Cas9-binding and an approximately 20 nucleotide targeting sequence which defines the genomic target to be modified. Thus, the genomic target of Cas9 can be changed by simply changing the targeting sequence present in the gRNA. Although the primary use of such a system is to design a gRNA to target an endogenous gene in order to knockout the gene, it can also be modified to electively activate or repress target genes, purify specific regions of DNA, and even image DNA. All possible uses are envisaged.

The inducible cassette includes a genetic sequence operably linked to an inducible promoter. A "promoter" is a nucleotide sequence which initiates and regulates transcription of a polynucleotide. An "inducible promoter" is a nucleotide sequence where expression of a genetic sequence operably linked to the promoter is controlled by an analyte, co-factor, regulatory protein, etc. In the case of the present invention, the control is effected by the transcriptional regulator protein. It is intended that the term "promoter" or "control element" includes full-length promoter regions and functional (e.g., controls transcription or translation) segments of these regions. "Operably linked" refers to an arrangement of elements wherein the components so described are configured so as to perform their usual function. Thus, a given promoter operably linked to a genetic sequence is capable of effecting the expression of that sequence when the proper enzymes are present. The promoter need not be contiguous with the sequence, so long as it functions to direct the expression thereof. Thus, for example, intervening untranslated yet transcribed sequences can be present between the promoter sequence and the genetic sequence and the promoter sequence can still be considered "operably linked" to the genetic sequence. Thus, the term "operably linked" is intended to encompass any spacing or orientation of the promoter element and the genetic sequence in the inducible cassette which allows for initiation of transcription of the inducible cassette upon recognition of the promoter element by a transcription complex.

Further, other genetic material may also be operably linked to the inducible promoter. Further genetic material may include genes, coding sequences for RNA, genetic material, such as markers or reporter genes. Such additional genetic material has been discussed previously. In some circumstances, it may be desirable to include a suicide gene in the inducible cassette, should the genetic sequence itself not be a suicide gene for cancer gene therapy. The suicide gene may use the same inducible promoter within the inducible cassette, or it may be a separate inducible promoter to allow for separate control. Such a gene may be useful in gene therapy scenarios where it is desirable to be able to destroy donor/transfected cells if certain conditions are met. Suicide genes are genes that express a protein that causes the cell to undergo apoptosis, or alternatively may require an externally supplied co-factor or co-drug in order to work. The co-factor or co-drug may be converted by the product of the suicide gene into a highly cytotoxic entity.

Further, the inducible cassette may include cleavable sequences. Such sequences are sequences that are recognised by an entity capable of specifically cutting DNA, and include restriction sites, which are the target sequences for restriction enzymes or sequences for recognition by other DNA cleaving entities, such as nucleases, recombinases, ribozymes or artificial constructs. At least one cleavable sequence may be included, but preferably two or more are present. These cleavable sequences may be at any suitable point in the cassette, such that a selected portion of the cassette, or the entire cassette, can be selectively removed from the GSH. The method can thus extend to removal and/or replacement of the cassette or a portion thereof from the GSH. The cleavable sites may thus flank the part/all of the genetic sequence that it may be desired to remove. The method may result in removal of the inducible cassette and/or the further genetic material.

A portion of the cassette may be any part up to 99% of the cassette—i.e. 1-99%, 90%, 80%, 70%, 60%, 50%, 40%, 30%, 20%, 10% or less than 10%.

It may be preferred that the portion of the insertion flanked by the cleavable sites includes the promoter operably linked to the genetic sequence. Alternatively, the promoter operably linked to the genetic sequence is not included in the portion flanked by the cleavable sequences.

A preferred cleavable sequence is the loxP site for Cre recombinase as it allows direct replacement of the removed insertion. Alternatively or additionally the cleavable site may be the rox site for Dre recombinase.

The transcriptional regulator protein and the inducible cassette, together with any associated genetic material, are inserted into different GSH within the genome of the cell.

The insertions into the GSH are preferably specifically within the sequence of the GSH as described previously. Any suitable technique for insertion of a polynucleotide into a specific sequence may be used, and several are described in the art. Suitable techniques include any method which introduces a break at the desired location and permits recombination of the vector into the gap. Thus, a crucial first step for targeted site-specific genomic modification is the creation of a double-strand DNA break (DSB) at the genomic locus to be modified. Distinct cellular repair mechanisms can be exploited to repair the DSB and to introduce the desired sequence, and these are non-homologous end joining repair (NHEJ), which is more prone to error; and homologous recombination repair (HR) mediated by a donor DNA template, that can be used to insert inducible cassettes.

Several techniques exist to allow customized site-specific generation of DSB in the genome. Many of these involve the use of customized endonucleases, such as zinc finger nucleases (ZFNs), transcription activator-like effector nucleases (TALENs) or the clustered regularly interspaced short palindromic repeats/CRISPR associated protein (CRISPR/Cas9) system (Gaj, T, et al "ZFN, TALEN, and CRISPR/Cas-based methods for genome engineering," Trends Biotechnol, 31:397-405, July 2013).

Zinc finger nucleases are artificial enzymes which are generated by fusion of a zinc-finger DNA-binding domain to the nuclease domain of the restriction enzyme FokI. The latter has a non-specific cleavage domain which must dimerise in order to cleave DNA. This means that two ZFN monomers are required to allow dimerisation of the FokI domains and to cleave the DNA. The DNA binding domain may be designed to target any genomic sequence of interest, is a tandem array of Cys2His2 zinc fingers, each of which recognises three contiguous nucleotides in the target sequence. The two binding sites are separated by 5-7 bp to allow optimal dimerisation of the FokI domains. The enzyme thus is able to cleave DNA at a specific site, and target specificity is increased by ensuring that two proximal DNA-binding events must occur to achieve a double-strand break.

Transcription activator-like effector nucleases, or TALENs, are dimeric transcription factor/nucleases. They are made by fusing a TAL effector DNA-binding domain to a DNA cleavage domain (a nuclease). Transcription activator-like effectors (TALEs) can be engineered to bind practically any desired DNA sequence, so when combined with a nuclease, DNA can be cut at specific locations. TAL effectors are proteins that are secreted by *Xanthomonas* bacteria, the DNA binding domain of which contains a repeated highly conserved 33-34 amino acid sequence with divergent 12th and 13th amino acids. These two positions are highly variable and show a strong correlation with specific nucleotide recognition. This straightforward relationship between amino acid sequence and DNA recognition has allowed for the engineering of specific DNA-binding domains by selecting a combination of repeat segments containing appropriate residues at the two variable positions. TALENs are thus built from arrays of 33 to 35 amino acid modules, each of which targets a single nucleotide. By selecting the array of the modules, almost any sequence may be targeted. Again, the nuclease used may be FokI or a derivative thereof.

Three types of CRISPR mechanisms have been identified, of which type II is the most studied. The CRISPR/Cas9 system (type II) utilises the Cas9 nuclease to make a double-stranded break in DNA at a site determined by a short guide RNA. The CRISPR/Cas system is a prokaryotic immune system that confers resistance to foreign genetic elements. CRISPR are segments of prokaryotic DNA containing short repetitions of base sequences. Each repetition is followed by short segments of "protospacer DNA" from previous exposures to foreign genetic elements. CRISPR spacers recognize and cut the exogenous genetic elements using RNA interference. The CRISPR immune response occurs through two steps: CRISPR-RNA (crRNA) biogenesis and crRNA-guided interference. CrRNA molecules are composed of a variable sequence transcribed from the protospacer DNA and a CRISP repeat. Each crRNA molecule then hybridizes with a second RNA, known as the trans-activating CRISPR RNA (tracrRNA) and together these two eventually form a complex with the nuclease Cas9. The protospacer DNA encoded section of the crRNA directs Cas9 to cleave complementary target DNA sequences, if they are adjacent to short sequences known as protospacer adjacent motifs (PAMs). This natural system has been engineered and exploited to introduce DSB breaks in specific sites in genomic DNA, amongst many other applications. In particular, the CRISPR type II system from *Streptococcus pyogenes* may be used. At its simplest, the CRISPR/Cas9 system comprises two components that are delivered to the cell to provide genome editing: the Cas9 nuclease itself and a small guide RNA (gRNA). The gRNA is a fusion of a customised, site-specific crRNA (directed to the target sequence) and a standardised tracrRNA.

Once a DSB has been made, a donor template with homology to the targeted locus is supplied; the DSB may be repaired by the homology-directed repair (HDR) pathway allowing for precise insertions to be made.

Derivatives of this system are also possible. Mutant forms of Cas9 are available, such as Cas9D10A, with only nickase activity. This means it cleaves only one DNA strand, and does not activate NHEJ. Instead, when provided with a homologous repair template, DNA repairs are conducted via the high-fidelity HDR pathway only. Cas9D10A (Cong L., et al. (2013) Science, 339, 819-823) may be used in paired Cas9 complexes designed to generate adjacent DNA nicks in conjunction with two sgRNAs complementary to the adjacent area on opposite strands of the target site, which may be particularly advantageous.

The elements for making the double-strand DNA break may be introduced in one or more vectors such as plasmids for expression in the cell.

Thus, any method of making specific, targeted double strand breaks in the genome in order to effect the insertion of a gene/inducible cassette may be used in the method of the invention. It may be preferred that the method for inserting the gene/inducible cassette utilises any one or more of ZFNs, TALENs and/or CRISPR/Cas9 systems or any derivative thereof.

Once the DSB has been made by any appropriate means, the gene/inducible cassette for insertion may be supplied in any suitable fashion as described below. The gene/inducible cassette and associated genetic material form the donor DNA for repair of the DNA at the DSB and are inserted using standard cellular repair machinery/pathways. How the break is initiated will alter which pathway is used to repair the damage, as noted above.

The transcriptional regulator protein and the inducible cassette may be supplied for the method of the invention on separate vectors. A "vector" is a nucleic acid molecule, such as a DNA molecule, which is used as a vehicle to artificially carry genetic material into a cell. The vector is generally a nucleic acid sequence that consists of an insert (such as an inducible cassette or gene for a transcriptional regulator protein) and a larger sequence that serves as the "backbone" of the vector. The vector may be in any suitable format, including plasmids, minicircle, or linear DNA. The vector comprises at least the gene for the transcriptional regulator or inducible cassette operably linked to an inducible promoter, together with the minimum sequences to enable insertion of the genes into the relevant GSH. Optionally, the vectors also possess an origin of replication (ori) which permits amplification of the vector, for example in bacteria. Additionally, or alternatively, the vector includes selectable markers such as antibiotic resistance genes, genes for coloured markers and suicide genes.

Examples of the vectors used in the Examples are depicted in FIGS. 20 to 33.

The cell used in the method of the invention may be any human or animal cell. It is preferably a mammalian cell, such as a cell from a rodent, such as mice and rats; marsupial such as kangaroos and koalas; non-human primate such as a bonobo, chimpanzee, lemurs, gibbons and apes; camelids such as camels and llamas; livestock animals such as horses, pigs, cattle, buffalo, bison, goats, sheep, deer, reindeer, donkeys, bantengs, yaks, chickens, ducks and turkeys; domestic animals such as cats, dogs, rabbits and guinea pigs. The cell is preferably a human cell. In certain aspects, the cell is preferably one from a livestock animal.

The type of cell used in the method of the invention will depend upon the application of the cell once insertion of the genetic material into the GSH sites is complete.

Where the aim is to produce mature cell types from progenitor cells, the cell which is modified is a stem cell, preferably a pluripotent stem cell. Pluripotent stem cells have the potential to differentiate into almost any cell in the body. There are several sources of pluripotent stem cells. Embryonic stem cells (ES cells) are pluripotent stem cells derived from the inner cell mass of a blastocyst, an early-stage preimplantation embryo.

Induced pluripotent stem cells (iPSCs) are adult cells that have been genetically reprogrammed to an embryonic stem cell-like state by being forced to express genes and factors important for maintaining the defining properties of embryonic stem cells. In 2006 it was shown that the introduction of four specific genes encoding transcription factors could convert adult cells into pluripotent stem cells (Takahashi, K; Yamanaka, S (2006), Cell 126 (4): 663-76), but subsequent work has reduced/altered the number of genes that are required. Oct-3/4 and certain members of the Sox gene family have been identified as potentially crucial transcriptional regulators involved in the induction process. Additional genes including certain members of the Klf family, the Myc family, Nanog, and LIN28, may increase the induction efficiency. Examples of the genes which may be contained in the reprogramming factors include Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, San, Sall4, Esrrb, Nr5a2, Tbx3 and Glis1, and these reprogramming factors may be used singly, or in combination of two or more kinds thereof.

Where the aim is to produce stem cells with a gene knockdown or knock out for further research, such as developmental or gene function studies, the cell which is modified may be a stem cell, preferably a pluripotent stem cell, or a mature cell type. Sources of pluripotent stem cells are discussed above.

If the cells modified by insertion of an inducible cassette are to be used in a human patient, it may be preferred that the cell is an iPSC derived from that individual. Such use of autologous cells would remove the need for matching cells to a recipient. Alternatively, commercially available iPSC may be used, such as those available from WiCell® (WiCell Research Institute, Inc, Wisconsin, US). Alternatively, the cells may be a tissue-specific stem cell which may also be autologous or donated. Suitable cells include epiblast stem cells, induced neural stem cells and other tissue-specific stem cells.

In certain embodiments, it may be preferred that the cell used is an embryonic stem cell or stem cell line. Numerous embryonic stem cell lines are now available, for example, WA01 (H1) and WA09 (H9) can be obtained from WiCell, and KhES-1, KhES-2, and KhES-3 can be obtained from Institute for Frontier Medical Sciences, Kyoto University (Kyoto, Japan).

It may be preferred that the embryonic stem cell is derived without destruction of the embryo, particularly where the cells are human, since such techniques are readily available (Chung, Young et al., Cell Stem Cell, Volume 2, Issue 2, 113-117.) Stem cell lines which have been derived without destroying an embryo are also available. In one aspect, the invention does not extend to any methods which involve the destruction of human embryos.

A preferred aspect of the present invention is the forward programming of pluripotent stem cells into mature cell types. Thus, the method of the invention can be used for the manufacture of mature cell types from pluripotent stem cells. In this aspect of the invention, the inducible cassette for insertion into the second GSH is preferably one or more master regulators as discussed previously. These inducible cassettes may enable the cell to be programmed into a particular lineage, and different inducible cassettes will be used in order to direct differentiation into mature cell types. Any type of mature cell is contemplated, including but not limited to nerve cells, myocytes, osteocytes, chondrocytes, epithelial cells, secretory cells, and/or blood cells.

The inventors of the present application have developed a rapid, efficient and scalable method for the generation of virtually any mature cell type. Such a simple and cheap method will have particular value for regenerative medicine. Previous forward programming techniques utilised the Tet-On system, but attempted to include all the material into one vector/site (The all-in-one Tet-On) or tried to insert the inducible cassette into one AAVS1 allele and the control system into the other AAVS1 allele (DeKelver et al, 2010, Genome Res., 20, 1133-43 and Qian et al, 2014, Stem Cells, 32, 1230-8). Surprisingly, the dual GSH targeting method developed and described here has many unforeseen advantages. There is no potential promoter interference between the gene inserted in the first GSH and the genetic sequence of the inducible cassette inserted in the second GSH. Secondly, it allows the insertion of larger cargos from the vectors, since less material needs to be inserted at each site. Thirdly, the method maximises the number of safely inserted copies. Fourthly, it enables greater design flexibility. Finally, it allows for additional genetic material to be inserted, including reporter genes and miRNA switches. The method of the invention has been demonstrated to be a robust and efficient way of manufacturing mature cells from pluripotent cells.

Once the gene has been inserted into the first GSH and the inducible cassette comprising a transgene has been inserted into the second GSH, the pluripotent stem cells may be cultured to enable forward programming to take place. These culturing conditions may be specific for the type of pluripotent stem cell being used, or may depend upon the ultimate mature cell type. Whatever culturing conditions are used, the exogenous substance will control expression of the genetic sequence within the inducible cassette; and may either be supplied continuously and then withdrawn in order to induce transcription or supplied as transcription is required, dependent upon its mode of action, as previously discussed.

If the aim is to program a stem cell, it may be advantageous to provide that cell with extracellular prompts to aid differentiation in conjunction with the supply of inducible cassettes encoding master regulators. Cellular reprogramming strategies can be enhanced by combining master regulator or transcription factor overexpression with extracellular signalling cues. Thus, it may be possible to perform systematic screen for pro-differentiation factors by modulating major signalling cascades that are implicated in development of that particular mature cell type. An instance of this is seen in Example 3.

In one aspect, the present invention provides a method for the production of myocytes from pluripotent stem cells, comprising the steps of:
 a) targeted insertion of a gene encoding a transcriptional regulator protein into a first genetic safe harbour site; and
 b) targeted insertion of the MYOD1 gene operably linked to an inducible promoter into a second genetic safe harbour site, wherein said inducible promoter is regulated by the transcriptional regulator protein; wherein said first and second genetic safe harbour sites are different,
and culturing said cells in the presence of retinoic acid.

The MYOD1 gene is the gene encoding the Myogenic Differentiation 1 protein. Preferably, the retinoic acid (RA) is all-trans RA.

In another aspect, the present invention provides a method for the production of myocytes from pluripotent stem cells expressing MYOD1, comprising culturing said cells in the presence of retinoic acid.

Preferably, the RA is all-trans RA. Preferably, the cell is overexpressing MYOD1.

In a further aspect, the present invention provides a method for the production of oligodendrocytes myocytes from pluripotent stem cells, comprising the steps of:
 a) targeted insertion of a gene encoding a transcriptional regulator protein into a first genetic safe harbour site; and
 b) targeted insertion of the SOX 10 gene operably linked to an inducible promoter into a second genetic safe harbour site, wherein said inducible promoter is regulated by the transcriptional regulator protein; wherein said first and second genetic safe harbour sites are different,
and culturing said cells in the presence of retinoic acid.

The cells used for this may be animal or human cells. If the cells are animal, it is preferred that the animal is a livestock animal as previously defined.

The SOX-10 gene encodes the transcription factor SOX-10. Preferably, the retinoic acid (RA) is all-trans RA.

Where the cell used in the methods of the invention is pluripotent, the resultant cell may be a lineage restricted-specific stem cell, progenitor cell or a mature cell type with the desired properties, by expression of a master regulator. These lineage-specific stem cells, progenitor or mature cells may be used in any suitable fashion. For example, the mature cells may be used directly for transplantation into a human or animal body, as appropriate for the cell type. Alternatively, the cells may form a test material for research, including the effects of drugs on gene expression and the interaction of drugs with a particular gene. The cells for research can involve the use of an inducible cassette with a genetic sequence of unknown function, in order to study the controllable expression of that genetic sequence. Additionally, it may enable the cells to be used to produce large quantities of desirable materials, such as growth factors or cytokines.

In a different aspect, the cells may be used in tissue engineering. Tissue engineering requires the generation of tissue which could be used to replace tissues or even whole organs of a human or animal. Methods of tissue engineering are known to those skilled in the art, but include the use of a scaffold (an extracellular matrix) upon which the cells are applied in order to generate tissues/organs. These methods can be used to generate an "artificial" windpipe, bladder, liver, pancreas, stomach, intestines, blood vessels, heart tissue, bone, bone marrow, mucosal tissue, nerves, muscle, skin, kidneys or any other tissue or organ. Methods of generating tissues may include additive manufacturing, otherwise known as three-dimensional (3D) printing, which can involve directly printing cells to make tissues. The present invention thus provides a method for generating tissues using the cells produced as described in any aspect of the invention.

Tissues generated using cells made according to the methods of the present invention may be used for transplantation into the human or animal body. Alternatively, if the cells are from an animal, the tissues may be used for in vitro/cultured meat. The primary cell type for cultured meat is myocytes. Such tissue may, however, involve the use of a combination of cell types made according to the methods of the invention.

These may be myocytes (muscle cells), blood vessel cells, blood cells and adipocytes (fat cells). If the aim of the engineered tissue is for cultured meat, then the cell may be taken from a livestock animal.

The methods of the invention may also be performed on cells which are not pluripotent stem cells, for a variety of reasons, including research, gene therapy including genetic vaccines, production of in vitro disease models and production of non-human in vivo models.

The cells used in the method of the invention may thus be any type of adult stem cells; these are unspecialised cells that can develop into many, but not all, types of cells. Adult stem cells are undifferentiated cells found throughout the body that divide to replenish dying cells and regenerate damaged tissues. Also known as somatic stem cells, they are not pluripotent. Adult stem cells have been identified in many organs and tissues, including brain, bone marrow, peripheral blood, blood vessels, skeletal muscle, skin, teeth, heart, gut, liver, ovarian epithelium, and testis. In order to label a cell a somatic stem cell, the skilled person must demonstrate that a single adult stem cell can generate a line of genetically identical cells that then gives rise to all the appropriate differentiated cell types of the tissue. To confirm experimentally that a putative adult stem cell is indeed a stem cell, the cell must either give rise to these genetically identical cells in culture, or a purified population of these cells must repopulate tissue after transplantation into an animal. Suitable cell types include, but are not limited to neural, mesenchymal and endodermal stem and precursor cells.

Alternatively, the cells used may be a mature cell type. Such cells are differentiated and specialised and are not able to develop into a different cell type. Mature cell types include, but are not limited to nerve cells, myocytes, osteocytes, chondrocytes, epithelial cells, secretory cells, and/or blood cells. Mature cell types could be any cell from the human or animal body.

Somatic stem cells and mature cell types may be modified according to the present invention and then used for applications such as gene therapy or genetic vaccination. Gene therapy may be defined as the intentional insertion of foreign DNA into the nucleus of a cell with therapeutic intent. Such a definition includes the provision of a gene or genes to a cell to provide a wild type version of a faulty gene, the addition of genes for RNA molecules that interfere with target gene expression (which may be defective), provision of suicide genes (such as the enzymes herpes simplex virus thymidine kinase (HSV-tk) and cytosine deaminase (CD) which convert the harmless prodrug ganciclovir (GCV) into a cytotoxic drug), DNA vaccines for immunisation or cancer therapy (including cellular adoptive immunotherapy) and any other provision of genes to a cell for therapeutic purposes.

Typically, the method of the invention may be used for insertion of a desired genetic sequence for transcription in a cell, preferably expression, particularly in DNA vaccines. DNA vaccines typically encode a modified form of an infectious organism's DNA. DNA vaccines are administered to a subject where they then express the selected protein of the infectious organism, initiating an immune response against that protein which is typically protective. DNA vaccines may also encode a tumour antigen in a cancer immunotherapy approach.

A DNA vaccine may comprise a nucleic acid sequence encoding an antigen for the treatment or prevention of a number of conditions including but not limited to cancer, allergies, toxicity and infection by a pathogen such as, but not limited to, fungi, viruses including Human Papilloma Viruses (HPV), HIV, HSV2/HSV1, Influenza virus (types A, B and C), Polio virus, RSV virus, Rhinoviruses, Rotaviruses, Hepatitis A virus, Measles virus, Parainfluenza virus, Mumps virus, Varicella-Zoster virus, Cytomegalovirus, Epstein-Barr virus, Adenoviruses, Rubella virus, Human T-cell Lymphoma type I virus (HTLV-I), Hepatitis B virus (HBV), Hepatitis C virus (HCV), Hepatitis D virus, Pox virus, Zika virus, Marburg and Ebola; bacteria including *Meningococcus, Haemophilus influenza* (type b); and parasitic pathogens. DNA vaccines may comprise a nucleic acid sequence encoding an antigen from any suitable pathogen. The antigen may be from a pathogen responsible for a human or veterinary disease and in particular may be from a viral pathogen.

DNA vaccines inserted into the GSH may also comprise a nucleic acid sequence encoding tumour antigens. Examples of tumour associated antigens include, but are not limited to, cancer-antigens such as members of the MAGE family (MAGE 1, 2, 3 etc.), NY-ESO-I and SSX-2, differentiation antigens such as tyrosinase, gplOO, PSA, Her-2 and CEA, mutated self-antigens and viral tumour antigens such as E6 and/or E7 from oncogenic HPV types. Further examples of particular tumour antigens include MART-I, Melan-A, p97, beta-HCG, GalNAc, MAGE-I, MAGE-2, MAGE-4, MAGE-12, MUCI, MUC2, MUC3, MUC4, MUC18, CEA, DDC, PIA, EpCam, melanoma antigen gp75, Hker 8, high molecular weight melanoma antigen, KI 9, Tyr1, Tyr2, members of the pMel 17 gene family, c-Met, PSM (prostate mucin antigen), PSMA (prostate specific membrane antigen), prostate secretary protein, alpha-fetoprotein, CA 125, CA 19.9, TAG-72, BRCA-I and BRCA-2 antigen.

The inserted genetic sequence may produce other types of therapeutic DNA molecules. For example, such DNA molecules can be used to express a functional gene where a subject has a genetic disorder caused by a dysfunctional version of that gene. Examples of such diseases include Duchenne muscular dystrophy, cystic fibrosis, Gaucher's Disease, and adenosine deaminase (ADA) deficiency. Other diseases where gene therapy may be useful include inflammatory diseases, autoimmune, chronic and infectious diseases, including such disorders as AIDS, cancer, neurological diseases, cardiovascular disease, hypercholestemia, various blood disorders including various anaemias, thalassemia and haemophilia, and emphysema. For the treatment of solid tumours, genes encoding toxic peptides (i.e., chemotherapeutic agents such as ricin, diphtheria toxin and cobra venom factor), tumour suppressor genes such as p53, genes coding for mRNA sequences which are antisense to transforming oncogenes, antineoplastic peptides such as tumour necrosis factor (TNF) and other cytokines, or transdominant negative mutants of transforming oncogenes, may be expressed.

Other types of therapeutic DNA molecules are also contemplated. For example, DNA molecules which are transcribed into an active, non-coding RNA form, for example a small interfering RNA (siRNA) may be inserted. The methods of the invention thus extend to methods of knocking down endogenous gene expression or knocking out endogenous genes using non-coding RNAs within the inducible cassette.

Thus, the method of the invention may be used to specifically and stably insert a genetic sequence within the inducible cassette which may be controllably transcribed. This has numerous advantages in somatic stem cells and mature cell types. It allows for more closely regulated gene therapy approaches, ensuring that critical genes are not disrupted and allowing the expression of the inducible cassette to be turned off if any adverse effects occur. It also allows for closely regulated endogenous gene knockdown or knockout, in order to interrogate gene function and development.

The invention extends to the cells produced by the method of the invention. The cells may be defined as being modified at a first genomic safe harbour site to include a transcriptional regulator protein and at a second genetic safe harbour site to include a genetic sequence operably linked to an inducible promoter which is regulated by the transcriptional regulator protein. The two GSH are different and distinct. Preferably the cells are homozygous at both insertion sites. All elements are as previously described.

The cells produced according to any of the methods of the invention have applications in diagnostic and therapeutic methods. The cells may be used in vitro to study cellular development, provide test systems for new drugs, enable screening methods to be developed, scrutinise therapeutic regimens, provide diagnostic tests and the like. These uses form part of the present invention. Alternatively, the cells may be transplanted into a human or animal patient for diagnostic or therapeutic purposes. The use of the cells in therapy is also included in the present invention. The cells may be allogeneic (i.e. mature cells removed, modified and returned to the same individual) or from a donor (including a stem cell line).

All documents referred to herein are hereby incorporated by reference.

Figure 18:
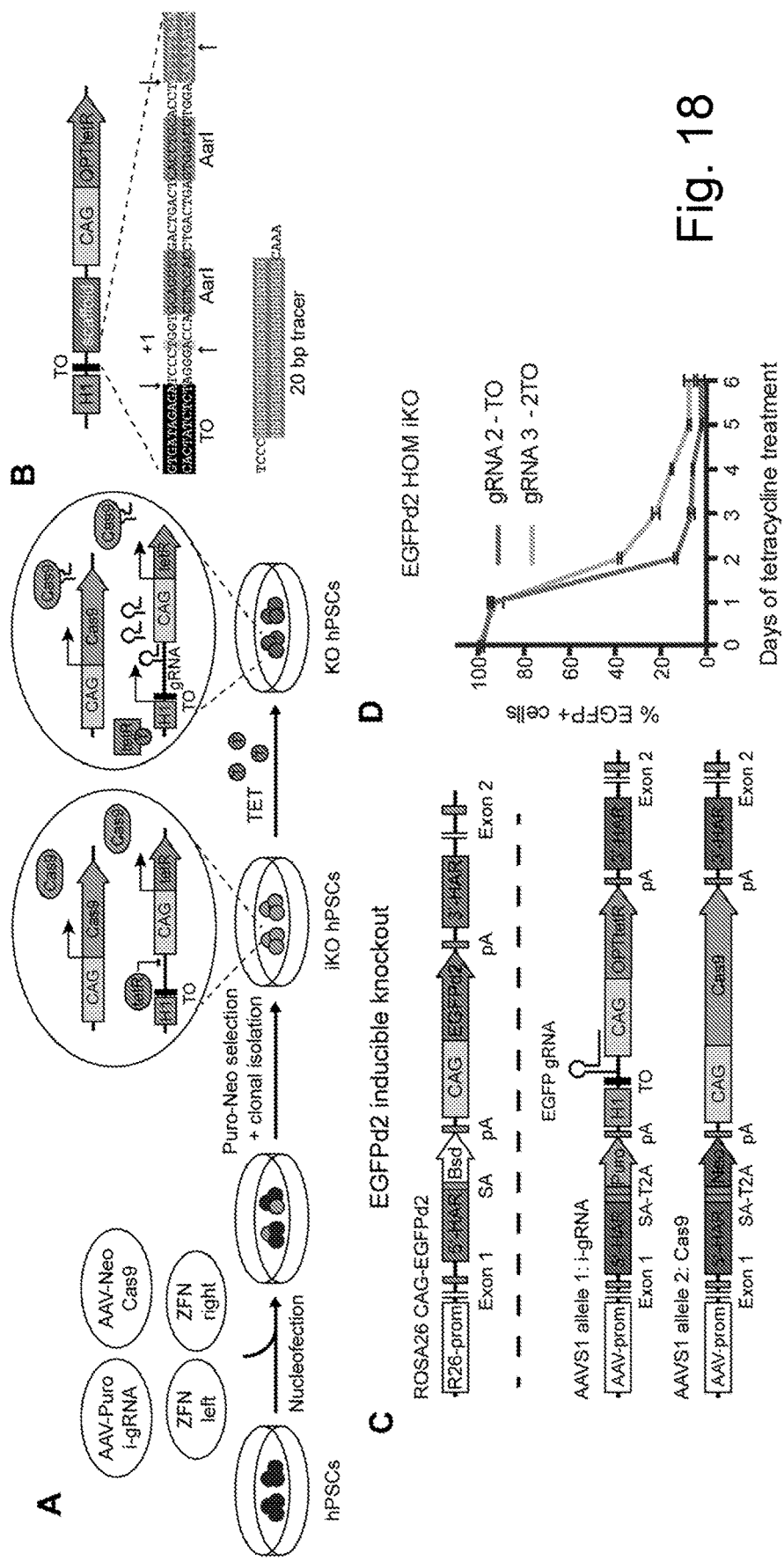
FIG. 18 (a-d). Development of an optimized inducible CRISPR/Cas9 knockout platform in hPSCs.
Figure 19:
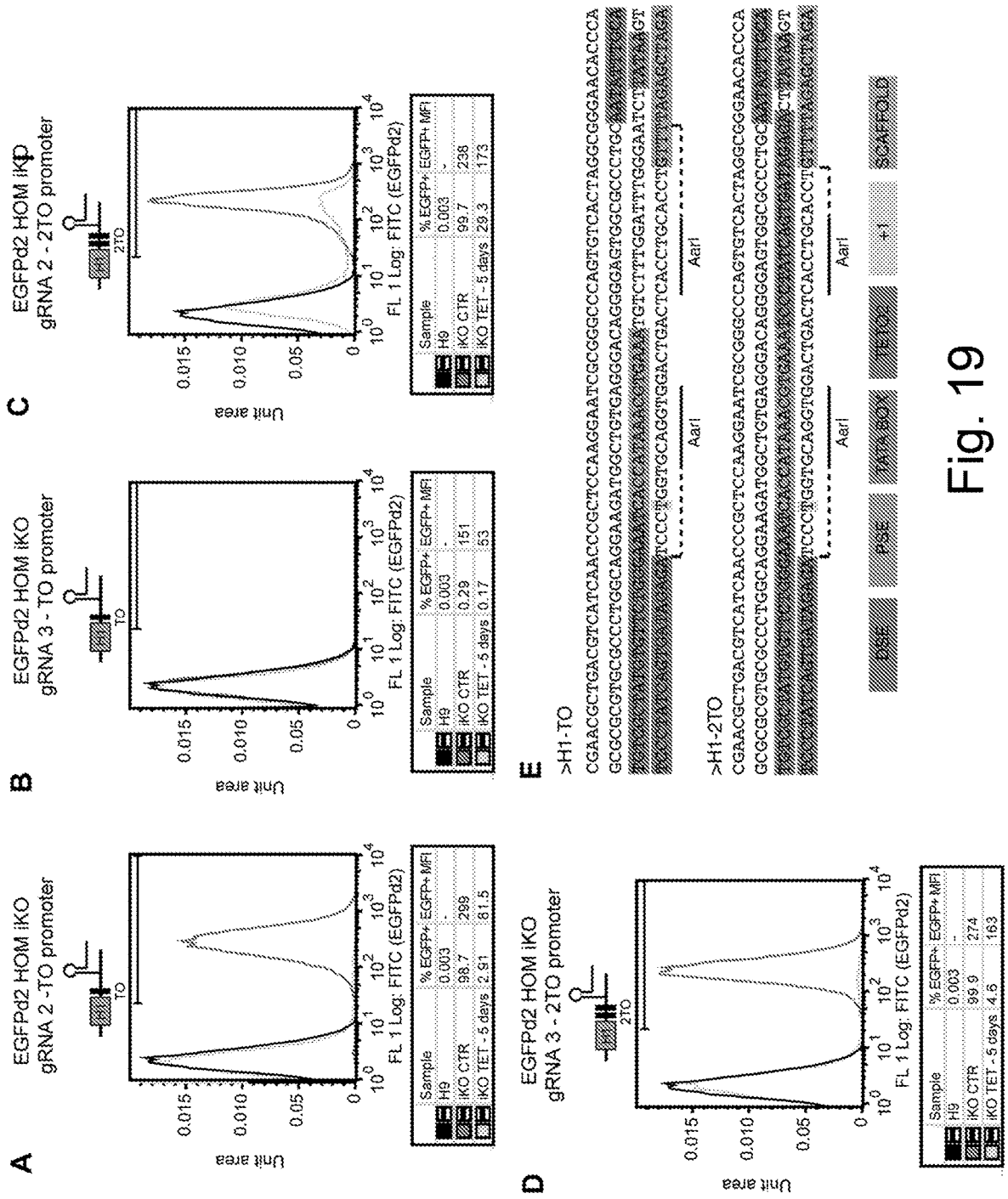
FIG. 19 (a to e): Development of an optimized inducible CRISPR/Cas9 knockout platform in hESCs. (A-D) depict representative flow cytometry for EGFPd2 expression in EGFPd2 homozygous sOPTiKO hESCs carrying the indicated combinations of gRNA (2 or 3) and inducible promoter (TO or 2TO, see FIG. 19 e). Targeting vectors: pAAV-Puro_siKOEGFP-2 (19a), pAAV-Puro_siKO-2TO-EGFP-2 (19b), pAAV-Puro_siKO-EGFP-3 (19c), pAAV-Puro_siKO-2TO-EGFP-3 (19d). Cells were cultured in presence of tetracycline (TET) for 5 days, or maintained in control (CTR) conditions in the absence of tetracycline. Note that the histograms have been normalized so that the area under the curve equals to 1 (100%) for all samples presented, in order to facilitate direct visual comparison.

Sequences
AAVS1—NCBI GenBank 551329.1
SEQ ID No 1: Tet02 19n sequence
SEQ ID No 2: hROSA insertion site genomic sequence
SEQ ID No 3: STDtetR-nls (nucleotide) and SEQ ID No 4—STDtetR-nls (amino acid)
SEQ ID No 5: OPTtetR-nls (nucleotide) and SEQ ID No 6—OPTtetR-nls (amino acid)
SEQ ID No 7 to 80: Primers from table 3.
SEQ ID No 81: FIG. 18B AAVS1 FWD; SEQ ID No 82: FIG. 18B AAVS1 REV
SEQ ID No 83: FIG. 18B tracer FWD; SEQ ID No 84: FIG. 18B tracer REV
SEQ ID No 85: FIG. 19E HI POL3 FWD; SEQ ID No 82: FIG. 19E HI POL3 REV This is the genomic sequence of the hROSA26 insertion site; it includes the 5' homology arm, the cut site (bold), and the 3' homology arm: (SEQ ID NO 2)

```
GCTCGAAACCGGACGGAGCCATTGCTCTCGCAGAGGGAGGAGCGCTTCCG
GCTAGCCTCTTGTCGCCGATTGGCCGTTTCTCCTCCCGCCGTGTGTGAAA
ACACAAATGGCGTATTCTGGTTGGAGTAAAGCTCCTGTCAGTTACGCCGT
CGGGAGTACGCAGCCGCTTAGCGACTCTCGCGTTGCCCCCTGGGTGGGGC
GGGTAGGTAGGTGGGGTGTAGAGATGCTGGGTGTGCGGGCGCGGCCGGCC
TCCTGCGGCGGGAGGGGAGGGTCAGTGAAATCGGCTCTGGCGCGGGCGTC
CTCCCACCCTCCCCTTCCTTCGGGGGAGTCGGTTTACCCGCCGCCTGCTT
GTCTTCGACACCTGATTGGCTGTCGAAGCTGTGGGACCGGGCCCTTGCTA
CTGGCTCGAGTCTCACATGAGCGAAACCACTGCGCGGGGCGCGGGGGTGG
CGGGGAGGCGGGCGTTGGTACGGTCCTCCCCGAGGCCGAGCGCCGCAGTG
TCTGGCCCCGCGCCCCTGCGCAACGTGGCAGGAAGCGCGCGCTGGAGGCG
GGGGCGGGCTGCCGGCCGAGACTTCTGGATGGCGGCGGCCGCGGCTCCGC
CCCGGGTTCCCACCGCCTGAAGGGCGAGACAAGCCCGACCTGCTACAGGC
ACTCGTGGGGTGGGGAGGAGCGGGGGTCGGTCCGGCTGGTTTGTGGGT
GGGAGGCGCTTGTTCTCCAAAAACCGGCGCGAGCTGCAATCCTGAGGGAG
CTGCGGTGGAGGAGGTGGAGAGAAGGCCGCACCCTTCTGGGCAGGGGGAG
GGGAGTGCCGCAATACCTTTATGGGAGTTCTCTGCTGCCTCCCGTCTTGT
AAGGACCGCCCTGGGCCTGGAAGAAGCCCTCCCTCCTTTCCTCCT
```
CGCGT
GATCTCGTCATCGCCTCCATGTCGAGTCGCTTCTCGATTATGGCGGGAT

```
TCTTTTGCCTAGGCTTAAGGGGCTAACTTGGTCCCTGGGCGTTGCCCTGC
AGGGGAGTGAGCAGCTGTAAGATTTGAGGGGCGACTCCGATTAGTTTATC
TTCCCACGGACTAGAGTTGGTGTCGAGGTTATTGTAATAAGGGTGGGGTA
GGGAAATGGAGCTTAGTCATTCACCTGGGGCTGATTTTATGCAACGAGAC
TGCGGATTATCACTACTTATCATTTTTGGAGCATTTTTCTAGAGACAGAC
ATAAAGCATGATCACCTGAGTTTTATACCATTTGAGACCCTTGCTGCACC
ACCAAAGTGTAGCATCAGGTTAAATCTTAATAGAAAAATTTTAGCTTTTG
CTTGAGAAACCAGTGCTTCCCTCCCTCACCCTCTCTCCCCAGGCTCTCTA
CCCCTTTGCATCCCTACCAGGCATCTTAGCAACTCTCACTCATACTTGAT
CCCATTTTCCATTTGTTGTACTTGCTCCTCTAGTATTCAGACATAGCACT
AGCTTTCTCCCTCTCTTGATCTTGGGTAGCCTGGTGTCTCGCGAAACCAG
ACAGATTGGTTCCACCACAAATTAAGGCTTGAGCTGGGGCTTGACTCTTA
CCCAGCAGTGCTTTTATTCCTCCCTAGTTCACGTTCTTAAATGTTTATCT
TGATTTTCATTTTATCCTTTTTCCTTAGCTGGGATTCTGTCCCTGACCGT
CTTCACAGTCCAGGTGATCTTGACTACTGCTTTACAGAGAATTGGATCTG
AGGTTAGGCAACATCTCCCTTTTTCTTCCTCTAAATACCTCTCATTTCTG
TTCTTACCAGTTAGTAACTGATCTCAGATGCCTGTGTGATAGCTTCC
```

STDtetR-nls: (SEQ ID No 3 and 4)
Nucleotide and amino acid sequences of the tetracycline-sensitive repressor protein (tetR) containing an N-terminal SV40 nuclear localization signal (nls, highlighted in grey). Sequences are reported either before or after codon optimization (STDtetR and OPTtetR, respectively). Dots indicate the synonymous mutations introduced in the OPTtetR.

```
ATGCCAAAAAAGAAGAGGAAGGTATCTAGATTAGATAAAAGTAAAGTGATTAACAGCGCATTAGAGC
 M  P  K  K  K  R  K  V  S  R  L  D  K  S  K  V  I  N  S  A  L  E  L

TGCTTAATGAGGTCGGAATCGAAGGTTTAACAACCCGTAAACTCGCCCAGAAGCTAGGTGTAGAGCA
 L  N  E  V  G  I  E  G  L  T  T  R  K  L  A  Q  K  L  G  V  E  Q

GCCTACATTGTATTGGCATGTAAAAAATAAGCGGGCTTTGCTCGACGCCTTAGCCATTGAGATGTTA
 P  T  L  Y  W  H  V  K  N  K  R  A  L  L  D  A  L  A  I  E  M  L

GATAGGCACCATACTCACTTTTGCCCTTTAGAAGGGGAAAGCTGGCAAGATTTTTTACGTAATAAGC
 D  R  H  H  T  H  F  C  P  L  E  G  E  S  W  Q  D  F  L  R  N  N  A

CTAAAAGTTTTAGATGTGCTTTACTAAGTCATCGCGATGGAGCAAAAGTACATTTAGGTACACGGCC
 K  S  F  R  C  A  L  L  S  H  R  D  G  A  K  V  H  L  G  T  R  P

TACAGAAAAACAGTATGAAACTCTCGAAAATCAATTAGCCTTTTTATGCCAACAAGGTTTTTCACTA
 T  E  K  Q  Y  E  T  L  E  N  Q  L  A  F  L  C  Q  Q  G  F  S  L

GAGAATGCATTATATGCACTCAGCGCTGTGGGGCATTTTACTTTAGGTTGCGTATTGGAAGATCAAG
 E  N  A  L  Y  A  L  S  A  V  G  H  F  T  L  G  C  V  L  E  D  Q  E

AGCATCAAGTCGCTAAAGAAGAAAGGGAAACACCTACTACTGATAGTATGCCGCCATTATTACGACA
 H  Q  V  A  K  E  E  R  E  T  P  T  T  D  S  M  P  P  L  L  R  Q

AGCTATCGAATTATTTGATCACCAAGGTGCAGAGCCAGCCTTCTTATTCGGCCTTGAATTGATCATA
 A  I  E  L  F  D  H  Q  G  A  E  P  A  F  L  F  G  L  E  L  I  I

TGCGGATTAGAAAAACAACTTAAATGTGAAAGTGGGTCTCCGCGGTAA
 C  G  L  E  K  Q  L  K  C  E  S  G  S  P  R  *
```

The sequence for optimised tetR: OPTtetR-nls (SEQ ID NO 5 and 6):

```
ATGCCCAAGAAAAAGCGGAAGGTGTCCCGGCTGGACAAGAGCAAAGTGATCAACAGCGCCCTGGAAC
 M  P  K  K  K  R  K  V  S  R  L  D  K  S  K  V  I  N  S  A  L  E  L

TGCTGAACGAAGTGGGCATCGAGGGCCTGACCACCCGGAAGCTGGCCCAGAAACTGGGCGTGGAACA
 L  N  E  V  G  I  E  G  L  T  T  R  K  L  A  Q  K  L  G  V  E  Q

GCCCACCCTGTACTGGCACGTGAAGAACAAGCGGGCCCTGCTGGACGCCCTGGCCATCGAGATGCTG
 P  T  L  Y  W  H  V  K  N  K  R  A  L  L  D  A  L  A  I  E  M  L

GACCGGGCACCACACACACTTTGCCCCCTGGAAGGCGAAAGCTGGCAGGACTTCCTGCGGAACAACG
 D  R  H  H  T  H  F  C  P  L  E  G  E  S  W  Q  D  F  L  R  N  N  A

CCAAGAGCTTCAGATGCGCCCTGCTGAGCCACCGGGACGGCGCCAAAGTGCACCTGGGCACCAGACC
 K  S  F  R  C  A  L  L  S  H  R  D  G  A  K  V  H  L  G  T  R  P

CACCGAGAAGCAGTACGAGACACTGGAAAACCAGCTGGCCTTCCTGTGCCAGCAGGGCTTCAGCCTG
 T  E  K  Q  Y  E  T  L  E  N  Q  L  A  F  L  C  Q  Q  G  F  S  L

GAAAACGCCCTGTACGCCCTGAGCGCCGTGGGCCACTTTACCCTGGGCTGCGTGCTGGAAGATCAGG
 E  N  A  L  Y  A  L  S  A  V  G  H  F  T  L  G  C  V  L  E  D  Q  E

AACACCAGGTCGCCAAAGAGGAAAGAGAGACACCCACCACCGACAGCATGCCCCCCCTGCTGAGACA
 H  Q  V  A  K  E  E  R  E  T  P  T  T  D  S  M  P  P  L  L  R  Q

GGCCATCGAGCTGTTCGATCATCAAGGCGCCGAGCCCGCCTTCCTGTTCGGCCTGGAACTGATCATC
 A  I  E  L  F  D  H  Q  G  A  E  P  A  F  L  F  G  L  E  L  I  I

TGCGGCCTCGAGAAGCAGCTGAAGTGCGAGAGCGGCTCCCCCAGATGA
 C  G  L  E  K  Q  L  K  C  E  S  G  S  P  R  *
```

The invention will now be described in relation to the following non-limiting examples:

EXAMPLES

Materials and Methods Used in the Examples:

hPSC Maintenance Culture and Germ Layer Differentiation

Feeder- and serum-free hESC (H9 line; WiCell) and hiPSC (Cheung et al, Nat. Biotechnol. 30, 165-173 (2012)) culture was performed. Briefly, cells were plated on gelatin/MEF media-coated culture dishes [MEF-media consisted of Advanced DMEM/F12 (90%, Gibco), fetal bovine serum (10%, Gibco), L-Glutamine (1 mM, Gibco), 2-Mercaptoethanol (0.1 mM, Sigma-Aldrich) and Penicillin/Streptomycin (1%, Gibco)], and cultured in chemically defined media [CDM, consisting of IMDM (50%, Gibco), F12 (50%, Gibco), concentrated lipids (100×, Gibco), monothioglycerol (450 µM, Sigma-Aldrich), insulin (7 µg/ml, Roche), transferrin (15 µg/ml, Roche), bovine serum albumin fraction V (5 mg/ml), and Penicillin/Streptomycin (1%)] supplemented with 10 ng/ml Activin-A and 12 ng/ml FGF2. Cells were passaged in small clumps using collagenase every 5-6 days.

Differentiation of hPSCs into the germ layers was induced in adherent hESC cultures according to previously published directed differentiation protocols for endoderm, lateral plate mesoderm, and neuroectoderm (Touboul, T. et al. Hepatology 51, 1754-1765 (2010), Cheung et al, (2012) and Douvaras, P. et al. Stem Cell Reports 3, 250-259 (2014).) Briefly, definitive endoderm was derived by culturing hPSCs for 3 days in CDM-PVA (without insulin) supplemented with FGF2 (20 ng/ml), Activin-A (100 ng/ml), BMP4 (10 ng/ml, Marko Hyvonen, Dept. of Biochemistry, University of Cambridge), and LY-294002 (10 µM, Promega) 3. For derivation of neuroectoderm, hPSCs were cultured for 6 days in CDM-BSA supplemented with SB-431542 (10 µM, Tocris), LDN-193189 (0.1 µM, Tocris) and RA (0.1 µM, Sigma) 4. Lateral plate mesoderm was obtained by culturing hPSCs for 36 h in CDMPVA supplemented with FGF2 (20 ng/ml), 10 ng/ml BMP4 (R&D), and LY294002 (10 µM), and for 3.5 subsequent days in CDM-PVA supplemented with FGF2 (20 ng/ml) and BMP4 (50 ng/ml).

Differentiation of hESCs. Differentiation was initiated in adherent cultures of hESCs 48 h following passaging. Media changes were generally performed daily, and volumes were adjusted for cell density. Mature cell types were obtained using methods previously described in the art. Mature cell types obtained included neural cells, osteocytes, chondrocytes, smooth muscle, cardiac fibroblasts, cardiomyocytes, intestine, pancreas, hepatocytes, cholangiocytes or lung.

Gene Targeting Constructs and Molecular Cloning

Figure 20:
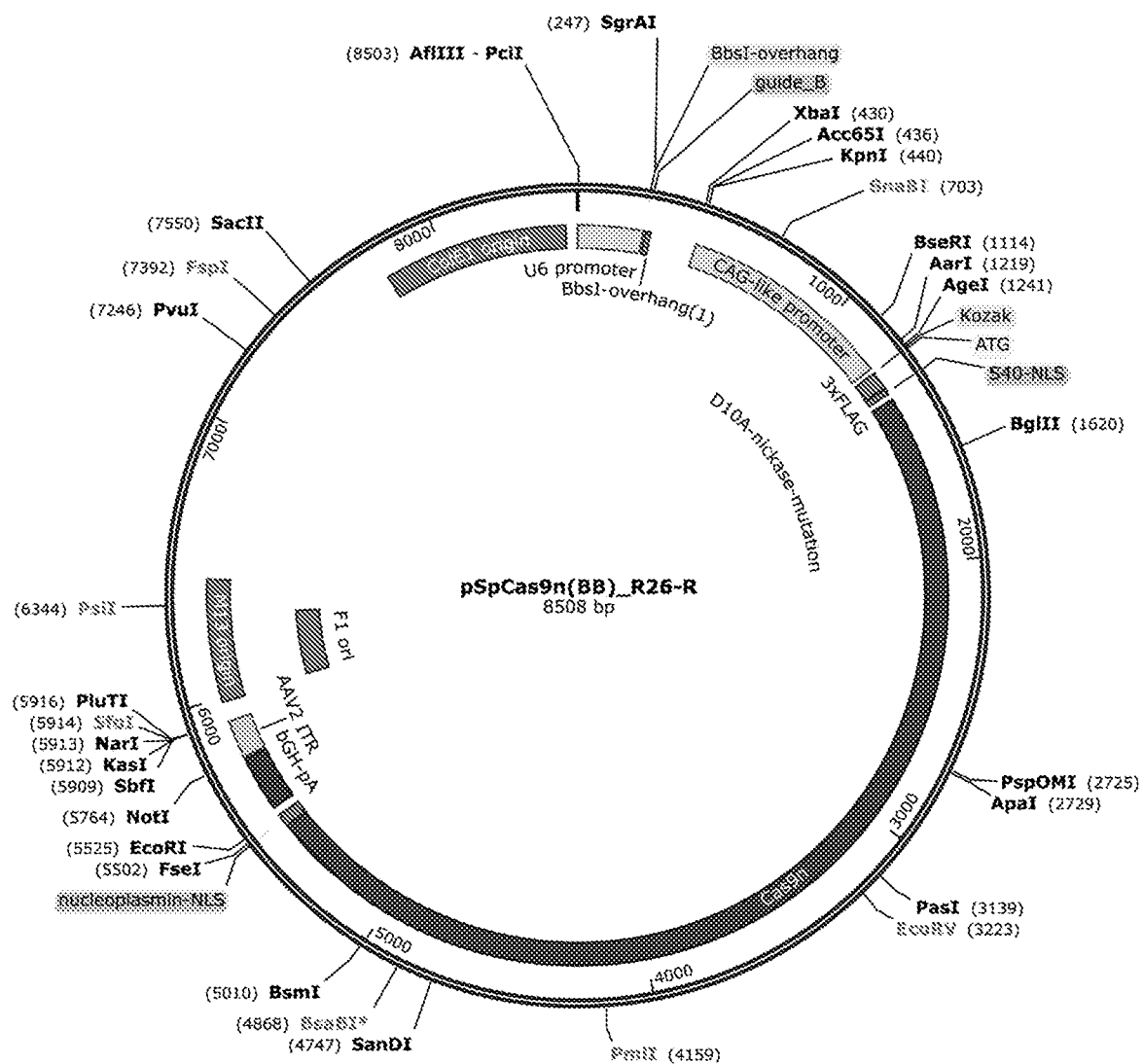
FIGS. 20 to 33 are depictions of the maps of various plasmids used within the Examples of the present application. These are:
20) pSpCas9n(BB)_R26-R
21) pSpCas9n(BB)_R26-L
22) pR26_CAG_EGFP
23) pR26_CAG_rtTA
24) pZFN-AAVS1-L-ELD (zinc finger nuclease left)
25) pZFN-AAVS1-R-KKR (zinc finger nuclease right)
26) pAAV_CAG_EGFP (donor)
27) pR26-Neo_CAG-OPTtetR (hROSA26 targeting of codon-optimized tetR)
28) pAAV-Puro_iKD (AAVS1 targeting of inducible shRNA)
29) pAAV-Neo_CAG-Cas9 (AAVS1 targeting of Cas9)
30) pAAV-Puro_siKO (AAVS1 targeting of inducible gRNA,)
31) pAAV-Puro_siKO-2TO (AAVS1 targeting of inducible gRNA, version with 2 tet operons in promoter)
32) pAAV_TRE-EGFP (EGFP inducible overexpression, attached)
33) pAAV_TRE-MYOD1 (MYOD1 inducible overexpression for muscle)
Figure 21:
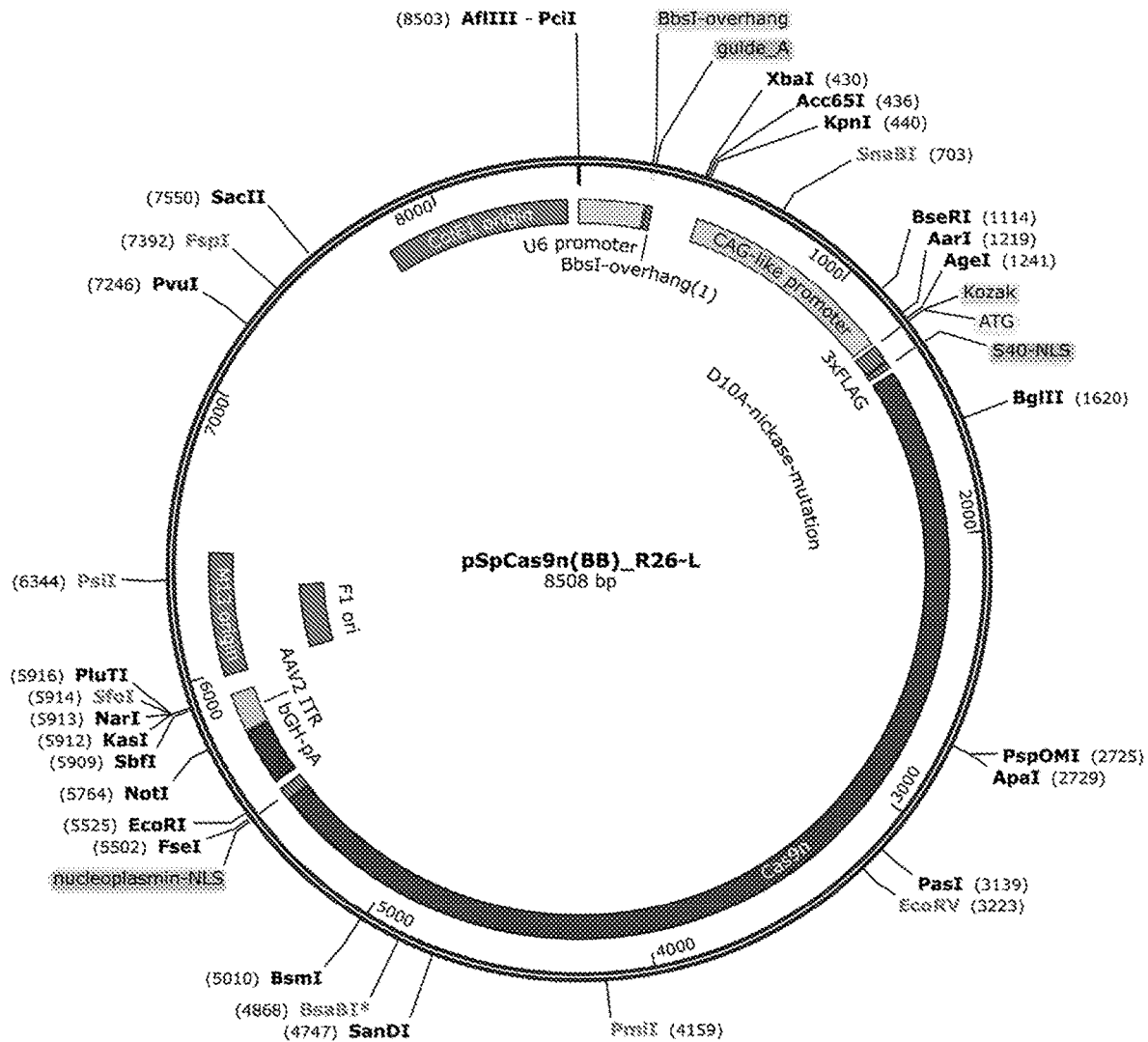

Design and construction of the hROSA26 gRNA and Cas9n expression plasmids is described here: A CRISPR/Cas9n based strategy to specifically target the hROSA26 locus and to insert inducible cassettes using homologous recombination. To induce a genomic DSB at the correct integration site, a CRISPR/Cas9 nickase system was designed. In contrast to the commonly used wild-type Cas9 nuclease which is let by a single gRNA to its genomic target site, the D10A mutant Cas9 nickase (Cas9n) is directed by a pair of appropriately designed gRNAs to simultaneously introduce single-stranded cuts on both strands of the target DNA. This strategy effectively doubles the number of bases required for genome editing and thereby increases specificity. The web-based software "CRISPR Design Tool" was used to define potential target sites for crRNA-guided nucleases that are close to the integration site. Within a sequence stretch of 250 bp around the target site (125 bp on each site of the actual integration site), the top hit yielded a pair of gRNAs that collectively reached a "high quality" score of 97, with no predicted off target effects. The gRNAs [gRNA-A 5'-GTCGAGTCGCTTCTCGATTA-(TGG)-3' (SEQ ID NO: 87) and gRNA-B 5'-GGCGATGACGAGAT-CACGCG-(AGG)-3' (SEQ ID NO: 88) (PAM sites in parenthesis) were synthesised de novo and ligated into expression vectors. The final plasmids encode for either of the two gRNAs, respectively, and the Cas9n D10A-mutant (FIGS. 20 and 21).

Figure 22:
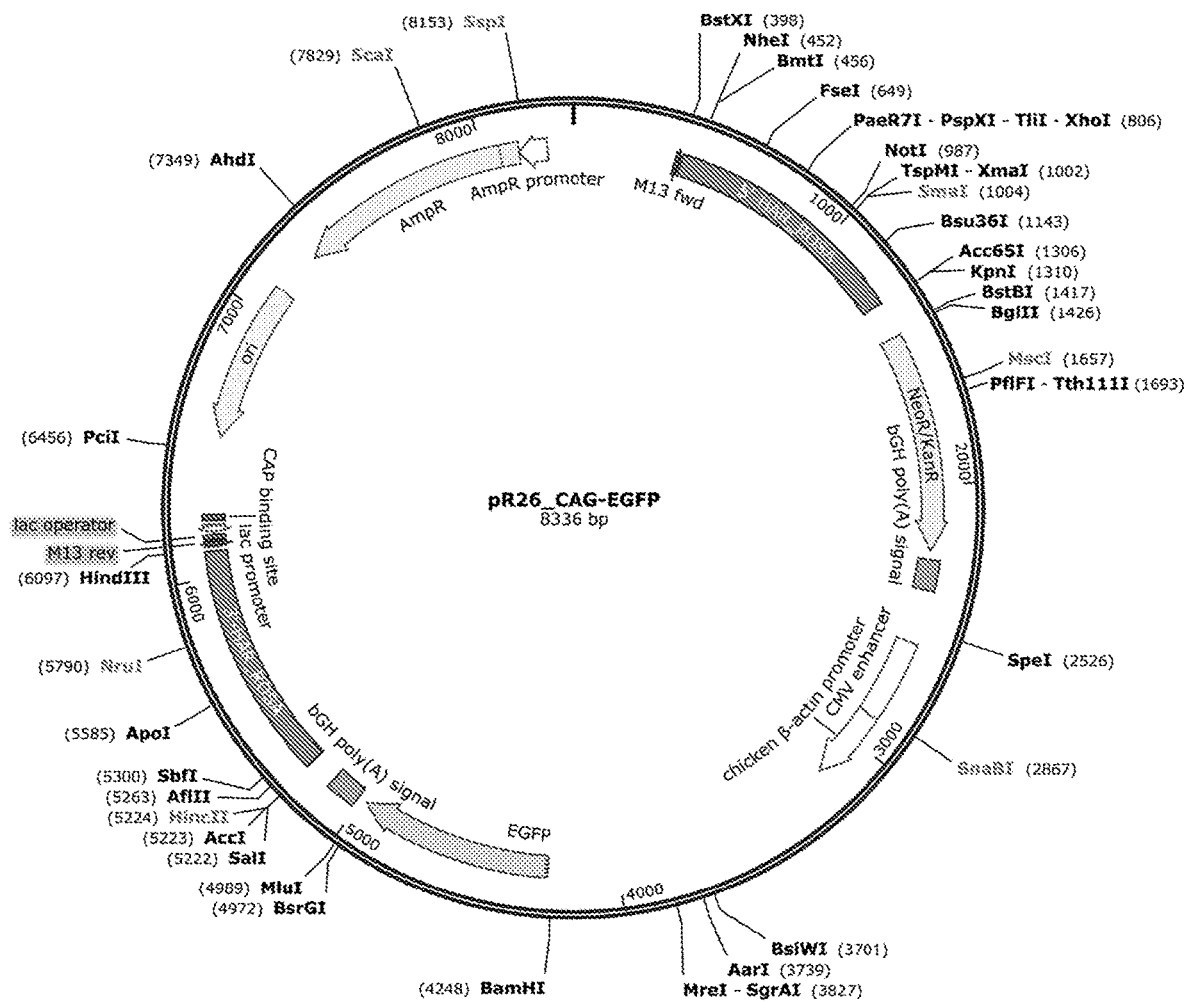
Figure 23:
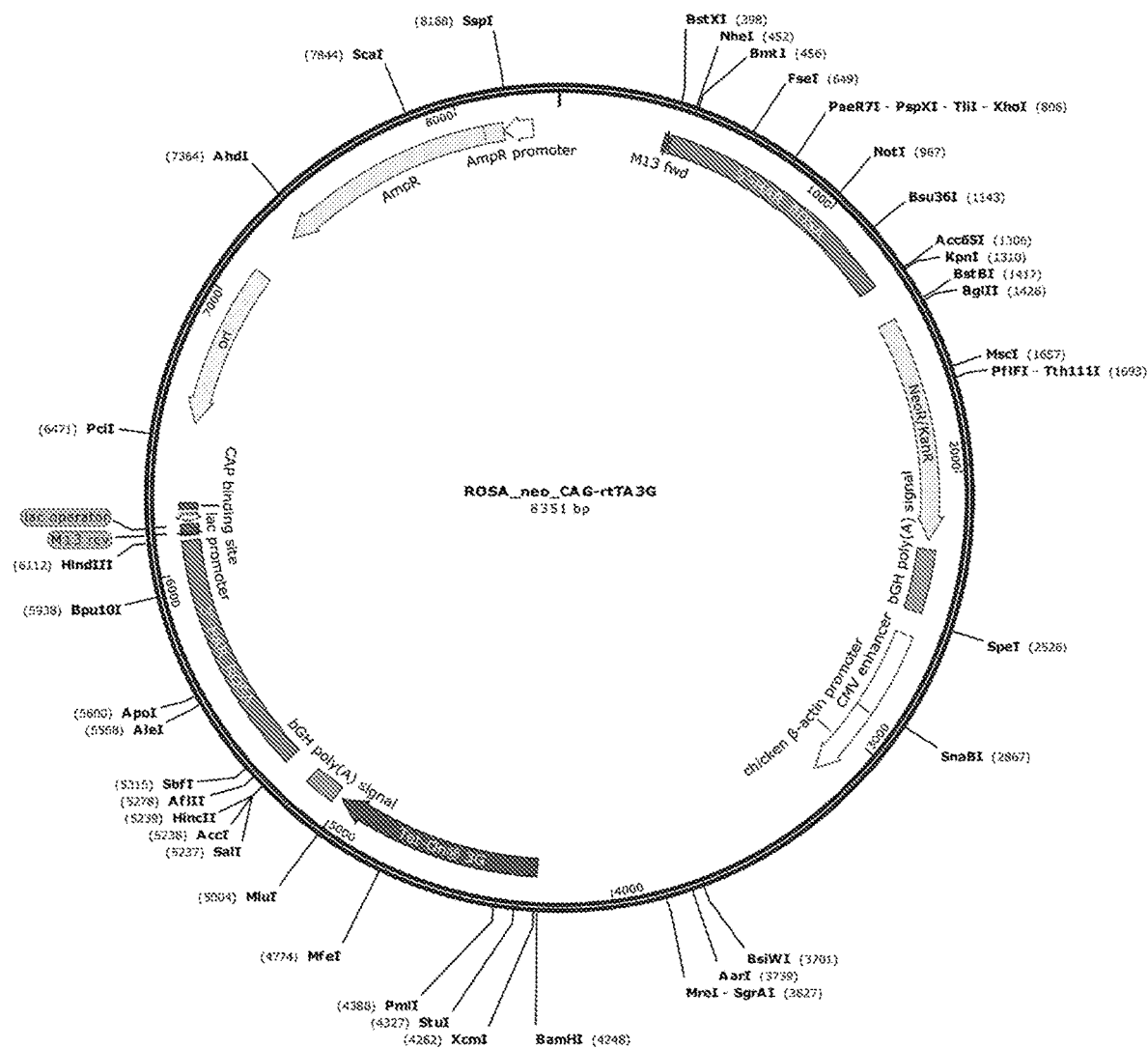
Figure 24:
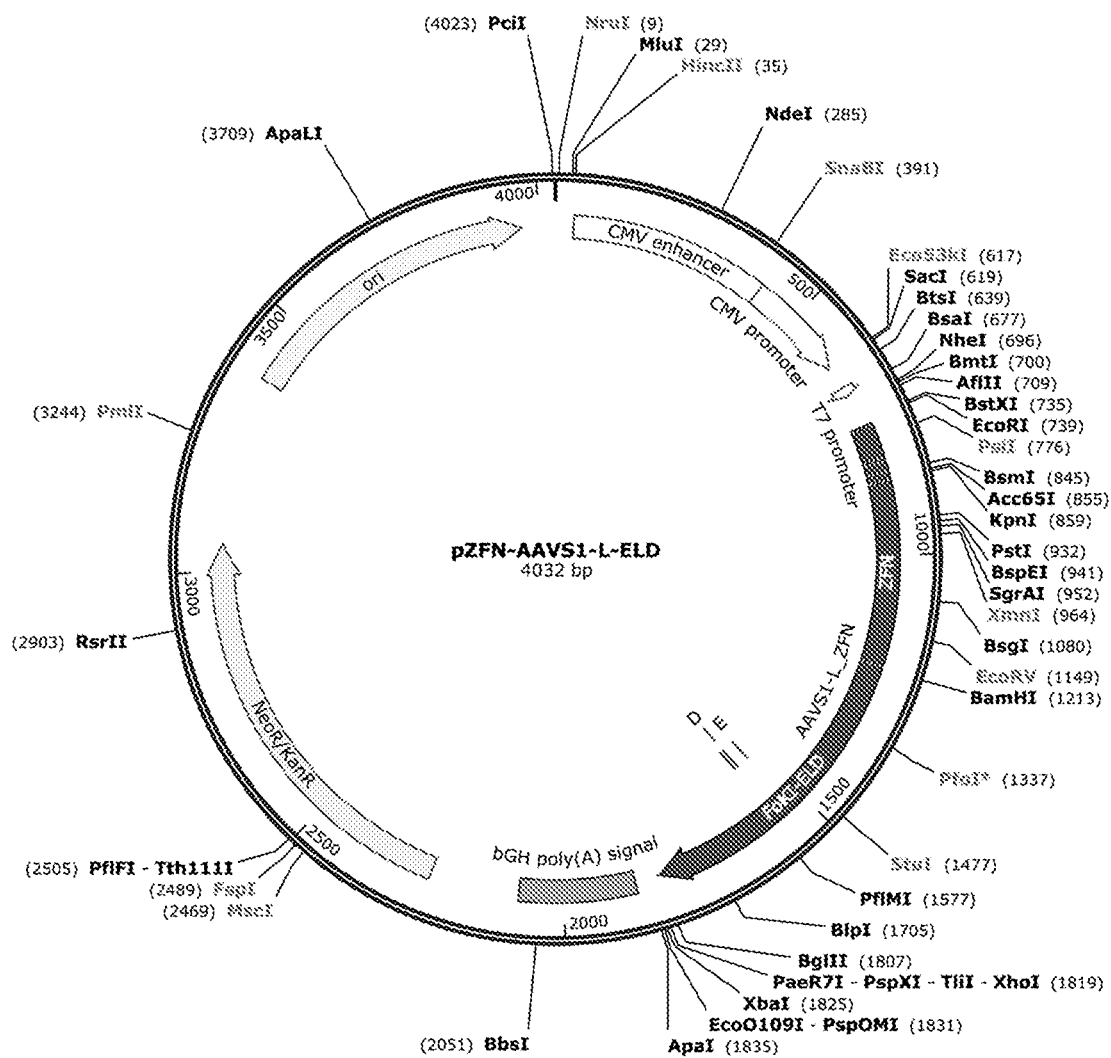
Figure 25:
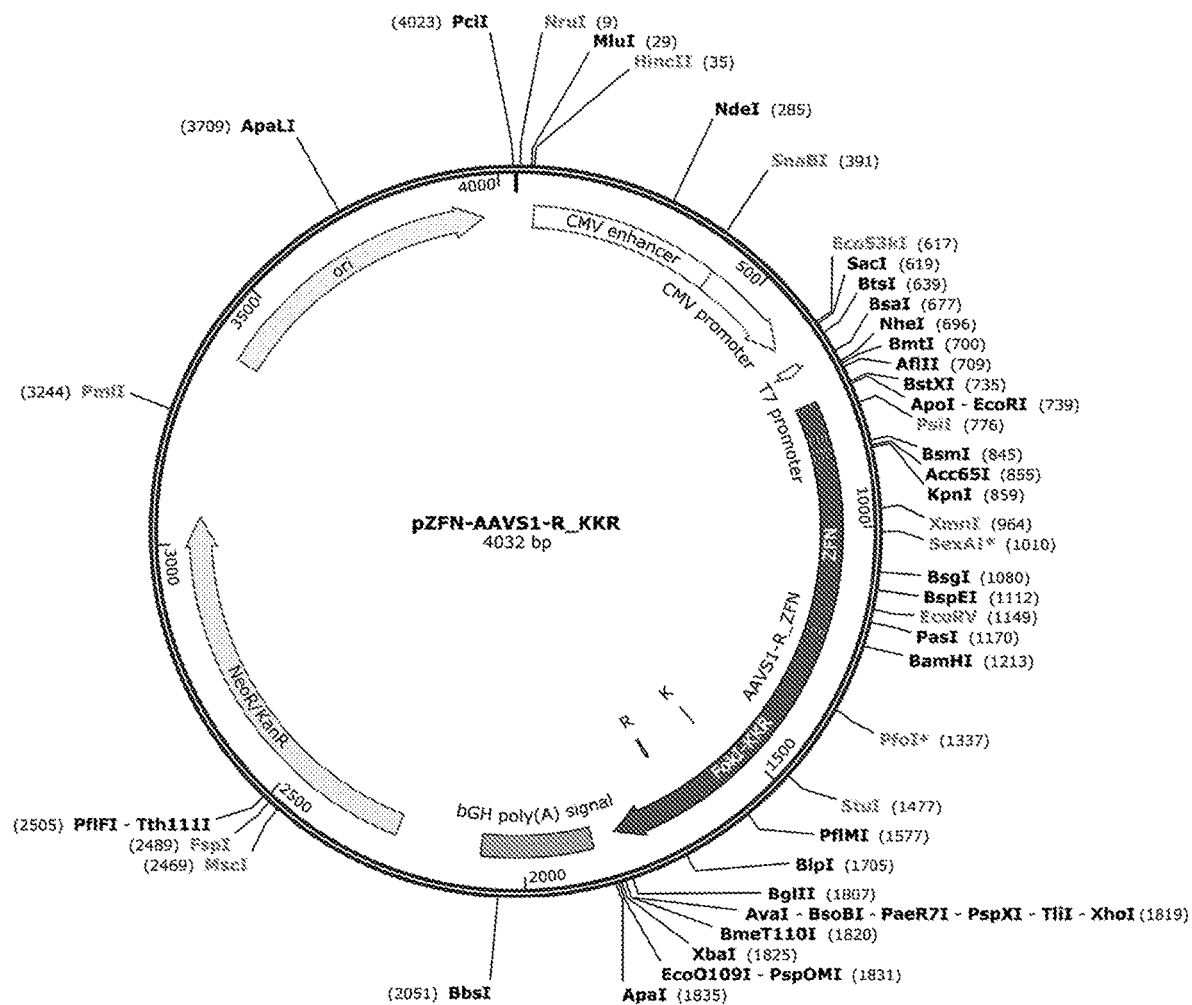
Figure 26:
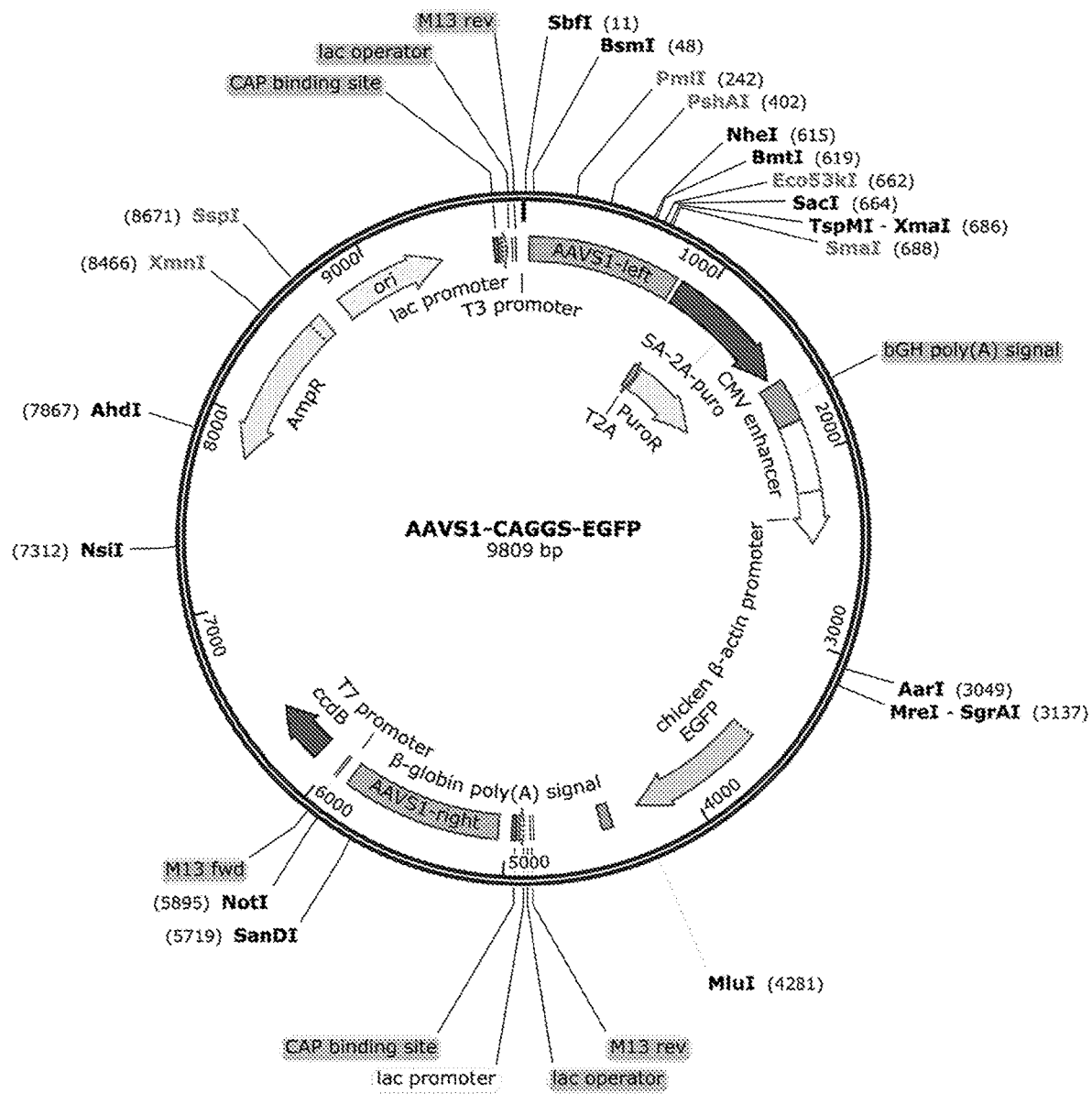
Figure 27:
Figure 28:
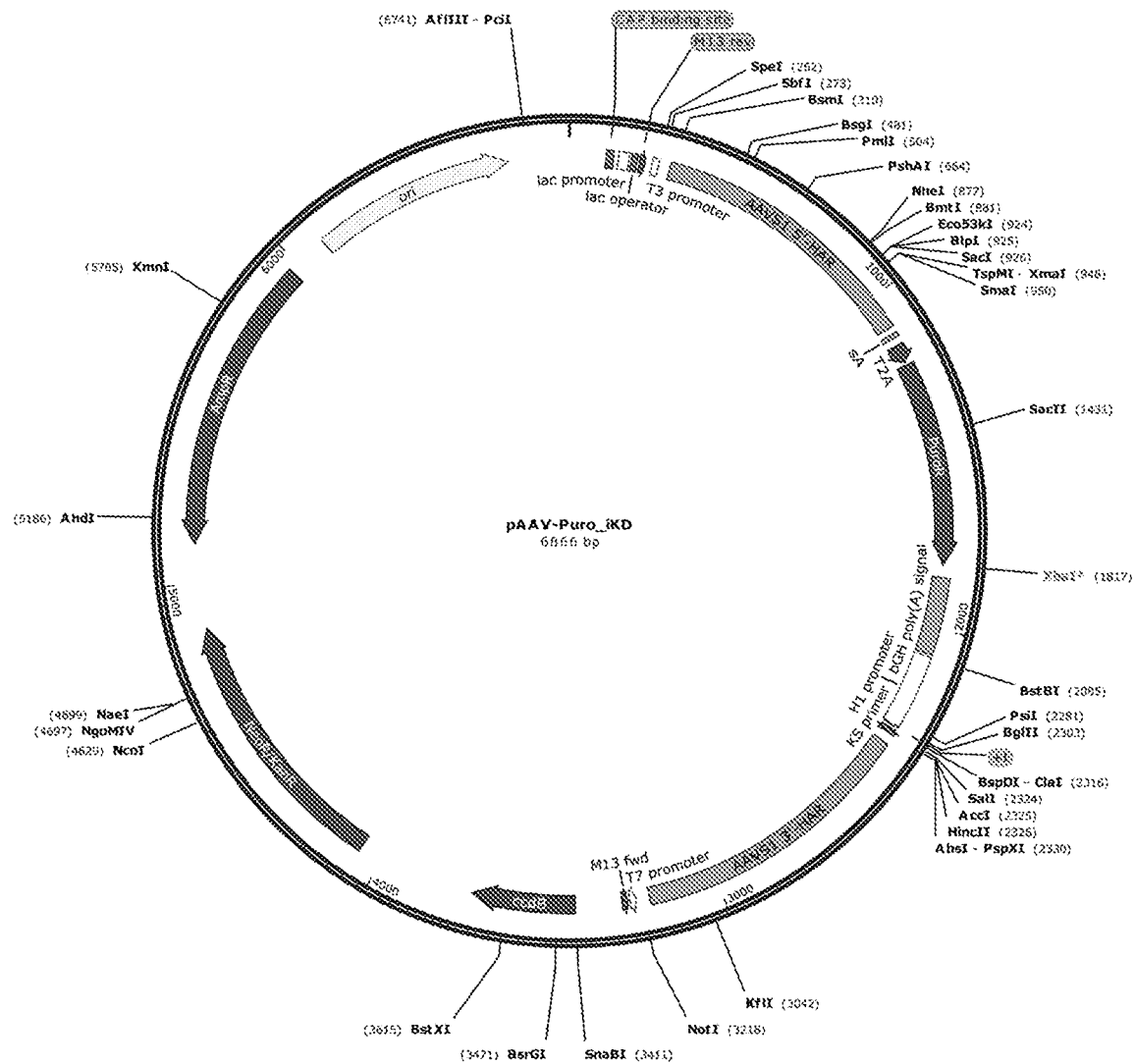
Figure 29:
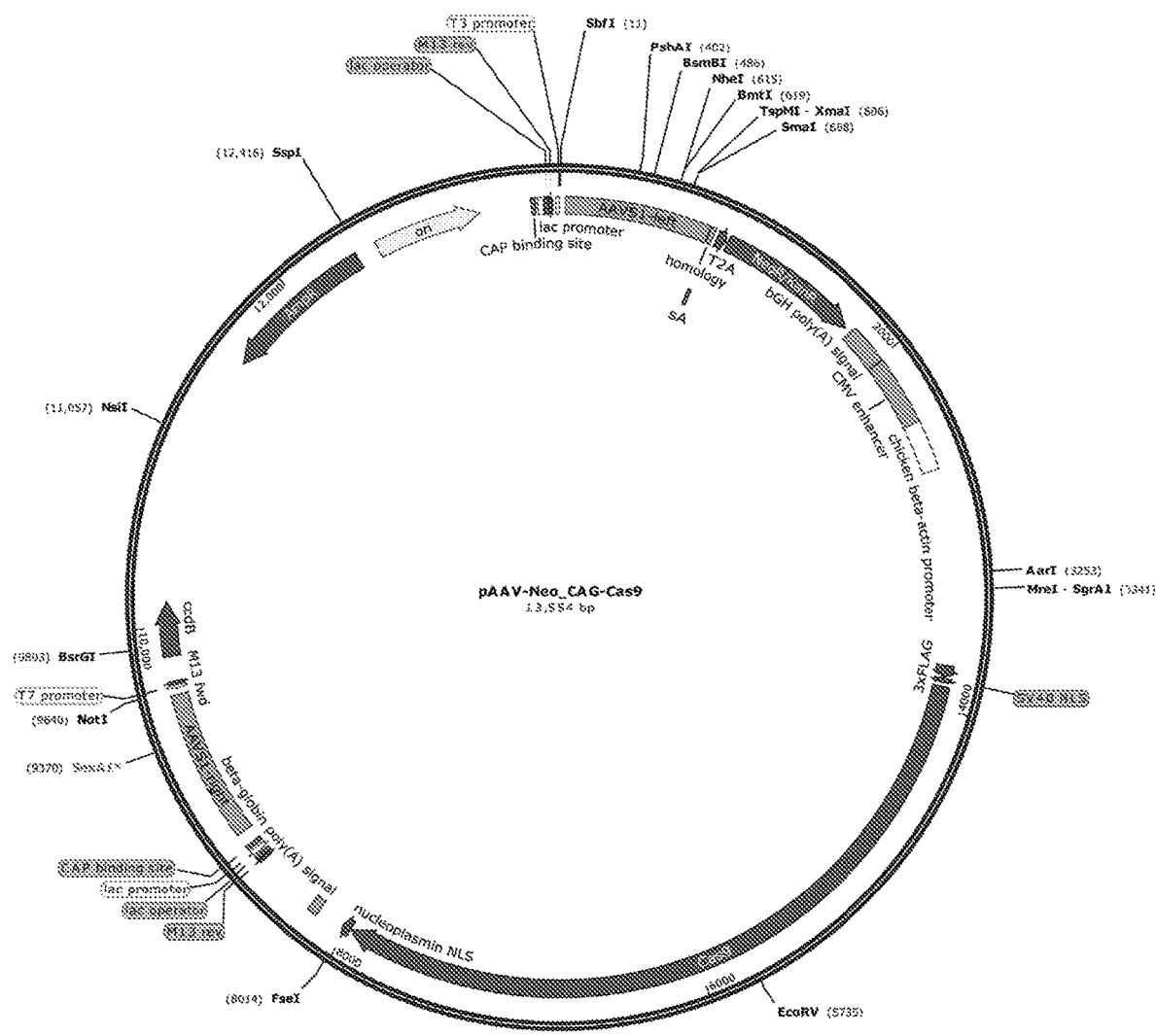
Figure 30:
Figure 31:

A donor plasmid was constructed that serves as a template DNA to facilitate homology directed repair of a Cas9n-induced DSB. Two hROSA26 homology arms were generated by high-fidelity PCR amplification. Genomic DNA that was isolated from H9 hESCs served as a template. The 5' and 3' homology arms were 904 bp and 869 bp in length, respectively. Both were subsequently inserted into the multiple cloning site of the pUC19 vector. To target the hROSA26 locus, cells were transfected with the plasmid, the two gRNA/Cas9n construct and the EGFP donor plasmid (FIG. 22)

Figure 32:
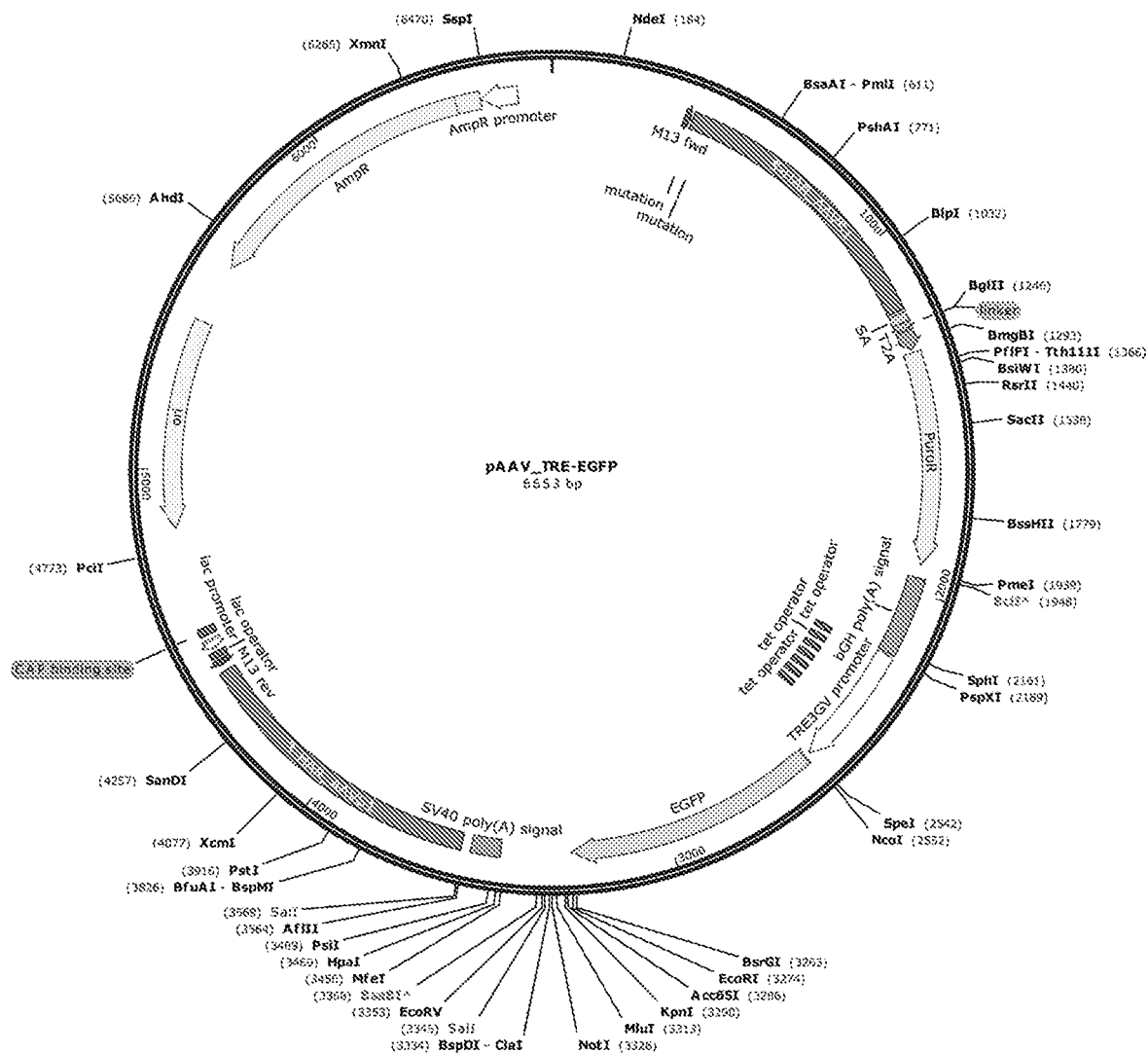
Figure 33:
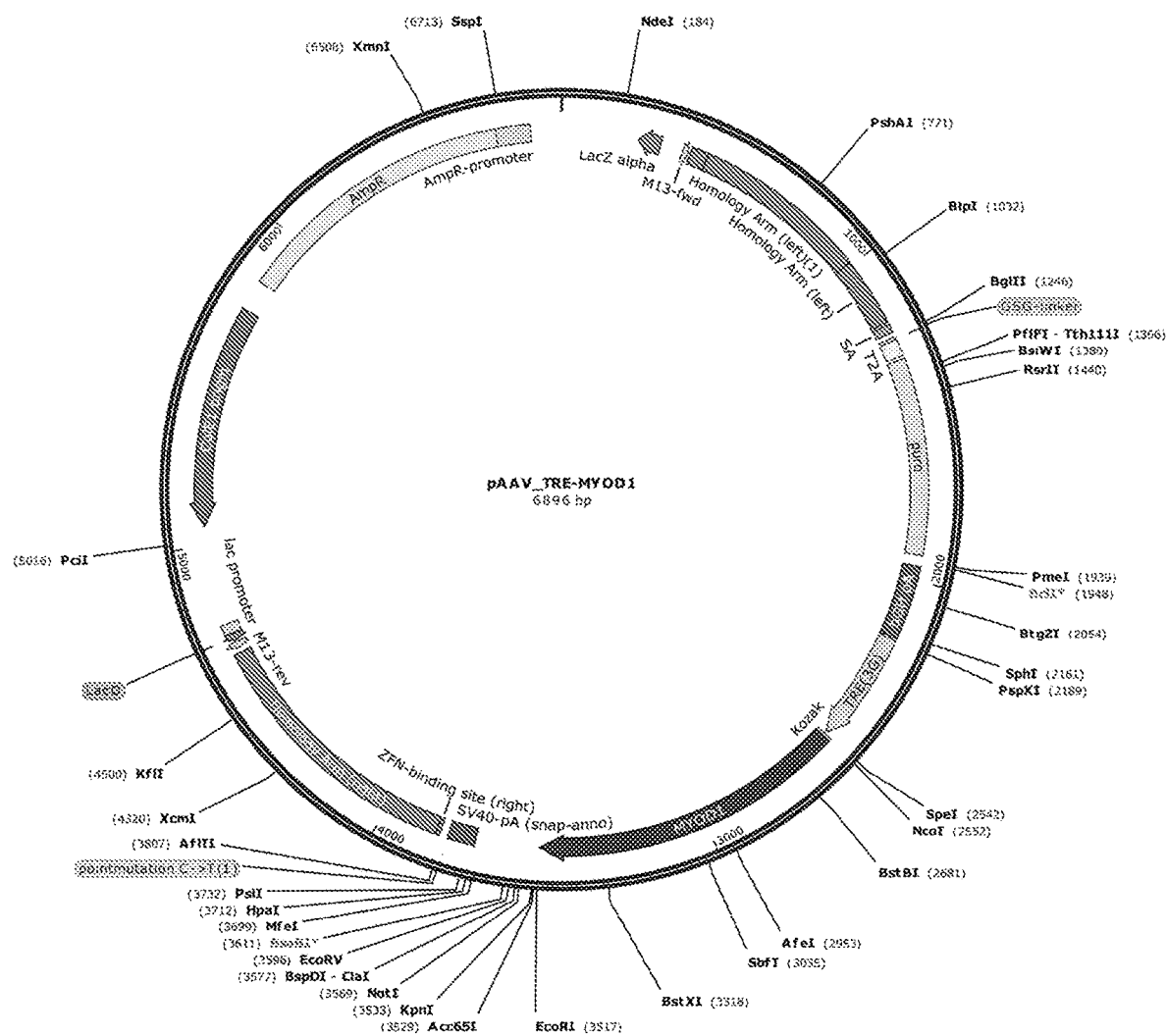

The pR26_CAG-rtTA targeting vector (FIG. 23) was constructed by cloning the coding sequence of a third generation rtTA (PCR-amplified from pLVX-Tet3G) into the BamHI/MluI sites of pR26_CAG-EGFP thus replacing the EGFP sequence. AAVS1 ZFN expression plasmids were a generous gift of Dr. Kosuke Yusa (Wellcome-Trust Sanger Institute). The inducible EGFP AAVS1 targeting vector was constructed by Gibson Assembly (New England Biolabs) in which three inserts were ligated into the EcoRI/HindIII sites of the multiple cloning site of the pUC19 vector (Thermo Fisher Scientific): The first insert comprised the upstream AAVS1 homology arm, a splice acceptor, a T2A-site and the puromycin resistance cassette (PCR-amplified from pTRE-EGFP; addgene 22074, deposited by Rudolf Jaenisch). The second insert contained the inducible TRE3G promoter (PCR-amplified from pLVX-TRE3G). The third insert comprised the EGFP expression cassette and the AAVS1 downstream homology arm (PCR-amplified from pTRE-EGFP; addgene 22074, deposited by Rudolf Jaenisch). The resulting plasmid was termed pAAV_TRE-EGFP (FIG. 32). The pAAV_TRE-NGN2 and pAAV_TRE-MYOD1 (FIG. 33) targeting vectors were constructed by cloning the NGN2 and MYOD1 coding sequence, respectively (NGN2: PCR-amplified from pLVX-TRE-NGN2, gift from Oliver Brustle; MYOD1: PCR-amplified from a commercially available cDNA plasmid, Open Biosystems MHS6278-202832821, Accession: BC064493, Clone ID: 5022419) into the SpeI/EcoRI sites of pAAV_TRE-EGFP, thus replacing the EGFP sequence.

Further plasmids were also created using similar methods, and all plasmids used are depicted in FIGS. 20 to 33. These plasmids were either created or generously donated. The plasmids used in the Examples include (in order of FIGS. 20-33): pSpCas9n(BB), _R26-R, pSpCas9n(BB) (the combination of these two plasmids is predicted to induce a specific double strand break in the intron between exons 1 and 2 of THUMPDS3-AS1 on chromosome 3 (ROSA26 locus)), _R26-L pR26_CAG_EGFP, pR26_CAG_rtTA, pZFN-AAVS1-L-ELD (zinc finger nuclease left), pZFN-AAVS1-R-KKR (zinc finger nuclease right), pAAV_CAG_EGFP (donor), pR26-Neo_CAG-OPTtetR (hROSA26 targeting of codon-optimized tetR), pAAV-Puro_iKD (AAVS1 targeting of inducible shRNA), pAAV- Neo_CAG-Cas9 (AAVS1 targeting of Cas9), pAAV-Puro_siKO (AAVS1 targeting of inducible gRNA,), pAAV-Puro_siKO-2TO (AAVS1 targeting of inducible gRNA, version with 2 tet operons in promoter), pAAV_TRE-EGFP (EGFP inducible overexpression, attached) and pAAV_TRE-MYOD1 (MYOD1 inducible overexpression for muscle).

Gene Targeting

Targeting of the hROSA26 locus and the AAVS1 for gene knockdown and knockout was performed by nucleofection. Human pluripotent stem cells (PSCs) were dissociated to single cells with TrypLE Select (Gibco), and $2\times10^6$ cells were nucleofected (100 µl reaction volume; total of 12 µg of DNA, which was equally divided between the two gRNA/Cas9n plasmids and the targeting vector) using the Lonza P3 Primary Cell 4D-Nucleofector X Kit and cycle CA-137 of the Lonza 4D-Nucleofector System. Nucleofected hPSCs were plated onto irradiated multi-drug resistant (DR4) mouse embryonic fibroblasts and cultured in KSR media [consisting of Advanced DMEM/F12 (80%), knock-out serum replacer (20%, Gibco), L-Glutamine (1 mM), 2-Mercaptoethanol (0.1 mM) and Penicillin/Streptomycin (1%)] supplemented with FGF2 (4 ng/ml, Department of Biochemistry, University of Cambridge). Y-27632 (5 µM, Tocris) was added for 24 h before and after nucleofection to promote cell survival. After 3-6 days, neomycin-resistant hPSCs were selected by adding G418 (50 µg/ml, Sigma-Aldrich) for 7-10 days. Subsequently, individual clones were picked, expanded in feeder-free conditions and finally analyzed by genotyping.

Targeting of the AAVS1 locus was also performed by lipofection. Human PSCs were seeded in feeder-free conditions in 6-well plates, and transfected 48 h after passaging. Transfection was performed in Opti-MEM (Gibco) supplemented with Lipofectamine2000 (10 µl/well, Thermo Fisher Scientific) and a total of 4 µg of DNA (equally divided between the two AAVS1 ZFN plasmids and the targeting vector) for 24 h. After 3-5 days, resistant hPSCs were selected by adding puromycin (1 µg/ml, Sigma-Aldrich) for 5-8 days. Subsequently, individual clones were picked, expanded and analyzed by genotyping. Antibiotic resistance can be used to select clonal lines.

Drug-resistant hPSC clones from targeting experiments were screened by genomic PCR to verify site-specific inducible cassette integration, to determine the number of targeted alleles, and to exclude off-target integrations. PCRs were performed with LongAmp Taq DNA Polymerase (New England Biolabs). Table 2 reports the primer combinations used for the various targeting vectors. The results of all targeting experiments are summarized in Table 1. Karyotype analysis was performed by standard G banding techniques (Medical Genetics Service, Cambridge University Hospitals). To prepare the targeted human PSCs for chromosome analysis, cells were incubated in fresh culture media supplemented with Y-27632 (5 µM, Tocris) and KaryoMAX Colcemid (100 ng/ml, Gibco) for 4 h at +37° C. Subsequently, cells were harvested as single cells, washed, and pelleted. Nuclei swelling and spreading of the chromosomes was achieved by treatment with hypotonic 0.055 M KCl-solution for 5-10 minutes. Finally, cells were fixed with methanol and glacial acetic acid (ratio 3:1).

For OPTiKD, AAVS1 targeting was performed by lipofection as previously described. Briefly, hPSCs were seeded feeder-free in 6-well plates, and transfected 48 h following cell passaging with 4 kg of DNA (equally divided between the two AAVS1 ZFN plasmids and the targeting vector) using 10 µl per well of Lipofectamine 2000 in Opti-MEM media (Gibco) for 24 h, all according to manufacturer's instructions. After 4 days, 1 kg ml-1 of Puromycin was added to the culture media, and individual clones were picked and expanded following 7-10 days of selection.

For single site OPTiKO, AAVS1 targeting was performed by nucleofection. hESCs pre-treated for 16 h with 10 µM Y-27632 (Tocris) were dissociated to clumps of 2-8 cells using Accutase (Gibco), and 2×106 cells were nucleofected in 100 µl with a total of 12 kg of DNA (4 kg each for the two ZFN plasmids, and 2 kg each for the two targeting vectors) using the Lonza P3 Primary Cell 4D-Nucleofector X Kit and the cycle CA-137 on a Lonza 4D-Nucleofector System, all according to manufacturer's instructions. Nucleofected hESCs were plated onto a feeder layer of irradiated DR4 (puromycin and neomycin resistant) mouse embryonic fibroblasts and cultured in KSR media supplemented with 4 ng ml-1 FGF2 and 10 µM Y-27632 (this last only for the first 24 h). After 4 days, hPSC colonies carrying both puromycin and neomycin resistance gene were selected for 7-10 days with 25 kg ml-1 of Geneticin (G418 Sulfate, Gibco) and 0.5 kg ml-1 Puromycin. Individual clones were then picked and expanded in feeder-free conditions.

AAVS1-EGFP, ROSA26-EGFP, ROSA26-STDtetR, ROSA26-OPTtetR, and ROSA26-EGFPd2 hESCs were generated by lipofection (AAVS1 locus) or nucleofection (ROSA26 locus) of the targeting vectors with AAVS1 ZFN or ROSA26 CRISPR/Cas9n pairs (as described above). 2 kg ml-1 Blasticidin S-HCl (Gibco) was used for pR26-Bsd_CAG-EGFPd2 plasmid. Generation of inducible EGFP overexpression hESCs carrying ROSA26-rtTA and AAVS1-TRE-EGFP transgenes is described elsewhere. Briefly, cells were sequentially gene targeted first by nucleofection of pR26-Neo_CAG-rtTA with ROSA26 CRISPR/Cas9n plasmids, then by lipofection of pAAVPuro_TRE-EGFP with AAVS1 ZFN plasmids.

Figure 16:
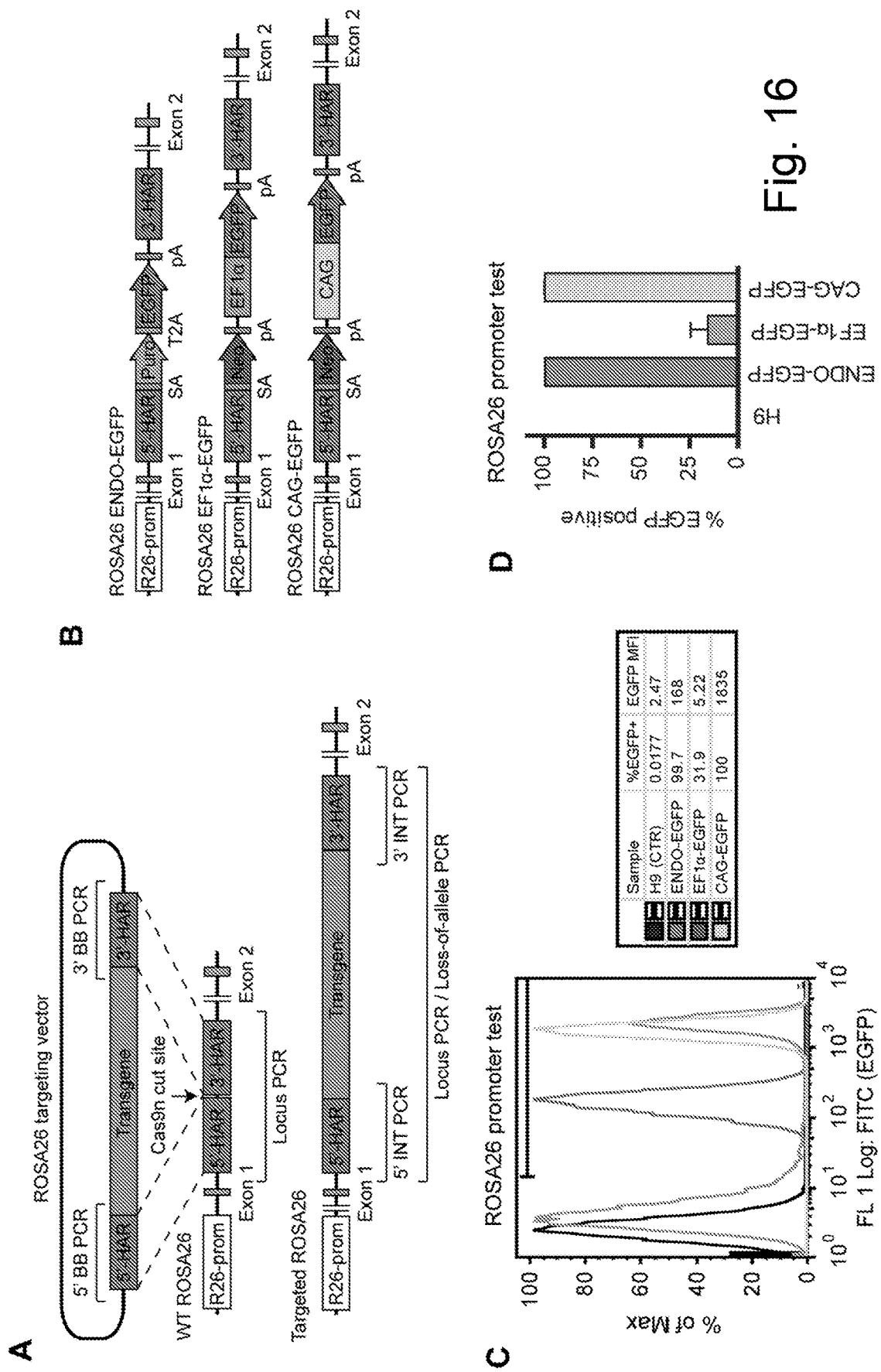
FIG. 16 (a-d) Generation of ROSA26 and AAVS1 EGFP reporter hESCs.

Gene targeted hPSC clonal lines were screened by genomic PCR to verify site-specific targeting, determine the number of alleles targeted, and exclude off-target integrations of the targeting plasmid (see FIG. 16A).

Inducible Cassette Overexpression

Overexpression of inducible cassettes (EGFP, NGN2, MYOD1 and OLIG2-SOX10, respectively) was induced by adding doxycycline hyclate (Sigma-Aldrich) to the culture media. Unless stated otherwise doxycycline was used at a final concentration of 1 µg/ml. Media containing doxycycline was kept light protected, and changed every 24 hours. Cells expressing EGFP are herein termed OPTi-EGFP, those expressing NGN2 are termed OPTi-NGN2, cells expressing MYOD1 are called OPTi-MYOD1 and cells expressing OLIG2-SOX10 are called OPTi-OLIG2-SOX10.

Inducible Gene Knockout and Knockdown

Unless otherwise described in the figure legends or Examples, tetracycline hydrochloride (sigma-Aldrich) was used at 1 µg ml$^{-1}$ to induce gene knockdown or knockout. Induction of neurons Pluripotent OPTi-NGN2 cells were dissociated into single cells with TrypLE and plated onto Matrigel (35 µg/cm$^2$, Scientific Laboratory Supplies) coated dishes at a density of 75.000 cells per well of a 12 well plate. Forward programming was initiated 24-48 hours after the split. Unless stated otherwise, the induction was performed in DMEM/F12 (Gibco) supplemented with Glutamax (100×, Gibco), Non-Essential Amino Acids (100×, Gibco), 2-Mercaptoethanol (50 µM), Penicillin/Streptomycin (1%), and doxycycline (1 µg/ml). After 2 days of induction, the medium was switched to Neurobasal-medium supplemented with Glutamax (100×), B27 (50×, Gibco), BDNF (10 ng/ml, Peprotech), NT3 (10 ng/ml, R&D Systems), Penicillin/Streptomycin (1%), and doxycycline (1 µg/ml).

Induction of Skeletal Myocytes

Pluripotent OPTi-MYOD1 cells were dissociated into single cells with TrypLE and plated onto gelatine/MEF-medium coated dishes at a density of 100.000 cells per well of a 12 well plate. Forward programming was initiated 24-48 hours after the split. Unless stated otherwise, the induction was performed in DMEM (Sigma-Aldrich) supplemented with L-Glutamine (2 mM), 2-Mercaptoethanol (50 µM), Penicillin/Streptomycin (1%), insulin (7 µg/ml), all-trans retinoic acid (1 µM, Sigma-Aldrich), and doxycycline (1 µg/ml). After 5 days of induction, the medium was supplemented with CHIR99021 (3 µM, Tocris) and heat-inactivated horse serum (2%, Gibco) to enhance maturation.

Induction of Oligodendrocytes

Pluripotent OLIG2-2A-SOX10 OPTi-OX hPSCs were grown in colonies on gelatine/MEF coated culture dishes. Before the start of induction they were treated with SB and LDN overnight. The following day induction was initiated in CDM supplemented with doxycycline (1 µg/ml) and RA (0.1 µM). One day after induction, cells were split in CDM supplemented with RA (0.1 µM), PM (1 µM), and Y-27632 (5 µM), PDGFaa (20 ng/ml, Peprotech), FGF2 (5 ng/ml) onto PDL/laminin coated culture dishes (100.000 cells per well of a 12 well-plate). The following day cells were switched to oligodendrocyte media consisting of DMEM/F12, supplemented with Glutamax (100×), Non-Essential Amino acids (100×), 2-Mercaptoethanol (1000×), Penicillin-Streptomycin (100×), N2 Supplement (100×), B27 Supplement (50×), Insulin 7 µg/ml (Marko Hyvonnen), T3 60 ng/ml (Sigma), Biotin 100 ng/ml (Sigma), db-cAMP 1 µM (Sigma). Oligodendrocyte medium was supplemented with dox (1 µg/ml), PDGFaa (20 ng/ml), FGF2 (5 ng/ml), RA (0.1 µM) and PM (1 µM). Seven days post induction RA and PM was withdrawn. To keep induced cells in a proliferative state, cells were passaged every 4 days (75.000 cells per well of a 24 well plate) in the continued presence of the mitogens PDGFaa and FGF2. For differentiation of proliferative oligodendrocyte precursors, PDGFaa and FGF2 were withdrawn. Human recombinant NT3 (5 ng/µl, R&D Systems) was added to enhance cell survival.

Quantitative Real-Time PCR (qPCR)

RNA was extracted using the GenElute Mammalian Total RNA Miniprep Kit and the On-Column DNAse I Digestion Set (Sigma-Aldrich). cDNA synthesis was performed with the Maxima First Strand cDNA Synthesis Kit (Thermo Fisher Scientific). Applied Biosystems SYBR Green PCR Master Mix was used for qPCR. Samples were run on the Applied Biosystems 7500 fast PCR machine. All samples were analyzed in technical duplicates and normalized to the house-keeping gene Porphobilinogen Deaminase 1 (PBGD). Results were analyzed with the ΔΔCt method. See Table 3 for primer sequences.

Flow Cytometry

For analysis of EGFP expression cells were harvested with TrypLE Select (Gibco) for 5-10 minutes at 37° C. to obtain a single cell suspension. Following a wash with PBS, cells were resuspended in ice-cold PBS supplemented with DAPI (10 µg/ml), and incubated for 5 minutes on ice. Cells were analyzed using a Cyan ADP flow-cytometer to determine the levels of EGFP expression of viable cells (DAPI negative). For staining and analysis of myosin heavy chain expression cells were harvested with TrypLE Select (as for EGFP expression analysis), washed once with PBS, and fixed and permeabilized with Cytofix/Cytoperm solution (BD Biosciences). Subsequently, cells were washed and blocked in Perm/Wash buffer (BD Biosciences) supplemented with 3% bovine serum albumin (BSA) at +4° C. overnight. Staining with a PE-conjugated anti-MYH antibody (table 4) was carried out in Perm/Wash buffer for 1 h at +4° C. in the dark. After three washes with Perm/Wash buffer cells were analyzed with a Cyan ADP flowcytometer to determine the levels of MHC expression. Data analysis was performed with FlowJo (v10) and Graphpad Prism (v6).

Western Blot

Whole-cell protein was extracted with CelLytic M (Sigma-Aldrich) supplemented with complete Protease Inhibitor (Roche), and subsequently quantified by using Protein Quantification Kit-Rapid (Sigma-Aldrich). Protein electrophoresis was performed with NuPAGE LDS Sample Buffer and 4-12% NuPAGE Bis-Tris Precast Gels (Invitrogen). Following protein transfer on PVDF, membranes were blocked with PBS supplemented with 0.05% Tween-20 (PBST) 4% milk for 1 h at room temperature, and incubated with primary antibodies overnight in PBST 4% milk. Membranes were washed with PBST, incubated with HRP-conjugated secondary antibodies (Sigma-Aldrich) in PBST 4% milk, incubated with Pierce ECL2 Western Blotting Substrate (Thermo Fisher Scientific), and exposed to X-Ray Super RX Films (Fujifilm).

Immunocytochemistry

Cells were fixed in 4% paraformaldehyde (diluted in PBS) for 20 minutes at room temperature and subsequently washed three times with PBS. The cells were then blocked with 10% donkey serum (Sigma-Aldrich) and permeabilized with 0.3% Triton X-100 (diluted in PBS) for 20 minutes at room temperature. Subsequently, cells were incubated with appropriately diluted primary antibodies (supplemental experimental procedures) in 2% donkey serum and 0.1% Triton X-100 (diluted in PBS) at 4° C. overnight. Triton-X was omitted throughout all steps when staining the surface antigen PDGFRA, A2B5, and O4. After three washes with PBS, the cells were incubated for 1 hour at room temperature with corresponding donkey fluorophore-conjugated secondary antibodies (Alexa Fluor 488, 555, 568, and/or 647) in PBS supplemented with 1% donkey serum. Nuclei were visualized with 4',6-diamidino-2-phenylindole (DAPI, Thermo Fisher Scientific). EGFP expression and immunostainings were imaged using a Zeiss LSM 700 confocal microscope (Leica). The percentage of 13111-tubulin positive cells was calculated by determining βIII-tubulin expression in at least 50 randomly selected DAPI-positive cells in 3 visual fields of 3 biological replicates using an inverted Olympus IX71 fluorescence microscope.

Statistical analysis was performed with GraphPad Prism (v6). The number of replicates, the statistical test used, and the test results are described in the figure legends. Unless stated otherwise data is presented as mean±SEM.

Example 1: Dual Targeting of EGFP

Figure 4:
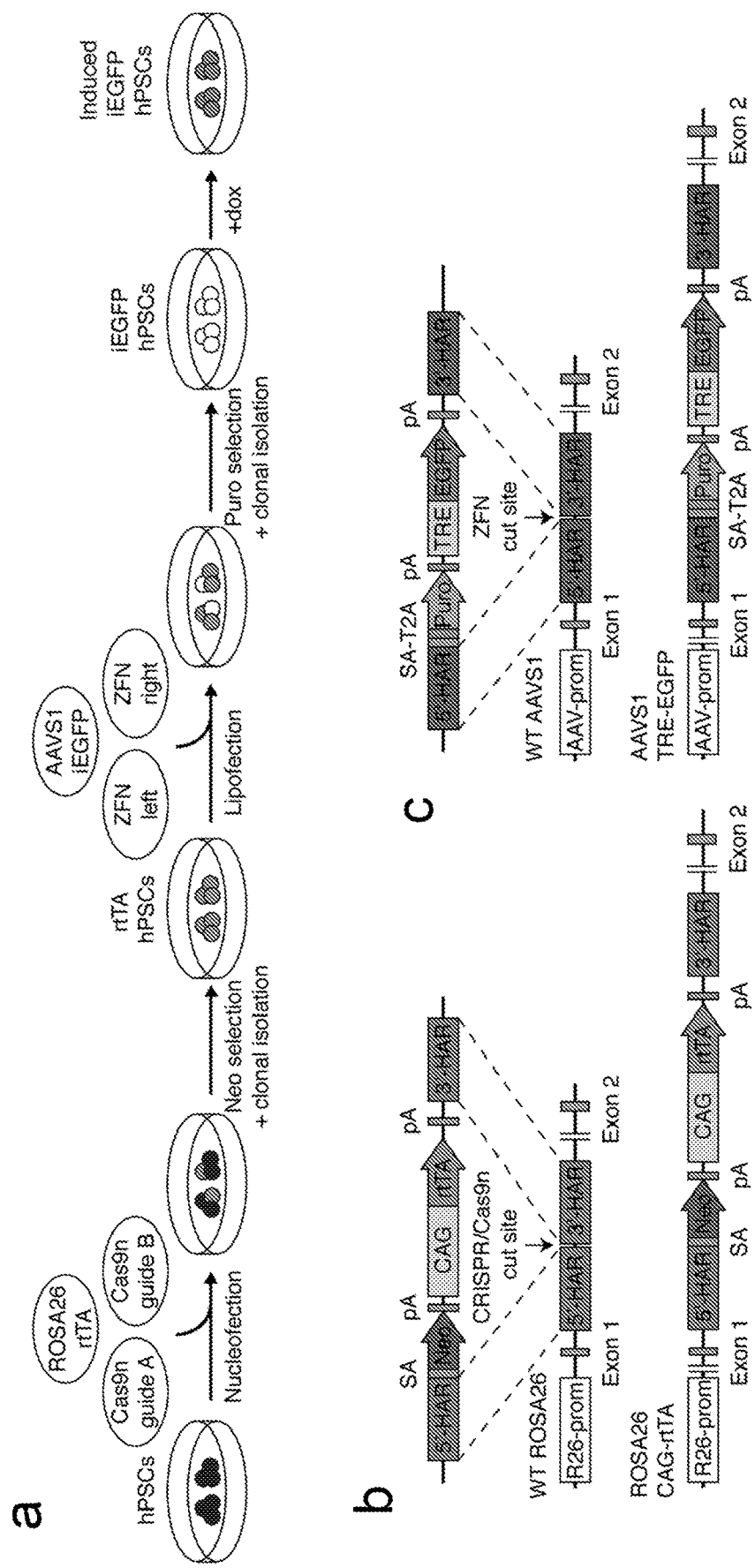
FIG. 4 (a-f): Targeting strategy for the dual GSH targeted Tet-ON overexpression system.
Figure 4:
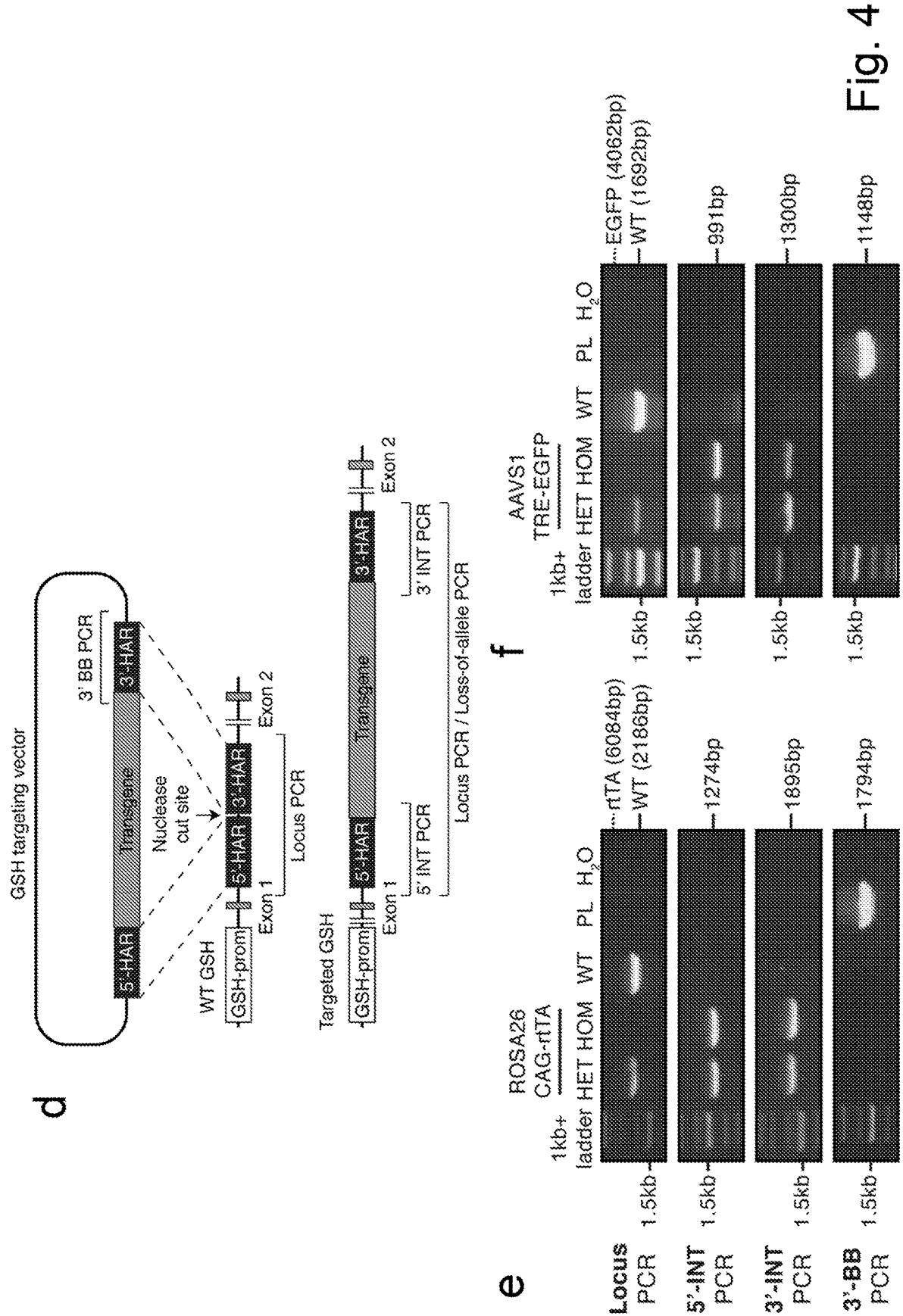

To develop an inducible overexpression platform in hPSCs, we sequentially targeted the two components of the Tet-ON system into two different GSHs. A constitutively expressed third generation rtTA was targeted into the human ROSA26 (hROSA26) locus by using a CRISPR/Cas9n-based targeting strategy and an inducible EGFP inducible cassette was inserted into the AAVS1 (FIG. 1a; FIGS. 4a-c). Both hROSA26 and AAVS1 targeting was highly efficient (FIGS. 4d-f, Table 1) and did not affect hPSC genomic stability, self-renewal, and differentiation (data not shown), therefore arguing against rtTA-dependent cellular toxicity.

Figure 1:
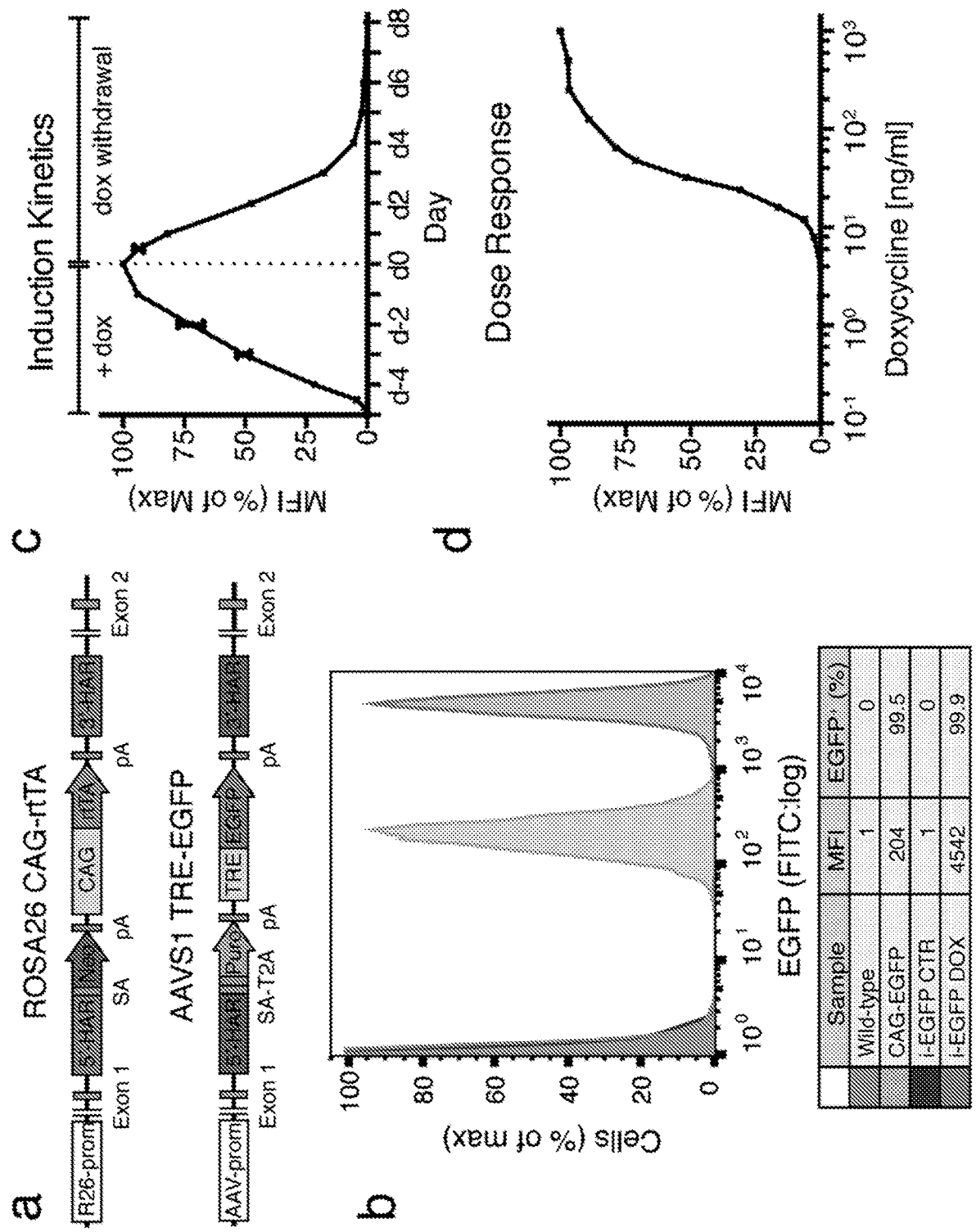
FIG. 1 (a-d): Validation of an optimized dual genomic safe harbor targeted overexpression system.

We then selected dual GSH-targeted clones that carried either one or two copies of each of the two inducible cassette (FIG. 5a). Homozygous targeting of the rtTA resulted in approximately two-fold higher levels of rtTA protein (FIG. 5b), and also in significantly increased EGFP levels following induction, when compared to heterozygous rtTA expression (FIGS. 5c-5e). Additionally, clones with homozygous targeting of the inducible EGFP cassette showed higher and more homogeneous EGFP levels compared to lines with heterozygous targeting (FIGS. 5c-5e). Importantly, all correctly targeted lines showed robust inducible EGFP expression, which was at least twenty-fold higher compared to the strong constitutive CAG promoter (FIG. 1b, FIGS. 5c-e). Collectively, these results support our initial hypothesis that targeting two copies of both elements of the Tet-ON system would result in maximal expression following induction. The peak of EGFP levels was reached approximately four days after induction, and expression was quickly reversed upon doxycycline withdrawal (FIG. 1c). Moreover, EGFP expression could be titrated by adjusting the dose of doxycycline (FIG. 1d).

Figure 6:
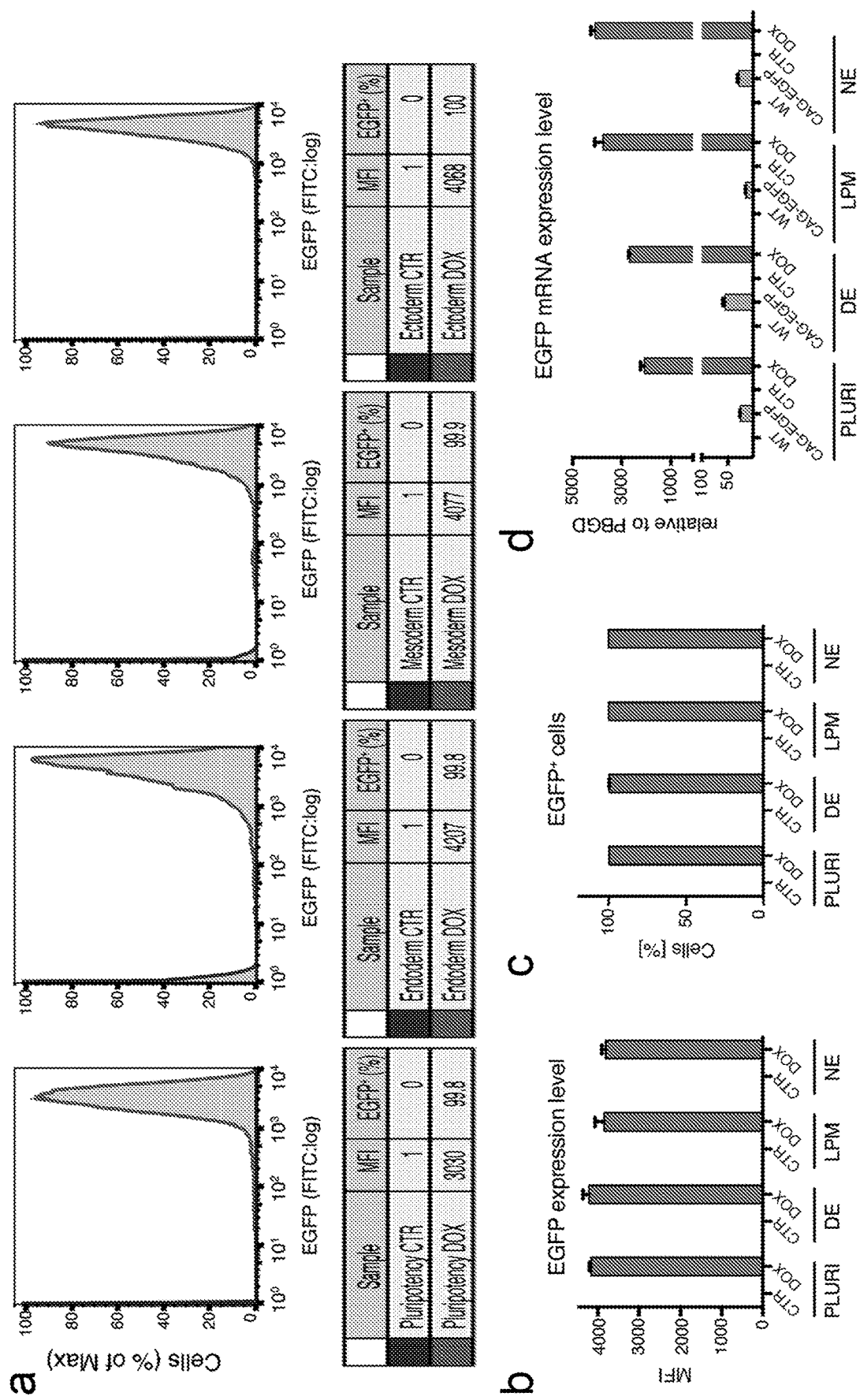
FIG. 6(a-d): Characterization of the OPTi-OX platform in hPSCs and during germ layer differentiation.

Importantly, inducible EGFP expression was not only highly efficient in hPSCs, but also during differentiation into the germ layers (colour photographic data not shown, data on FIGS. 6a-6d). Finally, and in agreement with the known tight transcriptional control of third generation Tet-ON systems, there was no detectable background expression of EGFP mRNA or protein in the absence of doxycycline as determined by flow cytometry and qPCR, respectively (FIG. 1b, FIG. 6d). Overall, these results established that dual GSH targeting of the Tet-ON system is a powerful strategy for optimal expression of inducible cassettes in hPSCs and their derivatives.

Example 2: Derivation of Excitatory Cortical Neurons from hESC and hiPSC

Figure 2:
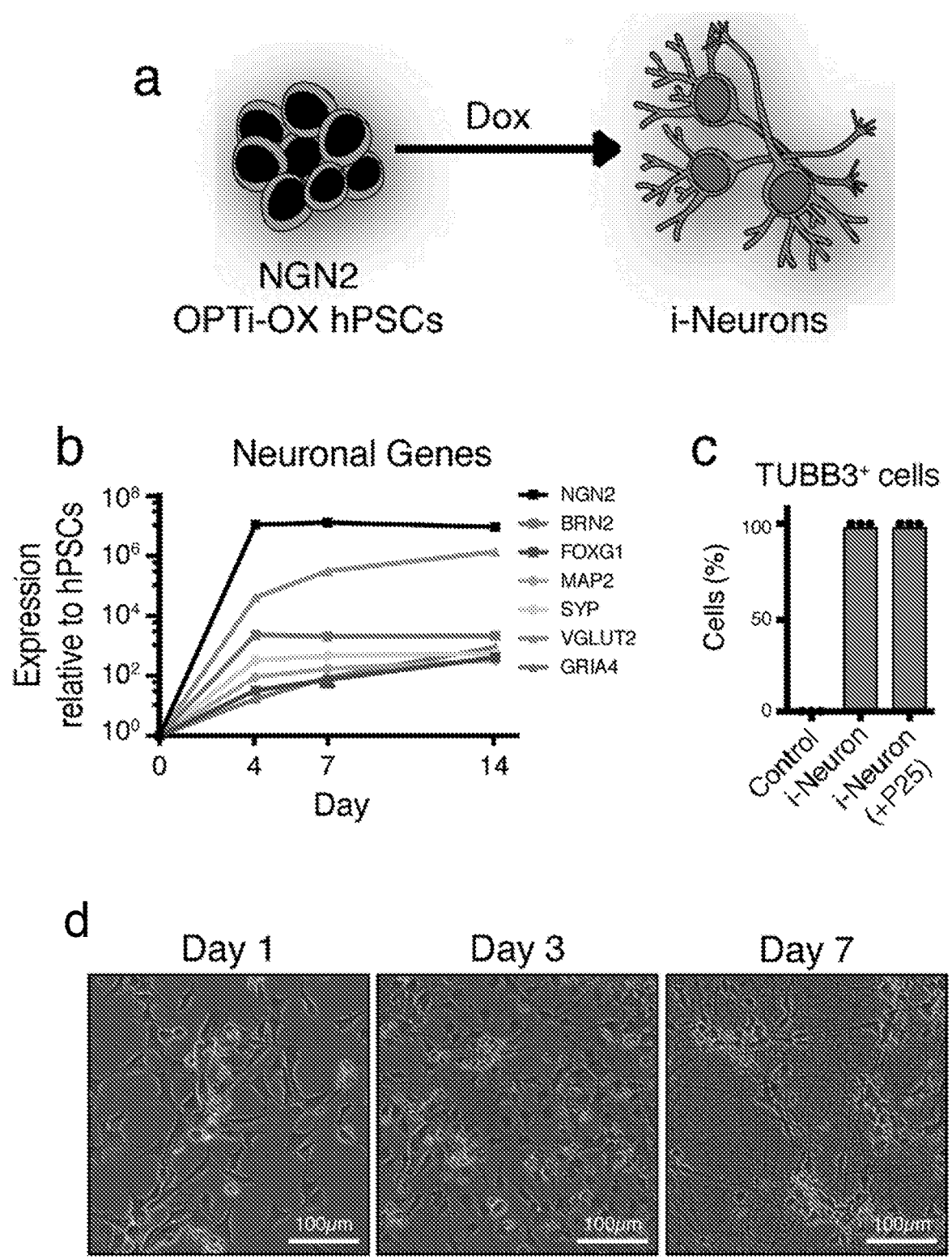
FIG. 2 (a-d): Overview of the experimental approach and results for rapid single step conversion of hPSCs into neuronal cells (i-Neurons) following doxycycline (dox) treatment.
Figure 3:
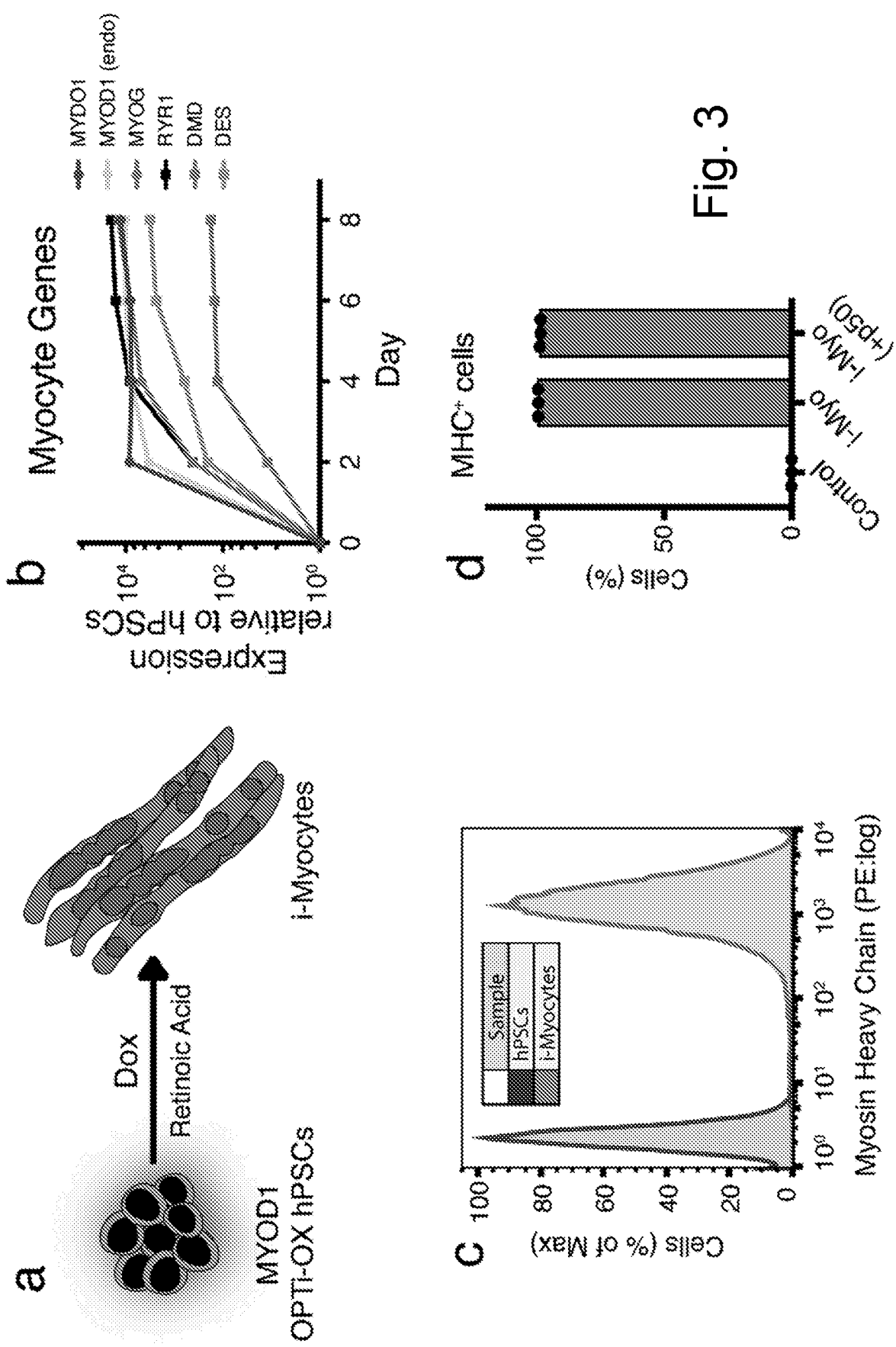
FIG. 3 (a-d): Forward programming of hPSCs into skeletal myocytes.
Figure 7:
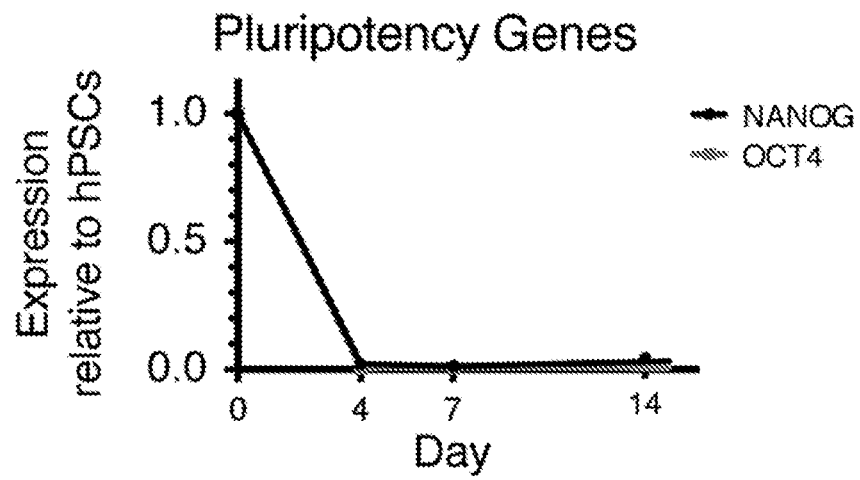
FIG. 7: Characterization of human i-Neurons. Quantitative RT-PCR results demonstrate rapid downregulation of the pluripotency factors NANOG and OCT4 upon treatment with doxycycline.

Previous studies have shown that these cells can be readily derived by lentiviral overexpression of any of the pro-neuronal bHLH-factors (ASCL1, NGN2, or NEUROD1) in hPSCs. Therefore, we generated OPTi-NGN2 hPSCs (FIG. 2a, Table 1). NGN2 induction resulted in rapid downregulation of pluripotency factors (FIG. 7) and initiation of a neuronal transcriptional program (FIG. 2b). Induced cells exhibited neuronal processes as early as three days post induction (data not shown). After one week, all cells displayed a neuronal morphology and expressed pan-neuronal marker proteins, such as βIII-tubulin and MAP2 (FIG. 2c). Quantitative RT-PCR revealed strong induction of typical forebrain markers such as BRN2 and FOXG1, and of glutamatergic neurons including GRIA4 and VGLUT2 (FIG. 2b), indicative of an excitatory cortical neuronal identity. Collectively, these results demonstrated a dramatic improvement in both speed and efficiency in generating neurons compared to traditional hPSC differentiation protocols, and a substantial increase in efficiency and purity relative to both transdifferentiation and lentiviral-based forward programming protocols. Similar results were obtained with OPTi-NGN2 hiPSCs, confirming the robustness of this method. Finally, we did not observe any drop in the efficiency of neuronal induction over extended culture periods of Opti-NGN2 hPSCs (>25 passages, FIG. 2c). Overall, our results demonstrated that OPTi-NGN2 hPSCs can be used as an inexhaustible source for unlimited, highly scalable, rapid, single step, virus-free, and near-deterministic generation of neurons.

Example 3: Generation of Skeletal Myocytes

Figure 8:
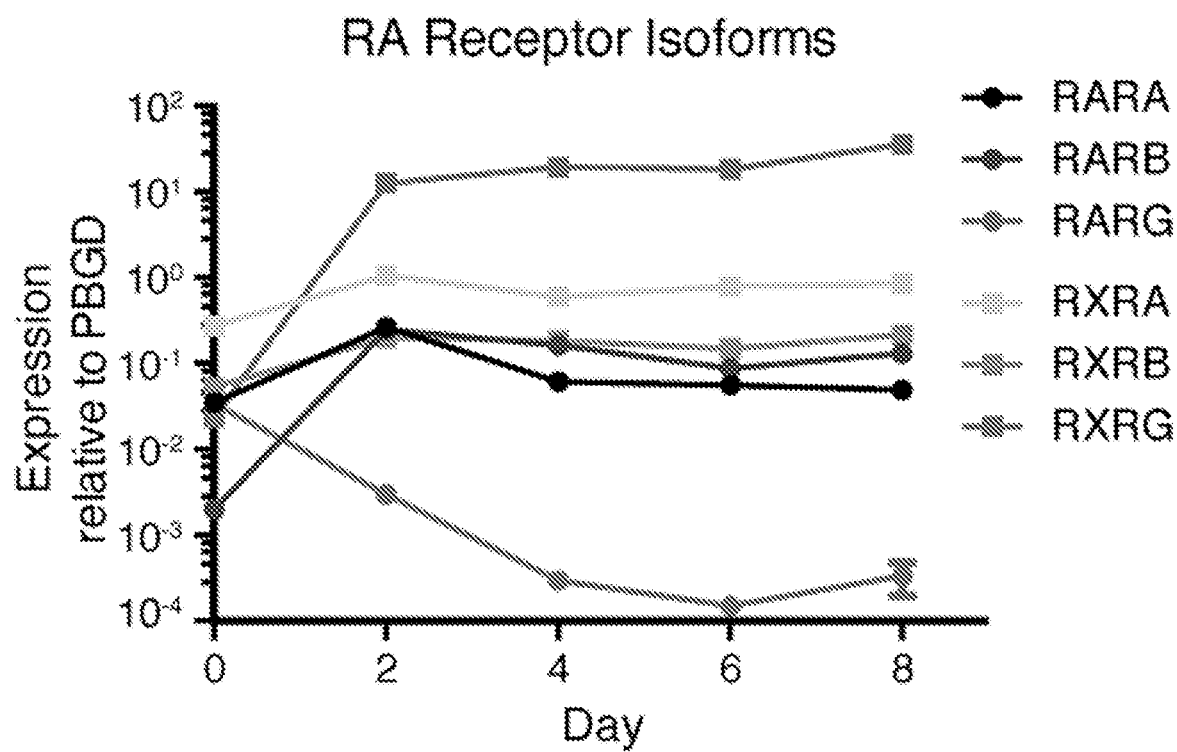
FIG. 8: RA signaling during myocyte induction. This figure shows qPCR analysis of the six retinoid and retinoid receptors during myocyte induction demonstrates expression of RARα, RARβ and all three RXR isoforms, but not of RARγ throughout the course of i-myocyte induction. A is α, B is β and G is γ.
Figure 9:
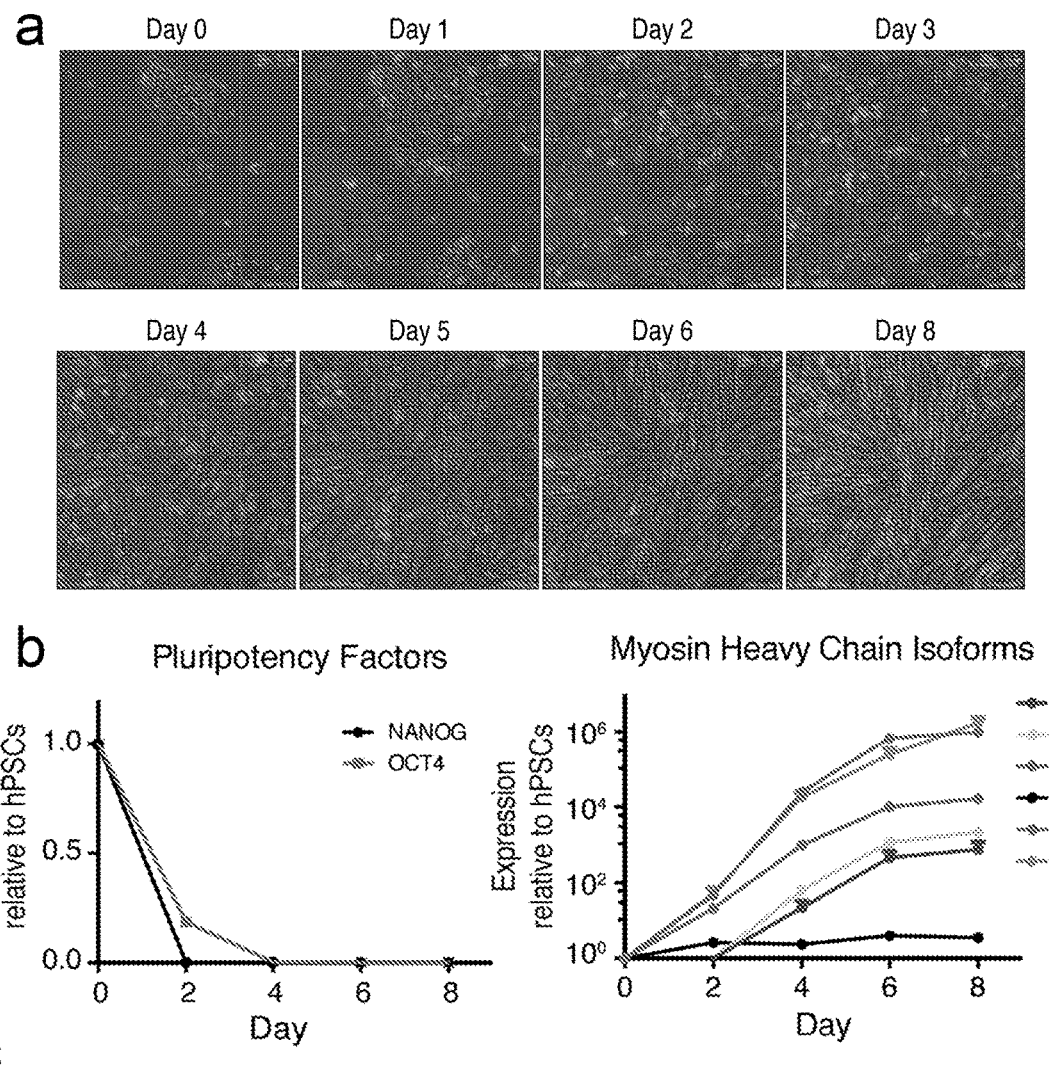
FIGS. 9(a) to 9(c): Characterization of the development of OPTi-MYOD1 hESCs into human i-Myocytes.
Figure 9:
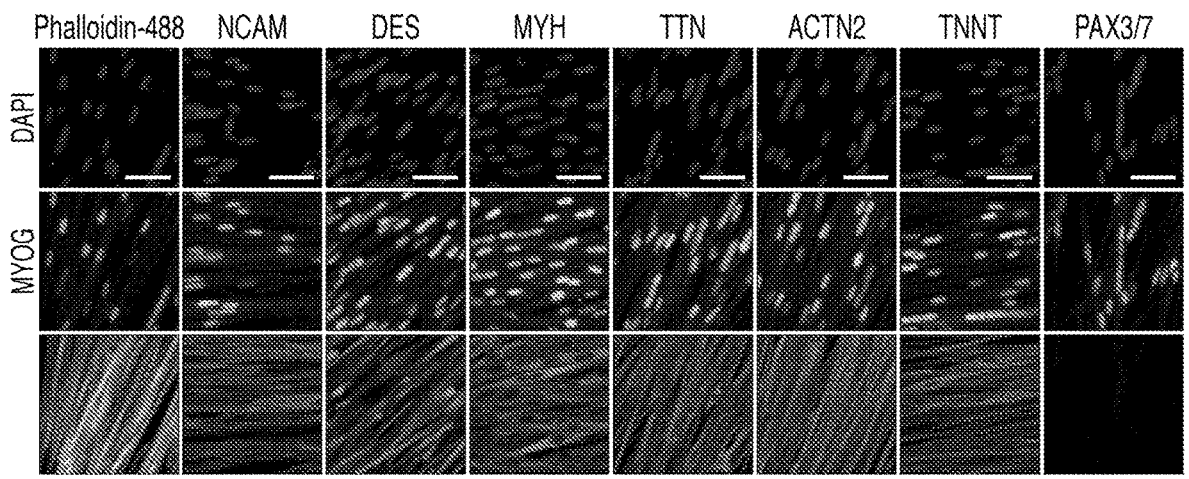
Figure 10:
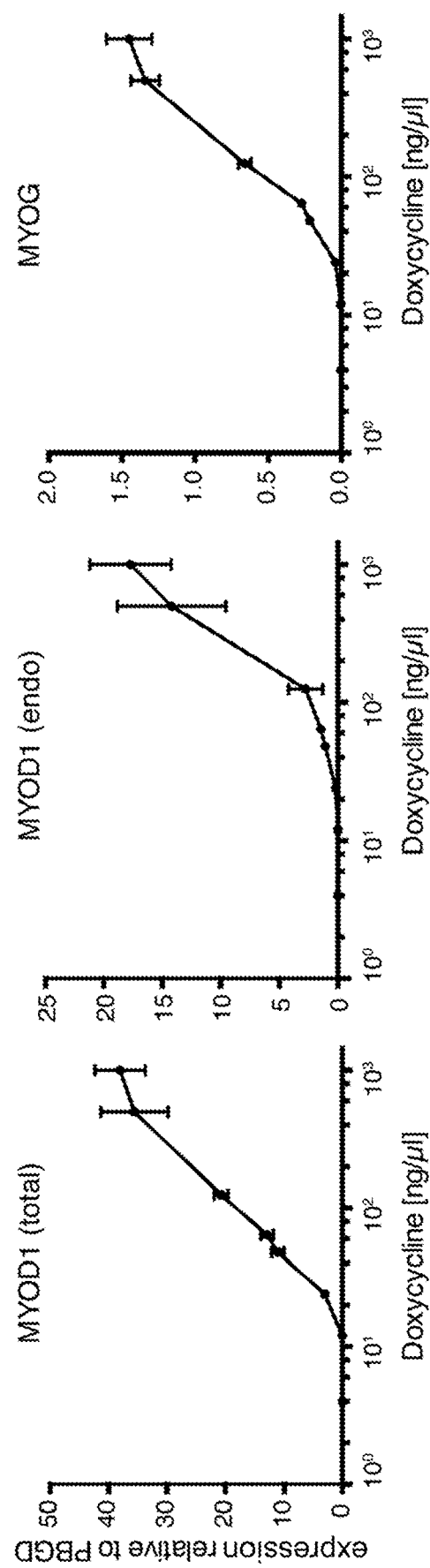
FIG. 10: These three graphs depict the qPCR results for total MYOD1, endogenous MYOD1, and MYOG 2 days post induction of OPTi-MYOD1 hPSCs with different concentrations of doxycycline. The qPCR results are shown 48 h post induction with different concentrations of doxycycline. Expression is plotted relative to the endogenous housekeeping gene PBGD.

The transcription factor MYOD1 is known to induce myogenic transdifferentiation when overexpressed in a variety of somatic cell types, however, the ability of hPSCs to undergo MYOD1-induced myogenic forward programming is currently debated. We generated OPTi-MYOD1 hPSCs (Table 1), but we noted that induction of MYOD1 expression following doxycycline treatment resulted in near complete cell death within 3-5 days in a broad range of culture conditions that were suggested previously to facilitate the conversion of hPSCs into skeletal myocytes. Since it is widely established that cellular reprogramming strategies can be enhanced by combining transcription factor overexpression with extracellular signaling cues, we performed a systematic screen for pro-myogenic factors by modulating major signaling cascades that are implicated in primitive streak formation, somitogenesis, and myogenesis. We found that the addition of all-trans retinoic acid (RA) in conjunction with MYOD1 overexpression resulted in rapid and near-complete conversion into myogenin and myosin heavy chain (MHC) double-positive myocytes by day 5 after induction. The effect of RA was concentration dependent and mediated through the RA-receptor isoforms RARα and RARβ, consistent with the expression pattern of RA receptors during developmental myogenesis (FIG. 8). This effect is thought to be independent of the mechanism of MYOD1 overexpression. Induced skeletal myocytes presented a typical spindle-like, elongated morphology, underwent extensive cell fusion and exhibited strong myogenic marker expression on both mRNA and protein levels (FIG. 3b, FIG. 9a-9c). Addition of nanomolar concentrations of acetylcholine (ACh) or the selective ACh-receptor agonist carbachol resulted in complete muscle fiber contraction, demonstrating functionality of the induced myocytes. Similar results were obtained with Opti-MYOD1 hiPSCs (data not shown). Importantly, myogenic induction efficiency did not decrease over extended culture periods (>50 passages, FIG. 3d), thus demonstrating the robustness and reproducibility of this method. Finally, we noted that the levels of the MYOD1-inducible cassette positively correlated with conversion efficiency, which highlights the importance of a robust gene-delivery and the superiority of this method over lentivirus-mediated reprogramming approaches (FIG. 10). Overall, the OPTi-MYOD1 forward programming strategy is approximately seven times faster and five times more efficient than most recent differentiation protocols of hPSCs into skeletal myocytes. Compared to previous forward programming protocols (Tanaka, A. et al. *PLoS One* 8, e61540 (2013) and Abujarour, R. et al. *Stem Cells Transl. Med.* 3, 149-60 (2014)) it is more efficient (>95% vs. 30-80%), free of randomly inserted inducible cassettes, chemically defined, fully reproducible, and more scalable.

These findings demonstrate that this method of controlling inducible cassette expression in hPSCs can be used as inexhaustible source for high-throughput and large-scale manufacturing of homogeneous cell populations. The speed of induction and the purity of the desired target cells are currently unrivalled by other methods.

Example 4: Generation of Oligodendrocyte Precursors and Oligodendrocytes

Figure 12:
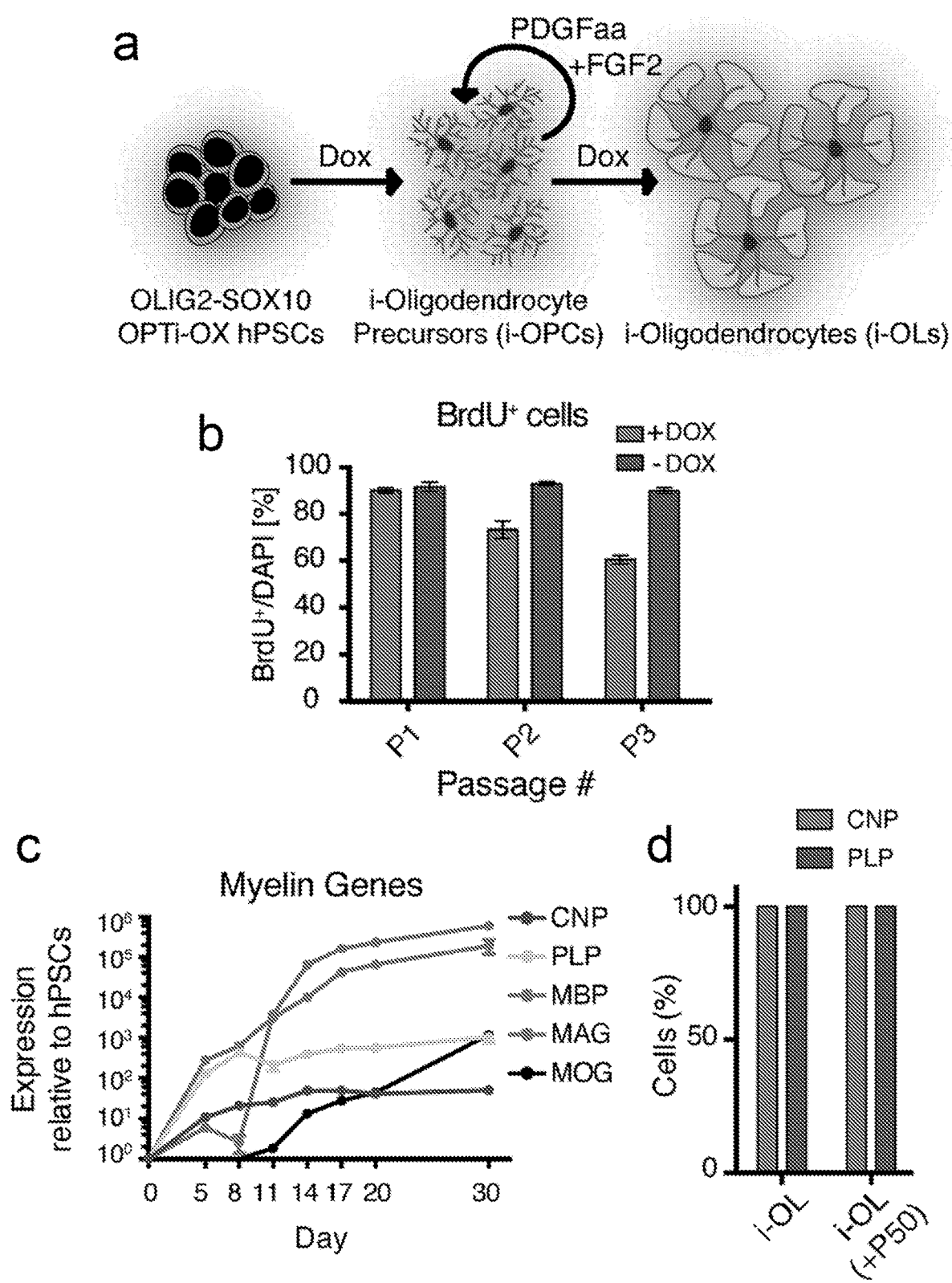
FIG. 12 (a-d) Forward programming of hPSCs into oligodendrocytes.
Figure 13:
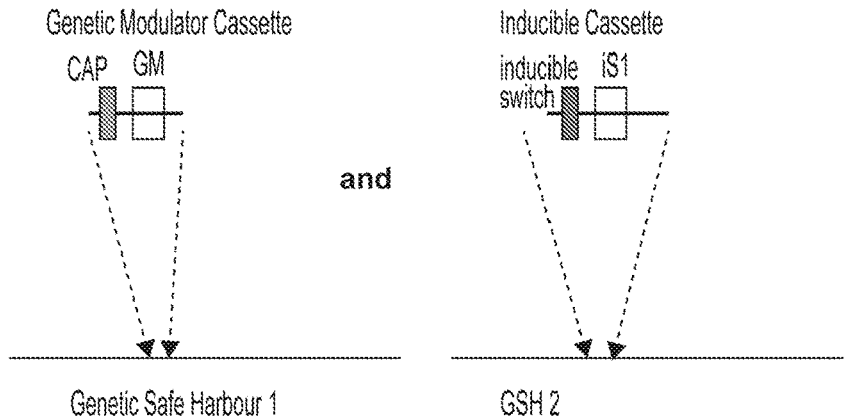
FIG. 13 is a schematic representation of the principles of the present invention. Essentially, this depicts the insertion into two different genetic safe harbor sites at the core of the present invention. One insertion controls the expression of the genetic sequence within the inducible cassette in a second insertion. Additional genetic material can be included in polycistronic vector constructs as shown. Further, more than two genetic safe harbor sites may be targeted, such that multiple inducible cassettes or other genetic material may be placed under the control of the modulator placed in the first GSH site.
Figure 13:
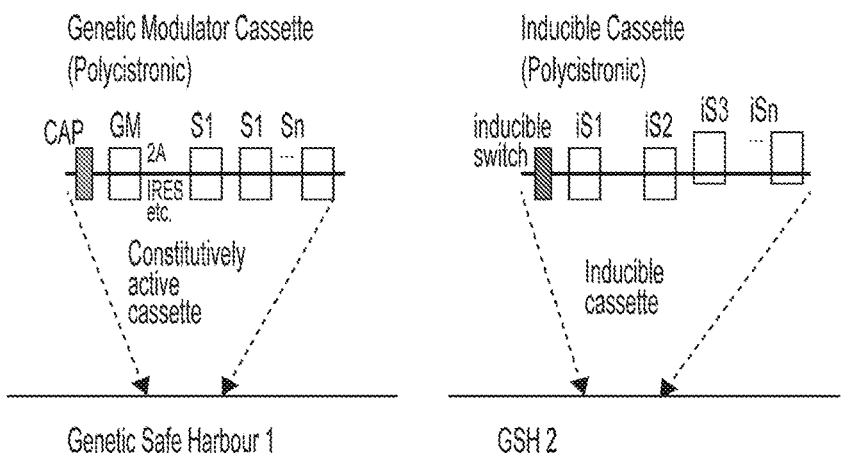
Figure 13:
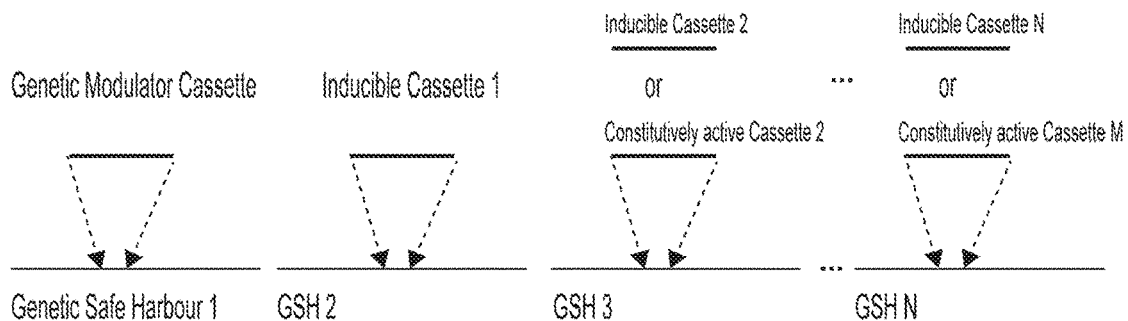

OPTi-OX hPSCs bearing inducible SOX10 either alone or in combination with OLIG2 in form of a bicistronic expression cassette. Although cells induced with SOX10 alone robustly expressed the oligodendrocyte precursor (OPC) marker O4 after 10 days of induction, these cells failed to differentiate further into myelin-expressing cells and progressively died. In contrast, the OLIG2-SOX10 double-overexpressing cells readily progressed from an O4-positive progenitor stage into a mature CNP/MBP-positive phenotype at 20 days post induction. Moreover, additional marker protein expression analysis confirmed that OPTi-OLIG2-SOX10 hPSCs induced in oligodendrocyte media (Douvaras et al. 2014) supplemented with the mitogens PDGFaa and FGF2 first passed through an OPC-like stage in which they were highly proliferative and in which they co-expressed PDGFRA, A2B5, and O4. These cells were highly proliferative and could be maintained for at least three passages (FIG. 12b) by culturing them in the presence of mitogens. We therefore named these cells i-OPCs, for induced OPCS.

Remarkably, following withdrawal of mitogens and in the continued presence of doxycycline, OPCs readily differentiated in approximately one week into mature oligodendrocytes expressing the major myelin proteins CNP, PLP, MAG, MOG and MBP (FIG. 12c-12d) that were capable of myelin sheath formation (data not shown). Collectively, these results demonstrated that the invention allowed the development of a novel, robust and rapid hPSC forward programming protocol for the generation of oligodendrocyte precursors and oligodendrocytes.

TABLE 1

Summary of Genotyping results:

| Locus | Cell Line | Transgene | # clones picked | # clones no on-tar. Integrat(a) | # clones HET + off-targ.(b) | # clones HOM + off-targ.(b) | # clones HET(c) | # clones HOM(c) | Efficiency no off-tar. [%](d) | Efficiency total [%](e) |
|---|---|---|---|---|---|---|---|---|---|---|
| ROSA26 | H9 | rtTA | 23/27/60* | 2/3/1* | 7/13/36* | 5/3/6* | 8/8/14* | 1/0/3* | 39/30/28* | 91/89/98* |
| ROSA26 | iPSC | rtTA | 48 | 8 | 11 | 2 | 25 | 2 | 56 | 83 |
| AAVS1 | H9 | EGFP | 12/12/24* | 2/1/2* | 0/0/0* | 4/5/11* | 0/1/4* | 6/5/7* | 50/50/46* | 83/92/92* |
| AAVS1 | H9 | NGN2 | 6 | 0 | 0 | 0 | 0 | 6 | 100 | 100 |
| AAVS1 | iPSC | NGN2 | 3 | 0 | 0 | 2 | 1 | 0 | 33 | 100 |
| AAVS1 | H9 | MYOD1 | 12 | 2 | 0 | 3 | 0 | 7 | 58 | 75 |
| AAVS1 | iPSC | MYOD1 | 3 | 0 | 1 | 1 | 0 | 1 | 33 | 100 |

(a)Incorrect targeting: No evidence of targeting (lack of bands in 5'- and 3'-integration PCR and presence of WT band in locus PCR) or evidence of targeting, but incorrect size of 5'- or 3'-integration PCR.
(b)Correct on-target integration with additional random integration of the plasmid (bands in 3'-backbone PCR).
(c)Correct on-target integration (HET, heterozygous; HOM, homozygous).
(d)Percentage of clones with correct on-target integration (without additional off-target integration)
(e)Percentage of clones with correct on-target integration (with or without additional off-target integration)
*The three numbers are from three different targeting experiments in hESCs.

TABLE 2

| | | | | |
|---|---|---|---|---|
| | | List of primers used for genotyping PCR | | |
| Locus | PCR type | Primer binding site | Primer sequence | SEQ ID NO: |
| hROSA26 | Locus PCR | Genome (5') | GAGAAGAGGCTGTGCTTCGG | 7 |
| | | Genome (3') | ACAGTACAAGCCAGTAATGGAG | 8 |
| | 5'-INT PCR | Genome (5') | GAGAAGAGGCTGTGCTTCGG | 9 |
| | | Splice Acceptor | AAGACCGCGAAGAGTTTGTCC | 10 |
| | 3'-INT PCR | rtTA | GAAACTCGCTCAAAAGCTGGG | 11 |
| | | Genome (3') | ACAGTACAAGCCAGTAATGGAG | 12 |
| | 3'-BB PCR | rtTA | GAAACTCGCTCAAAAGCTGGG | 13 |
| | | Vector Backbone (3') | TGACCATGATTACGCCAAGC | 14 |
| AAVS1 | Locus PCR | Genome (5') | CTGTTTCCCCTTCCCAGGCAGG TCC | 15 |
| | | Genome (3') | TGCAGGGGAACGGGGCTCAGTC TGA | 16 |
| | 5'-INT PCR | Genome (5') | CTGTTTCCCCTTCCCAGGCAGG TCC | 17 |
| | | Puromycin | TCGTCGCGGGTGGCGAGGCGCA CCG | 18 |
| | 3'-INT PCR | Inducible cassette | inducible cassette specific sequence | |
| | | Genome (3') | TGCAGGGGAACGGGGCTCAGTC TGA | 19 |

TABLE 2-continued

List of primers used for genotyping PCR

| Locus | PCR type | Primer binding site | Primer sequence | SEQ ID NO: |
|---|---|---|---|---|
| 3'-BB PCR | Inducible cassette Vector Backbone (3') | inducible cassette specific sequence | ATGCTTCCGGCTCGTATGTT | 20 |

TABLE 3

List of primers for quantitative PCR

| Gene | Orientation | Primer sequence | SEQ ID NO: |
|---|---|---|---|
| CNP | Fw | TCCTCATCATGAACAGAGGCTT | 21 |
|  | Rev | AAACTGCAGCTCAGGCTTGT | 22 |
| DES | Fw | CCAACAAGAACAACGACGCC | 23 |
|  | Rev | ATCAGGGAATCGTTAGTGCCC | 24 |
| DMD | Fw | TGGTGGGAAGAAGTAGAGGACT | 25 |
|  | Rev | TGCTGCTTCCCAAACTTAGA | 26 |
| EGFP | Fw | CCCGACAACCACTACCTGAG | 27 |
|  | Rev | GTCCATGCCGAGAGTGATCC | 28 |
| FOXG1 | Fw | TGCCAAGTTTTACGACGGGA | 29 |
|  | Rev | GGGTTGGAAGAAGACCCCTG | 30 |
| GRIA4 | Fw | GGCCAGGGAATTGACATGGA | 31 |
|  | Rev | AACCAACCTTTCTAGGTCCTGTG | 32 |
| HMBS (PBGD) | Fw | ATTACCCCGGGAGACTGAAC | 33 |
|  | Rev | GGCTGTTGCTTGGACTTCTC | 34 |
| MAG | Fw | CAGAAGACGTCCCCAACTCA | 35 |
|  | Rev | CCTCGGGAGGCTGAAATCATAA | 36 |
| MAP2 | Fw | AGACTGCAGCTCTGCCTTTAG | 37 |
|  | Rev | AGGCTGTAAGTAAATCTTCCTCC | 38 |
| MBP | Fw | TGGTGATGGAGATGTCAAGCAGGT | 39 |
|  | Rev | GCTGTGGTTTGGAAACGAGGTTGT | 40 |
| MOG | Fw | AGAGATAGAGAATCTCCACCGGA | 41 |
|  | Rev | TGATCAAGGCAACCAAGGGTC | 42 |
| MYH1 | Fw | CACACTAGTTTCACAGCTCTCG | 43 |
|  | Rev | CAGGGCACTCTTGGCCTTTA | 44 |
| MYH2 | Fw | GGAAGCTCTGGTGTCTCAGTT | 45 |
|  | Rev | CAGGGCGTTCTTGGCTTTTAT | 46 |
| MYH3 | Fw | GCTGCATACCCAGAACACCA | 47 |
|  | Rev | CCCTGCTGGCATCTTCTACC | 48 |
| MYH4 | Fw | TCGCATTTGTCAGCCAAGGG | 49 |
|  | Rev | TGAAACCCAGGATGTCCACAG | 50 |
| MYH7 | Fw | GAGACTGTCGTGGGCTTGTA | 51 |
|  | Rev | GCCCTTCTCAATAGGCGCATC | 52 |
| MYH8 | Fw | TGAAGCAGATAGCAGCGCGA | 53 |
|  | Rev | CGTACGAAGTGAGGGTGTGT | 54 |
| MYOD1 (endo) | Fw | GCCGCTTTCCTTAACCACAA | 55 |
|  | Rev | CTGAATGCCCACCCACTGTC | 56 |
| MYOD1 | Fw | CGACGGCATGATGGACTACA | 57 |
|  | Rev | TAGTAGGCGCCTTCGTAGCA | 58 |

TABLE 3-continued

List of primers for quantitative PCR

| Gene | Orientation | Primer sequence | SEQ ID NO: |
|---|---|---|---|
| NANOG | Fw | AGCAGATGCAAGAACTCTCCAA | 59 |
|  | Rev | TGAGGCCTTCTGCGTCACAC | 60 |
| NEUROG2 (NGN2) | Fw | TGTTCGTCAAATCCGAGACCT | 61 |
|  | Rev | CGATCCGAGCAGCACTAACA | 62 |
| PAX6 | Fw | CGAGATTTCAGAGCCCCATA | 63 |
|  | Rev | AAGACACCACCGAGCTGATT | 64 |
| PLP | Fw | AACAGCTGAGTTCCAAATGACC | 65 |
|  | Rev | ACGGCAAAGTTGTAAGTGGC | 66 |
| POU3F2 (BRN2) | Fw | ACCCGCTTTATCGAAGGCAA | 67 |
|  | Rev | CCTCCATAACCTCCCCCAGA | 68 |
| POU5F1 (OCT4) | Fw | GTGGAGGAAGCTGACAACAA | 69 |
|  | Rev | ATTCTCCAGGTTGCCTCTCA | 70 |
| RYR1 | Fw | CAATCGCCAGAACGGAGAGA | 71 |
|  | Rev | GTCGTGTTCCCTGTCTGTGT | 72 |
| SLC17A6 (VGLUT2) | Fw | GTAGACTGGCAACCACCTCC | 73 |
|  | Rev | CCATTCCAAAGCTTCCGTAGAC | 74 |
| SYP | Fw | ACCTCGGGACTCAACACCTCGG | 75 |
|  | Rev | GAACCACAGGTTGCCGACCCAG | 76 |
| SYN1 | Fw | CCCTGGGTGTTTGCCCAGAT | 77 |
|  | Rev | ACCACGGGGTACGTTGTACT | 78 |
| TUBB3 | Fw | CAACCAGATCGGGGCCAAGTT | 79 |
|  | Rev | CCGAGTCGCCCACGTAGTT | 80 |

TABLE 4

List of antibodies

| Antigen | Species | Isotype | Clonality | Company | Cat. No. | Dilution |
|---|---|---|---|---|---|---|
| A2B5 | mouse | IgM | monoclonal | Millipore | MAB312 | 1:300 |
| ACTN2 (α-actinin) | mouse | IgG1 | monoclonal | Sigma | A7811 | 1:200 |
| BrdU | mouse | IgG1 | monoclonal | BD Bio | 347580 | 1:100 |
| CNP | mouse | IgG1 | monoclonal | Abcam | ab6319 | 1:500 |
| DES (desmin) | rabbit | IgG | monoclonal | Abcam | ab32362 | 1:500 |
| EOMES | rabbit | IgG | polyclonal | Abcam | ab23345 | 1:200 |
| MAG | mouse | IgG1 | monoclonal | Abcam | ab89780 | 1:400 |
| MAP2 | mouse | IgG1 | monoclonal | Sigma | M4403 | 1:200 |
| MBP | Rat | IgG2a | monoclonal | Millipore | MAB386 | 1:200 |
| MYOD1 | rabbit | IgG | monoclonal | Abcam | ab133627 | 1:250 |
| MYOG (myogenin) | mouse | IgG1 | monoclonal | DSHB | F5D | 1:100 |
| MYOG (myogenin) | rabbit | IgG | monoclonal | Abcam | ab124800 | 1:500 |
| MYH (myosin heavy chains) | mouse | IgG2b | monoclonal | DSHB | MF20 | 1:100 |
| MYH-PE | mouse | IgG2b | monoclonal | BD Biosc. | 564408 | 1:20 (Flow) |
| NANOG | goat | IgG | polyclonal | R&D | AF1997 | 1:200 |
| NCAM | mouse | IgG1 | monoclonal | DSHB | 5.1H11 | 1:100 |
| O4 | mouse | IgM | monoclonal | R&D | MAB1326 | 1:1000 |
| NKX2.5 | rabbit | IgG | polyclonal | Santa Cruz | sc14033 | 1:200 |
| OCT4 | mouse | IgG2b | monoclonal | Santa Cruz | sc5279 | 1:200 |
| PAX3 | mouse | IgG2a | monoclonal | DSHB | Pax3 | 1:100 |
| PAX6 | mouse | IgG1 | monoclonal | DSHB | PAX6 | 1:100 |
| PAX7 | mouse | IgG1 | monoclonal | DSHB | PAX7 | 1:100 |
| PLP | rabbit | IgG | monoclonal | Abcam | Ab183493 | 1:2000 |
| TNNT2 (troponin T) | mouse | IgG2a | monoclonal | DSHB | CT3 | 1:100 |

TABLE 4-continued

List of antibodies

| Antigen | Species | Isotype | Clonality | Company | Cat. No. | Dilution |
|---|---|---|---|---|---|---|
| TTN (titin) | mouse | IgM | monoclonal | DSHB | 9D10 | 1:100 |
| TetR (tet repressor) | mouse | IgG1 | monoclonal | Clontech | 631131 | 1:1000 (WB) |
| TUBA4A (α4-tubulin) | mouse | IgG1 | monoclonal | Sigma | T6199 | 1:10000 (WB) |
| TUBB3 (βIII-tubulin) | mouse | IgG1 | monoclonal | Millipore | MAB1637 | 1:1000 |
| VGLUT1 | goat | IgG | polyclonal | Abcam | ab104899 | 1:500 |

Example 5: TET-ON Inducible Knockdown System

Development of an Optimized Inducible Knockdown Platform in hPSCs.

Figure 14:
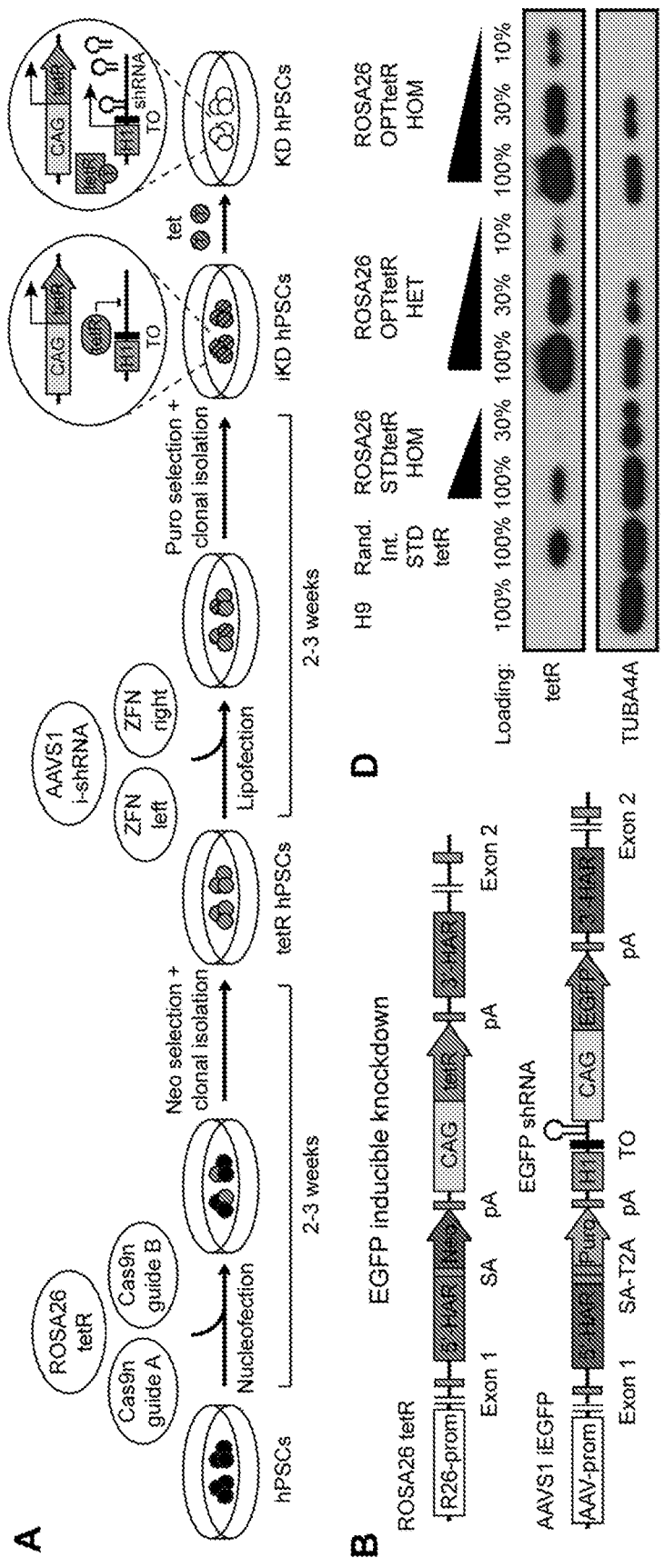
FIG. 14 (a to f) are depictions of the results showing the development of an inducible knockdown system based on dual GSH targeting of hSPCs.
Figure 14:
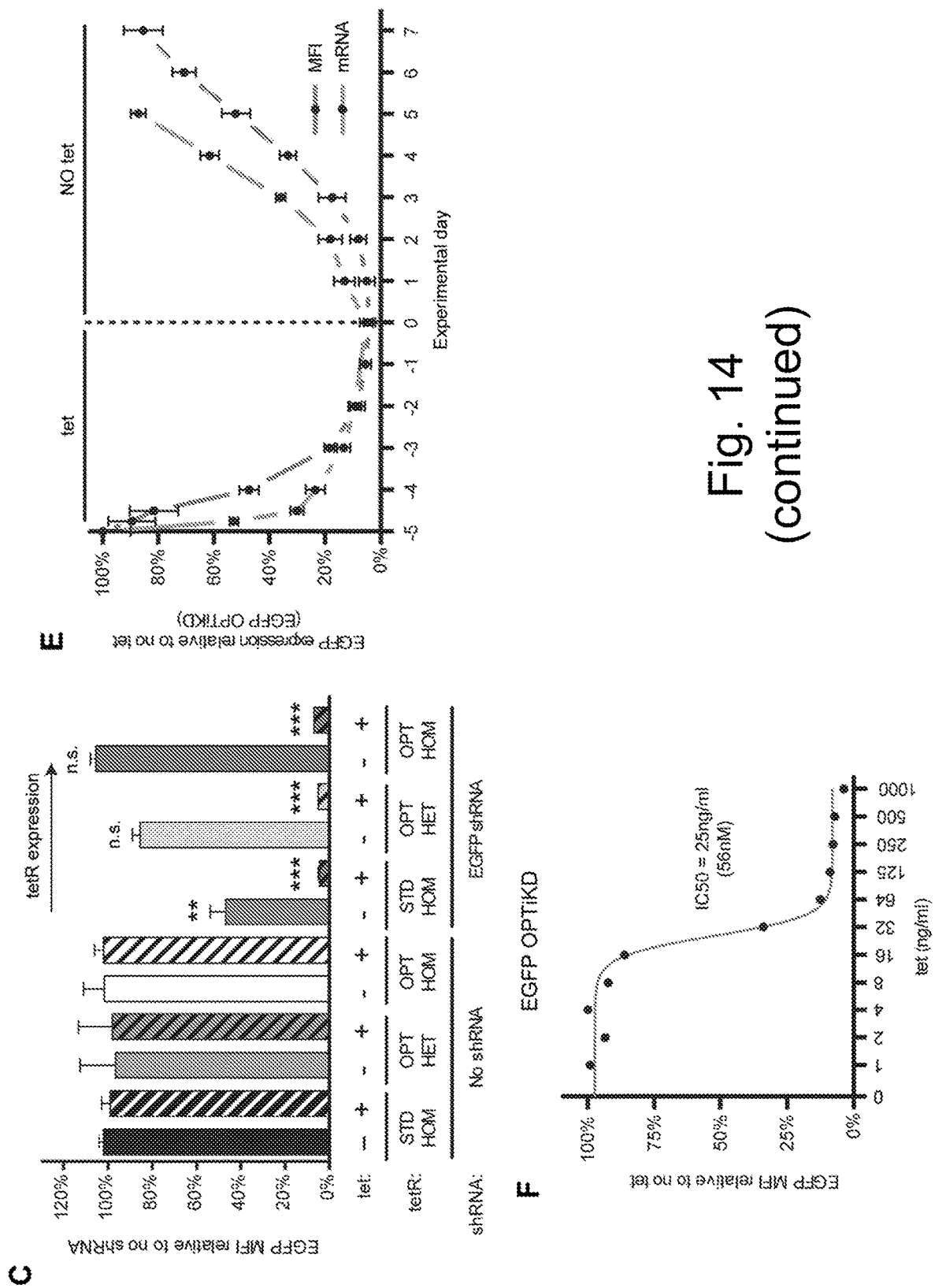

We generated hESC lines in which an EGFP transgene could be silenced in an inducible fashion (FIG. 14B). For that, we targeted: (1) a CAG-tetR expression cassette into the ROSA26 locus; and (2) a CAG-EGFP transgene plus an inducible EGFP shRNA cassette into the AAVS1 locus (FIG. 14A,B). To express higher levels of the tetR protein to more strongly repress shRNA expression in the absence of tetracycline. For this, we performed a multi-parameter RNA and codon optimization of the bacterial tetR cDNA, and used the resulting codon-optimized tetR (OPTtetR) to generate new EGFP inducible knockdown hESC lines (FIG. 14B). This modification allowed a ten-fold increase in the tetR expression when compared to the standard sequence (STDtetR; FIG. 14D). Further, homozygous expression of the OPTtetR was sufficient to completely prevent shRNA leakiness while fully preserving efficient knockdown induction (FIG. 14C). Of note, the inducible knockdown was rapid, reversible, and dose responsive (FIG. 14E,F). Finally, inducible hESCs displayed a normal karyotype (data not shown), demonstrating that the genome engineering necessary to create these lines did not alter their genetic stability.

Based on these encouraging results, we further validated this method in the context of endogenous genes by generating hESCs carrying inducible shRNAs against POU5F1/OCT4 or B2M (data not shown). Remarkably, all the sublines analysed (6 for each gene) showed robust inducible knockdown with no significant shRNA leakiness. Tetracycline titration identified optimal concentrations to partially or fully knockdown OCT4. As expected, a strong decrease in OCT4 specifically resulted in loss of pluripotency and induction of neuroectoderm and definitive endoderm markers. Similar results were obtained with 20 additional OCT4 inducible knockdown hESC sublines, confirming the robustness and reproducibility of this method. Importantly, the generation of hESCs with strong and tightly regulated knockdown was so efficient that phenotypic analyses could be performed immediately after antibiotic selection on a mixed population of cells, thereby entirely bypassing the need of picking individual colonies for clonal isolation. Overall, these results establish that dual targeting of GSHs with an optimized inducible knockdown system is a powerful method to control gene expression in hPSCs. This approach is hereafter named OPTiKD, for OPTimized inducible KnockDown (FIG. 14A).

Example 6

Figure 15:
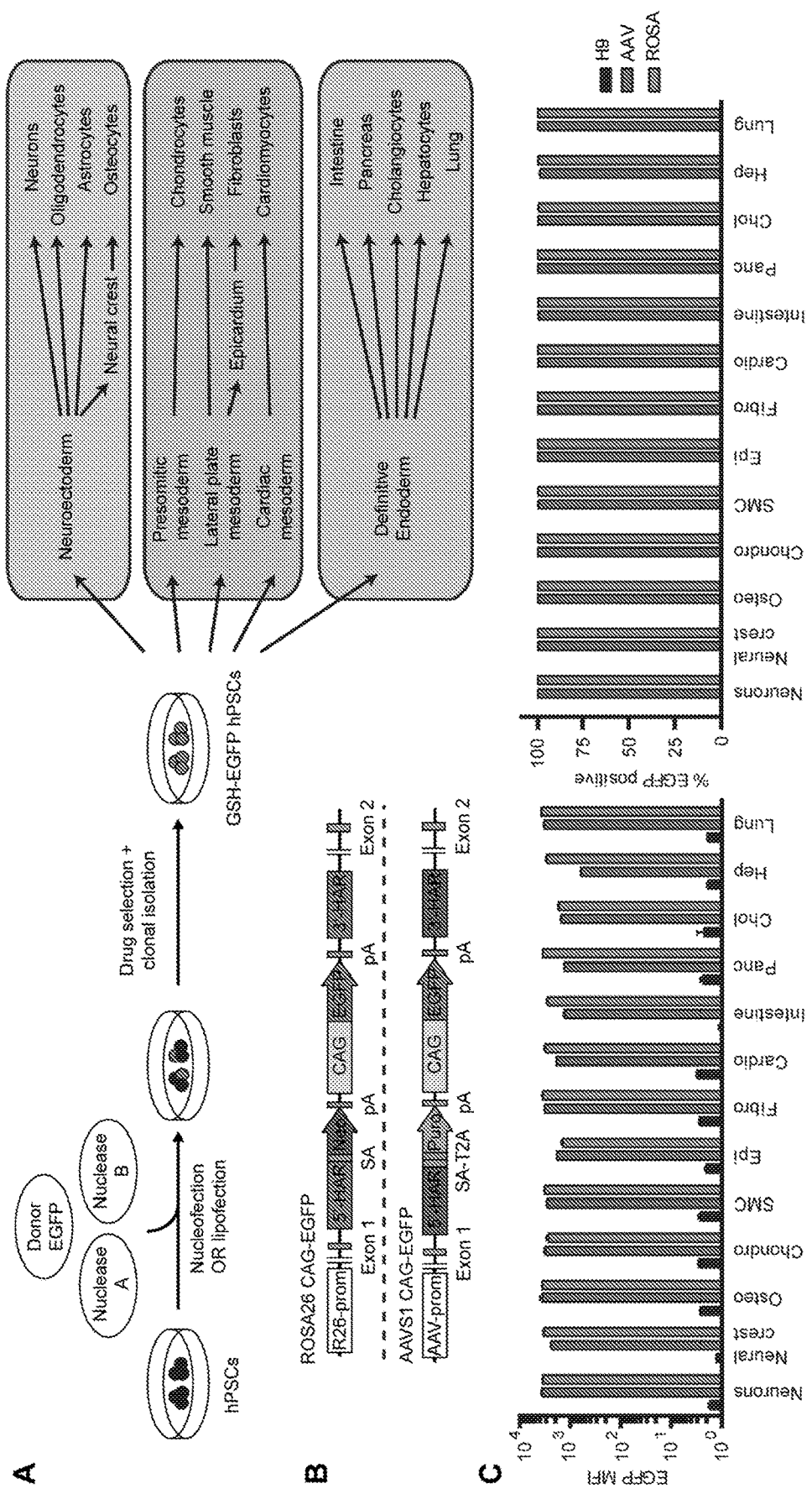
FIG. 15 (a, b and c) Validation of the ROSA26 and AAVS1 loci as bona fide GSH
Figure 17:
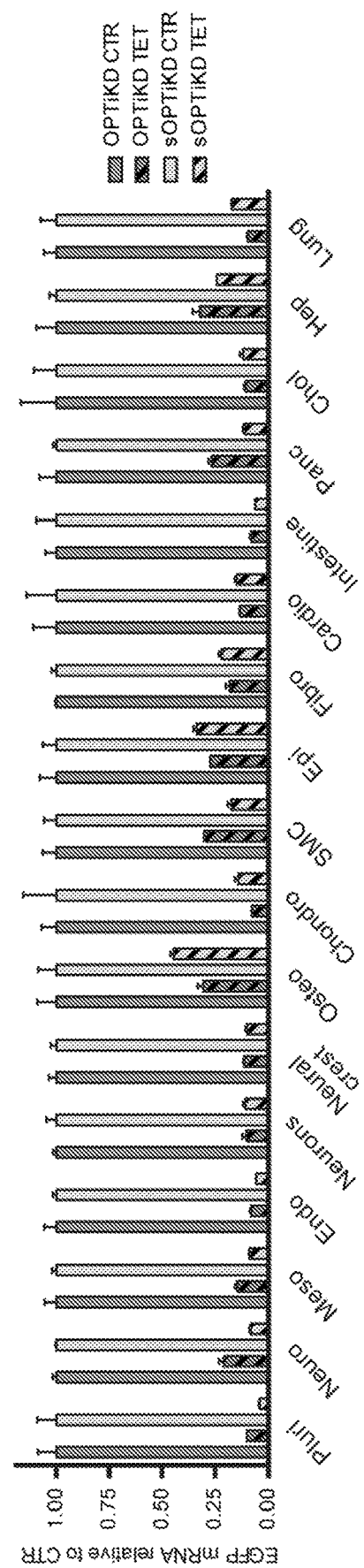
FIG. 17. Validation of the optimized inducible knockdown platforms following hPSC differentiation. The plot shows EGFP expression measured by qPCR in absence (CTR) or presence of tetracycline for 5 days (TET) in the indicated cell types derived from EGFP OPTiKD (iKD) and sOPTiKD (siKD) hESCs. EGFP levels are reported relative to control conditions in the same line for each individual lineage. Abbreviations indicate the lineages described in FIG. 15 (pluri: undifferentiated). Results are from two independent cultures per condition.

The capacity to knockdown genes in a variety of differentiated cells would represent a significant advance over previous systems for inducible gene knockdown. To thoroughly test this possibility, we analysed the efficacy of the OPTiKD platform to knockdown an EGFP transgene in hPSCs differentiated into the three germ layers, as well as in a panel of thirteen fully differentiated cell types (FIG. 15A). For both methods, qPCR analyses demonstrated strong and inducible knockdown of EGFP transcripts in all lineages tested (FIG. 17). Microscopy observations confirmed robust decrease in EGFP protein expression, and flow cytometry showed a decrease of EGFP fluorescence by more than 70% for most lineages (data not shown).

Example 7

Development of an Optimized Inducible CRISPR/Cas9 Knockout Platform in hPSCs.

We turned our attention to developing an inducible knockout approach. Current inducible CRISPR/Cas9 methods rely on conditional overexpression of Cas9 in the presence of a constitutively expressed gRNA. In this case, control of Cas9 overexpression is achieved by a TET-ON method in which following doxycycline treatment a tetracycline-controlled reverse transactivator (rtTA) activates a Pol II-dependent tetracycline responsive element (TRE) promoter (a fusion between multiple TET operons and a minimal CMV promoter). While this TET-ON platform has been successfully applied to certain human cell types, we observed that this inducible system is silenced during hPSC differentiation into multiple lineages (including cardiomyocytes, hepatocytes, and smooth muscle cells), even after targeting into the AAVS1 GSH (data not shown). We explored the possibility to develop an alternative and improved method by combining a constitutively expressed CAG promoter-driven Cas9 with an inducible gRNA cassette based on the one developed for inducible shRNA expression (FIG. 18A,B). We therefore generated hESCs lines in which a fluorescent reporter gene could be knocked out in an inducible fashion (FIG. 18C). For this, we targeted ROSA26-EGFPd2 reporter hESCs with both an inducible EGFP gRNA and a constitutive Cas9 in the AAVS1 locus, each transgene being integrated into one of the two alleles. This dual targeting approach was rapid (<2 weeks) and efficient (>90% of lines containing both transgenes. Remarkably, when individual clonal sublines were grown in the presence of tetracycline we observed decreased EGFPd2 expression in all of the targeted lines, and EGFPd2 homozygous cells showed near-homogeneous loss of at least one copy of the reporter gene as early as five days following tetracycline induction (as demonstrated by 50% reduction in EGFPd2 fluorescence). Prolonged treatment with tetracycline led to progressive full loss of EGFPd2 fluorescence in up to 75% EGFPd2 homozygous cells (data not shown). Interestingly, co-expression of either two or three copies of the same EGFP gRNA cassette from the same AAVS1 locus was sufficient to significantly increase the speed and efficiency of inducible EGFPd2 knockout in all the clonal sublines analysed. For instance, simultaneous induction of three copies of the same gRNA resulted in a remarkable 95% knockout efficiency following tetracycline treatment. Importantly, inducible EGFPd2 knockout hESCs did not show any significant decrease neither in the proportion of EGFPd2 positive cells nor in their fluorescence after prolonged culture in the absence of tetracycline, even when several gRNA copies were used. This demonstrated that the inducible gRNA expression was tightly controlled. Finally, testing of additional gRNAs against EGFPd2 revealed that the speed and efficiency of inducible knockout strongly relied on the gRNA. Indeed, an optimal sequence allowed up to 90% knockout after only 2 days of induction. Of note, the most efficient gRNA also resulted in uncontrolled EGFPd2 knockout, but this limitation was avoided by simply adding a second TET operon to the inducible H1 promoter to ensure even more stringent transcriptional control. Collectively, these results show that the knockdown system could be readily repurposed to support inducible gRNA expression and allow tightly-controlled activity of CRISPR/Cas9 over a broad range of gRNA potency. To the best of our knowledge, this is the first conditional CRISPR/Cas9 approach based on inducible gRNA expression.

What is claimed is:

1. A method for controlling transcription of a genetic sequence in a cell, comprising:
   a) inserting into a cell a gene encoding a transcriptional regulator protein into a first genetic safe harbour site; and
   b) inserting into the cell an inducible cassette into a second genetic safe harbour site, wherein said inducible cassette comprises a genetic sequence operably linked to an inducible promoter, and said promoter is regulated by the transcriptional regulator protein;
   wherein said first and second genetic safe harbour sites are different; and wherein the inserting of each of steps a) and b) is performed in vitro via targeted insertion using a clustered regularly interspaced short palindromic repeats (CRISPR), a zinc-finger nuclease (ZFN), or a transcription activator-like effector nuclease (TALEN).

2. The method of claim 1, wherein the genetic sequence is a transgene.

3. The method of claim 1, wherein the genetic sequence encodes a non-coding RNA.

4. The method of claim 1, wherein the activity of said transcriptional regulator protein is controlled by an exogenously supplied substance.

5. The method of claim 1, wherein said transcriptional regulator protein is constitutively expressed.

6. The method of claim 1, wherein said transcriptional regulator protein is selected from the group consisting of a tetracycline-responsive transcriptional activator protein (rtTa), a Tetracycline repressor (TetR), a VgEcR (ecdysone receptor, DNA binding domain of the glucocorticoid receptor, and the transcriptional activation domain of Herpes Simplex Virus VP16 fusion protein) synthetic receptor, a hybrid transcriptional regulator protein comprising a DNA binding domain from the yeast GAL4 protein, a truncated ligand binding domain from the human progesterone receptor, and an activation domain from the human NF-KB.

7. The method of claim 1, wherein said transcriptional regulator protein is reverse-tetracycline Trans-Activator (rtTA) or a derivative thereof.

8. The method of claim 7, wherein rtTA is controlled by tetracycline or a derivative thereof.

9. The method of claim 8, wherein the rtTA is controlled by tetracycline.

10. The method of claim 7, wherein the inducible promoter includes a Tet Responsive Element (TRE).

11. The method of claim 7, wherein said transcriptional regulator protein is reverse-tetracycline Trans-Activator (rtTA).

12. The method of claim 1, wherein said first and second genetic safe harbour sites are selected from the group consisting of hROSA26 (human Reverse Orientation Splice Acceptor 26) locus, AAVS1 (Adeno-Associated Virus Integration Site 1) locus, CLYBL (citrate lyase beta-like) gene, CCR5 (C-C motif Chemokine Receptor Type 5) gene, and HPRT (Hypoxanthine guanine phosphoribosyltransferase) gene.

13. The method of claim 1, further comprising inserting additional genetic material at the first/and or second genetic safe harbour sites, said additional genetic material selected from the group consisting of:
   a) a suicide gene;
   b) a selectable marker;
   c) a reporter gene; and
   d) a gene for a non-coding RNA.

14. The method of claim 1, wherein said inserting steps are performed ex vivo.

15. The method of claim 1, wherein said cell is selected from a pluripotent stem cell, a somatic stem cell and a mature cell.

16. The method of claim 1, wherein said inserting steps are for programming of pluripotent stem cells into defined mature cells.

17. The method of claim 1, wherein said cell is a pluripotent stem cell and said genetic sequence is selected from a transgene for one or more master regulators and a transcription factor.

18. The method of claim 17, wherein transcription of said genetic sequence results in the forward programming of the cell into a defined mature cell type.

19. The method of claim 1, wherein said cell is a human cell.

20. The method of claim 1, whereby said inserting steps control transcription of a genetic sequence for gene therapy, wherein the genetic sequence encodes a protein or an RNA selected from the group consisting of a wild-type protein, a modified protein, an antigen, an enzyme, a selectable marker, and a non-coding RNA molecule.

21. A cell made by the method of claim 1.

22. The cell of claim 21, for use in therapy.

23. The cell of claim 21, for use in in vitro diagnostics or for tissue engineering.

* * * * *